US009040264B2

(12) United States Patent
Kristof et al.

(10) Patent No.: US 9,040,264 B2
(45) Date of Patent: May 26, 2015

(54) RECOMBINANT CYANOBACTERIUM EXPRESSING A TRANSCRIPTION FACTOR DOMAIN PROTEIN

(75) Inventors: Jessica Kristof, Portland, OR (US); Rekha Seshadri, San Diego, CA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 13/435,315

(22) Filed: Mar. 30, 2012

(65) Prior Publication Data

US 2012/0252080 A1    Oct. 4, 2012

Related U.S. Application Data

(60) Provisional application No. 61/470,178, filed on Mar. 31, 2011.

(51) Int. Cl.
*C12N 1/20*       (2006.01)
*C12P 7/64*       (2006.01)
*C12N 15/00*      (2006.01)
*C07K 14/195*     (2006.01)

(52) U.S. Cl.
CPC .................. *C12P 7/64* (2013.01); *C07K 14/195* (2013.01); *Y02E 50/13* (2013.01)

(58) Field of Classification Search
None
See application file for complete search history.

(56) References Cited

U.S. PATENT DOCUMENTS

| | | | | |
|---|---|---|---|---|
| 5,455,167 | A | 10/1995 | Voelker et al. | 435/172.3 |
| 5,654,495 | A | 8/1997 | Voelker et al. | 800/250 |
| 5,851,796 | A | 12/1998 | Schatz | 435/69.1 |
| 7,118,896 | B2 | 10/2006 | Kalscheuer et al. | 435/134 |
| 7,135,290 | B2 | 11/2006 | Dillon | 435/6 |
| 7,294,759 | B2 | 11/2007 | Allen et al. | 800/281 |
| 7,803,623 | B2 | 9/2010 | Caimi et al. | 435/471 |
| 8,541,208 | B1 * | 9/2013 | Plesch et al. | 435/106 |
| 2003/0126638 | A1 | 7/2003 | Allen et al. | 800/281 |
| 2008/0148432 | A1 | 6/2008 | Abad | 800/279 |
| 2009/0298143 | A1 | 12/2009 | Roessler et al. | 435/134 |
| 2010/0068776 | A1 | 3/2010 | Woods et al. | 435/161 |
| 2010/0105963 | A1 | 4/2010 | Hu | 568/840 |
| 2010/0255550 | A1 | 10/2010 | Benning et al. | 435/134 |
| 2011/0020883 | A1 | 1/2011 | Roessler et al. | 435/134 |
| 2011/0072714 | A1 | 3/2011 | Gaertner | 44/388 |

FOREIGN PATENT DOCUMENTS

| | | | |
|---|---|---|---|
| WO | WO 03/001902 | 1/2003 | |
| WO | WO-2008/131359 A1 | 10/2008 | |
| WO | WO 2008/157226 | 12/2008 | A01H 5/00 |
| WO | WO-2009/076559 A1 | 6/2009 | |
| WO | WO 2009/077545 | 6/2009 | C12N 15/82 |
| WO | WO 2009/140696 | 11/2009 | C12N 9/04 |
| WO | WO 2009/140701 | 11/2009 | C12N 15/87 |
| WO | WO 2010/039750 | 4/2010 | C12N 15/82 |
| WO | WO 2010/075483 | 7/2010 | C12N 9/16 |
| WO | WO 2011/008565 | 1/2011 | C07H 21/04 |
| WO | WO-2011/011568 A2 | 1/2011 | |
| WO | WO 2011/066137 | 6/2011 | A01N 43/00 |
| WO | WO-2012/087673 A1 | 6/2012 | |

OTHER PUBLICATIONS

López-Redondo et al., Mol. Microbiol. 78:475-489, Sep. 2010.*
UniProtKB Accession No. Q31N86, Mar. 2010, 1 page.*
Seki et al., J. Biol. Chem. 282:36887-36894, 2007.*
Holzinger et al., Micron 37:190-207, 2006.*
Kappell, A. D., "The control of gene expression by high light stress in cyanobacteria through the apparent two-component NbIS-RpaB signal transduction pair", Dissertation, University of Texas at Arlington, Aug. 2008.*
Seino et al., J. Bacteriol. 191:1581-1586, 2009.*
Altschul, S., et al. (1997), "Gapped BLAST and PSI-BLAST: a new generation of protein database search programs", *Nucleic Acids Research*, 25(17): 3389-3402.
Arabolaza, A., et al. (2010), "FasR, a novel class of transcriptional regulator, governs the activation of fatty acid biosynthesis genes in *Streptomyces coelicolor*", *Molecular Microbiology*, 78(1): 47-63.
Aravind, L., et al. (2005), "The many faces of the helix-turn-helix domain: transcription regulation and beyond", *FEMS Microbiology Reviews*, 29: 231-262.
Babu, M., et al. (2006), "Evolutionary Dynamics of Prokaryotic Transcriptional Regulatory Networks", *J Mol. Biol.*, 358: 614-633.
Barnard, A., et al. (2004), "Regulation at complex bacterial promoters: how bacteria use different promoter organizations to produce different regulator outcomes", *Current Opinion in Microbiology*, 7: 102-108.
Bateman, A., et al. (2000), "The pfam protein families database", *Nucleic Acids Research*, 28(1):263-266.
Bateman, A., et al. (2004), "The pfam protein families database", *Nucleic Acids Research*, 32: Database Issue: D138-D141.
Bourret (2010), "Receiver domain structure and function in response regulator proteins" *Current Opinion in Microbiology*, 13: 142-149.

(Continued)

*Primary Examiner* — David J Steadman
(74) *Attorney, Agent, or Firm* — Harness, Dickey & Pierce, P.L.C.

(57) ABSTRACT

The invention provides microorganisms such as cyanobacteria genetically engineered to express proteins that include transcription factor domains for upregulation of lipid biosynthetic pathways. In addition to expression a gene encoding a transcription factor domain protein, the recombinant microorganisms can express at least one exogenous gene that encodes a polypeptide for the production of a fatty acid, fatty acid derivative, or triglyceride. Also included are methods of producing a fatty acid, fatty acid derivative, or triglyceride using the engineered microorganisms described herein as well as nucleic acid molecules encoding novel transcription factor domain proteins.

18 Claims, 5 Drawing Sheets

(56) References Cited

OTHER PUBLICATIONS

Buikema, W., et al. (2000), "Expression of the anabaena hetR gene from a copper-regulated promoter leads to heterocyst differentiation under repressing conditions", *Proc. Natl. Acad. Sciences USA* 98(5): 2729-2734.

Campbell, J., et al. (2001), "*Escherichia coli* FadR positively regulates transcription of the *fabB* fatty acid biosynthetic gene", *Journal of Bacteriology*, 183(20): 5982-5990.

Cao, Y., et al. (2010), "Increasing unsaturated fatty acid contents in *Escherichia coli* by coexpression of three different genes", *Applied Genetics and Molecular Biotechnology*, 87: 271-280.

Charoensawan, V., et al. (2010), "Genomic repertoires of DNA-binding transcription factors across the tree of life", *Nucleic Acids Research*, 38(21): 7634-7377.

Christoffersen, C., et al. (2001), "Regulatory architecture of the Iron-Regulated *fepD-ybdA* bidirectional promoter region in *Escherichia coli*" 183(6): 2059-2070.

Copeland, A., et al. (2010), Uniprot direct submission B2J280, Retrieved from the internet <URL: http://www.uniprot.org/uniprot/B2J280.txt?version=11>.

Copeland, A., et al. (2011), Uniprot direct submission A5VC88, Retrieved from the internet <URL: http://www.uniprot.org/uniprot/A5VC88.txt?version=27>.

Feng, Y., et al. (2009), *Escherichia coli* unsaturated fatty acid synthesis complex transcription of the fabA gene and in vivo identification of the essential reaction catalyzed, *J Bio Chem*, 284(43): 29526-29535.

Finn, R., et al. (2006), "Pfam: clans, web tools and services", *Nucleic Acids Research*, 34: Database Issue 34:D247-D251.

Finn, R., et al. (2010), "The pham protein families database", *Nucleic Acids Research*, 38: Database Issue 38:D211-D222.

Fujita, Y., et al. (2007), "Regulation of fatty acid metabolism in bacteria", *Molecular Microbiology*, 66(4), 829-839.

Gao, R., et al. (2010), "Molecular strategies for phosphorylation-mediated regulation of response Regulatory activity", *Current Opinion Microbiology*, 13(2): 160-167.

Henikoff, S., et al. (1992), "Amino acid substitution matrices from protein blocks", *Proc. Natl. Acad. Sci USA*, 89:10915-10919.

Huffman, J., et al. (2002), "Prokaryotic transcription regulators: more than just the helix-turn-helix motif", *Current Opinion in Structural Biology*, 12:98-106.

International Search Report for PCT/US12/31534 Dated Jul. 2, 2012.

Iram, S., et al. (2005), "Unexpected functional diversity among fadR fatty acid transcriptional regulatory proteins", *The Journal of Biological Chemistry*, 280(37): 32148-32156.

Jerga, A., et al. (2009), Acyl-Acyl Carrier Protein Regulates Transcription of fatty acid biosynthetic genes via the FabT repressor in *Streptococcus pneumoniae The Journal of Biological Chemistry*, 284(23): 15364-15368.

Karlin, S., et aL, (1990), "Methods for assessing the statistical significance of molecular sequence features by using general scoring schemes", *Proc. Natl. Acad. Sci. USA*, 87: 2264-2268.

Liu, X., et al. (2009), "Nickel-inducible lysis system in *Synechocystis* sp. PCC 6803", *Proc. Natl. Acad. Sciences USA* 106: 21550-21554.

Lozada-Chávez, I., et al. (2008), "The role of DNA-binding specificity in the evolution of bacterial regulatory networks", *J. Mol. Biol.*, 379: 627-643.

Lu, Y., et al. (2006), "Transcriptional regulation of fatty acid biosynthesis in *Streptococcus pneumoniae*", *Molecular Biology*, 59(2): 551-566.

Lu, X., et al. (2008), "Overproduction of free fatty acids in *E. coli*: Implications for biodiesel production", *Metabolic Engineering*, 10: 333-339.

Lucas, S., et al. (2011), Uniprot direct submission B7KMW0, Retrieved from the internet <URL: http://www.uniprot.org/uniprot/B7KMW0.txt?version=16>.

Méndez-Alvarez, S., et al. (1994), "Transformation of *Chlorobium limicola* by a plasmid that confers the ability to utilize thiosulfate" *Journal of Bacteriology*, 176(23):7395-7397.

Nakamura, Y., et al. (2011), Uniprot direct submission Q8DHT6, Retrieved from the internet <URL: http://www.uniprot.org/uniprot/Q8DHT6.txt?version=40>.

Ohnuma M., et al. (2008), "Polyethylene glycol (PEG)-mediated transient gene expression in a red alga, *cyanidioschyzon* merolae 10D", *Plant Cell Physiol.*, 49(1):117-120.

Paoletti, L., et al. (2007), "Coupling of fatty acid and phospholipid Synthesis in *Bacillus subtilis*", *Journal of Bacteriology*, 189(16): 5816-5824.

Perrone, C., et al. (1998), "The *Chlamydomonas* IDA7 locus encodes a 140 kDa dynein intermediate chain required to assemble the I1 inner arm complex", *Molecular biology of the Cell*, 9:3351-3365.

Podkovyrov, S., et al. (1996), "Identification of promoter and stringent regulation of transcription of fabH, fabD and fabG genes encoding fatty acid biosynthetic enzymes of *Escherichia coli*", *Nucleic Acids Research*, 24(9): 1747-1752.

Rabin, R., et al., (1992), "In vivo requirement of integration host factor for nar (nitrate reductase_ operon expression in *Escherichia coli* K-12" *Proc. Natl. Acad. Sci, USA*, 89: 8701-8705.

Ruffing, A., (2011), "Engineered cyanobacteria, teaching an old bug new tricks", *Bioengineered bugs*, 2(3): 136-149.

Sato, N., et al., (2009), "Lipid biosynthesis and its regulation in cyanobacteria", *Lipids in Photosynthesis: Essential and Regulatory Functions*, 157-177.

Sonnhammer, E., et al. (1998), "Pfam: multiple sequence alignments and HMM-profiles of protein domains" *Nucleic Acids Research* 26(1):320-322.

Stegmaier, P., et al., (2004), "Systematic DNA-Binding Domain Classification of Transcription Factors", *Genome Informatics*, 15(2) 276-286.

Stemmer, W., (1994), "DNA shuffling by random fragmentation and reassembly: in vitro recombination for molecular evolution", *Proc. Natl. Acad. Sci. USA*, 91: 10747-10751.

Tandeau de Marsac, N., et al. (2010), Uniprot direct submission B4VK88, Retrieved from the internet <URL: http://www.uniprot.org/uniprot/B4VK88.txt?version=13>.

Thelwell, C., et al. (1998), "An SmtB-like repressor from *Synechocystis* PCC 6803 regulates a zinc exporter", *Proc. Natl. Acad. Sci. USA*, 95:10728-10733.

van Hijum, S., et al. (2009), "Mechanisms and evolution of control logic in prokaryotic transcriptional regulation" *Microbiology and Molecular Biology Reviews*, 73(3): 481-509.

Weisner, C., et al. (2002), "A functional screening assay for the isolation of transcription factors", *Nucleic Acids Research*, 30(16), e80.

West, A., et al., (2001), "Histidine kinases and response regulator proteins in two-component signaling systems", *Trends Biochem Sci.*, 26(6): 369-376.

Whitworth, D., et al. (2009), "Evolution of prokaryotic two-component systems: insights from comparative genomics", *Amino Acids*, 37: 459-466.

Wintjens, R., et al. (1996), "Structural Classification of HTH DNA-binding Domains and Protein-DNA Interaction Modes", *Journal of Molecular Biology*, 262: 294-313.

Wolk, P., et al. (1984), "Construction of shuttle vectors capable of conjugative transfer from *Escherichia coli* to nitrogen-fixing filamentous cyanobacteria", *Proc. Natl. Acad. Sci. USA*, 81: 1561-1565.

Zhang, Y., et al. (2002), "The fabR (YijC) transcription favor regulates unsaturated fatty acid biosynthesis in *Escherichia coli*", *The Journal of Biological Chemistry*, 277(18), 15558-15565.

Zhang, Y., et al. (2008), "Membrane lipid homeostasis in bacteria", doi: 10.1038/nrmicro1839.

Zhang, Y., et al. (2010), "A rainbow coalition of lipid transcriptional regulators", *Molecular Biology*, 78(1), 5-8.

Zhou, D., et al. (2006), "Global analysis of gene tranxcription regulation in prokaryotes" *Cell Mol. Life Sci.* 63: 2260-2290.

Zhu, K., et al. (2009), "Transcriptional Regulation of Membrane Lipid Homeostasis in *Escherichia coli*" *The Journal of Biological Chemistry*, 284(50): 34880-34888.

(56) References Cited

OTHER PUBLICATIONS

International Preliminary Report on Patentability dated Oct. 1, 2013 from International Application No. PCT/US2012/031534.
Courchesne, N.M.D., et al. (2009) "Enhancement of lipid production using biochemical, genetic and transcription factor engineering approaches", *Journal of Biotechnology*, 141:31-41.
Gibson, J.L., et al. (1996) "The molecular regulation of the reductive pentose phosphate pathway in Proteobacteria and Cyanobacteria", *Arch Microbiol*, 166:141-150.
Liu, X., et al. (2011) "Fatty acid production in genetically modified cyanobacteria", *PNAS*, 108(17):6899-6904.
Lu, X. (2010) "A perspective: photosynthetic production of fatty acid-based biofuels in genetically engineered cyanobacteria", *Biotechnology Advances*, 28:742-746.
Supplemental European Search Report dated Oct. 13, 2014 issued in EP Application No. 12765005.9.
UniProt Accession No. A5VC87, Jul. 10, 2007, 2 pages.
UniProt Accession No. B2J281, Jun. 10, 2008, 1 page.

\* cited by examiner in# RECOMBINANT CYANOBACTERIUM EXPRESSING A TRANSCRIPTION FACTOR DOMAIN PROTEIN

CROSS-REFERENCE TO RELATED APPLICATIONS

This application claims benefit of priority to U.S. Provisional application 61/470,178 filed Mar. 31, 2011 entitled "Metabolic Pathway Targeting by Transcription Factor Overexpression", which is incorporated by reference in its entirety.

REFERENCE TO A SEQUENCE LISTING

This application contains references to amino acid sequences and/or nucleic acid sequences which have been submitted concurrently herewith as the sequence listing text file "60941198_1.txt", file size 64 KiloBytes (KB), created on Mar. 29, 2012. The aforementioned sequence listing is hereby incorporated by reference in its entirety pursuant to 37 C.F.R. §1.52(e)(5). The substitute sequence listing in the ASCII text file entitled "60941198_2.txt" is hereby incorporated by reference in its entirety. The ASCII text file entitled "60941198_2.txt" was created on Apr. 9, 2012 and the size is 66 KB.

TECHNICAL FIELD

The present invention relates, in one aspect, to the regulation of a metabolic pathway in a photosynthetic microorganism, and in particular aspects to the regulation of pathways for the synthesis of fatty acids, fatty acid derivatives, and/or lipids. The present invention also relates to methods of producing lipids, fatty acids, and/or fatty acid derivatives in photosynthetic microorganisms, which can be used for a variety of products, including biofuels.

BACKGROUND

Fossil fuel is a general term for buried combustible geologic deposits of organic materials, formed from decayed plants and animals that have been converted to crude oil, coal, natural gas, or heavy oils by exposure to heat and pressure in the earth's crust over hundreds of millions of years. The utilization of fossil fuels has enabled large-scale industrial development and largely supplanted water driven mills, as well as the combustion of wood or peat for heat. Fossil fuels are a finite, non-renewable resource. When generating electricity, energy from the combustion of fossil fuels is often used to power a turbine.

Increased demand for energy by the global economy has also placed increasing pressure on the cost of fossil fuels. Aside from energy, many industries, including plastics and chemical manufacturers, rely heavily on the availability of fossil fuel derivatives as a feedstock for their manufacturing processes. Cost-effective alternatives to current sources of supply could help mitigate the upward pressure on energy and these raw material costs. Major efforts to this end are focused on the microbial production of high-energy fuels by cost-effective consolidated bioprocesses.

Fatty acids are composed of long alkyl chains and represent nature's petroleum, being a primary metabolite used by cells for both chemical and energy storage functions. These energy-rich molecules are today isolated from plant and animal oils for a diverse set of products ranging from fuels to oleochemicals. A more scalable, controllable and economic route to this important class of chemicals would be beneficial to the development of renewable energy sources.

SUMMARY OF THE INVENTION

The invention relates to transcription factor proteins and nucleic acids encoding such proteins. These transcription factor domain proteins, when expressed in cyanobacteria, increase the amount of fatty acids produced by the cyanobacteria.

The invention provides a recombinant or isolated nucleic acid molecule comprising a nucleic acid sequence encoding a polypeptide comprising an amino acid sequence having at least 60%, 65%, 70%, 75%, 80%, 85%, 90%, 95%, or 99% sequence identity to SEQ ID NO:2, SEQ ID NO:4, SEQ ID NO:6, SEQ ID NO:10, SEQ ID NO:12, SEQ ID NO:14, or SEQ ID NO:16, or a functional fragment thereof. The polypeptide can include a transcription factor domain. As nonlimiting examples, the polypeptide can include a helix-turn-helix domain, a winged helix domain, a response regulator receiver domain, or a histidine kinase domain. Expression of the polypeptide encoded by the nucleic acid molecule in a photosynthetic microorganism, such as but not limited to a cyanobacterium, can results in elevated production of a lipid, fatty acid, or fatty acid derivative by the microorganism.

Additionally or alternately, the isolated or recombinant nucleic acid molecule comprises a nucleic acid sequence having at least 50%, 55%, 60%, 65%, 70%, 75%, 80%, 85%, 90%, 95%, 99%, or 100% sequence identity to SEQ ID NO:1, SEQ ID NO:3, SEQ ID NO:5, SEQ ID NO:9, SEQ ID NO:11, SEQ ID NO:13, or SEQ ID NO:15 or a portion thereof encoding a polypeptide having transcription factor activity. The isolated or recombinant nucleic acid molecule comprising a nucleic acid sequence having at least 50%, 55%, 60%, 65%, 70%, 75%, 80%, 85%, 90%, 95%, 99%, or 100% sequence identity to SEQ ID NO:1, SEQ ID NO:3, SEQ ID NO:5, SEQ ID NO:9, SEQ ID NO:11, SEQ ID NO:13, or SEQ ID NO:15 or a fragment thereof can encode a polypeptide having at least 60%, 65%, 70%, 75%, 80%, 85%, 90%, 95%, or 99% sequence identity to SEQ ID NO:2, SEQ ID NO:4, SEQ ID NO:6, SEQ ID NO:10, SEQ ID NO:12, SEQ ID NO:14, or SEQ ID NO:16, or a functional fragment thereof. Further additionally or alternately, the isolated or recombinant nucleic acid molecule disclosed herein that encodes a transcription factor domain protein can be operably linked to one or more expression control elements.

The invention further provides a vector comprising the isolated nucleic acid molecule described herein. In some embodiments, the vector can be an integration vector. In further embodiments, the nucleic acid can be under control of an inducible promoter. In some examples the nucleic acid molecules encoding a transcription factor domain protein is operably linked to a promoter that is functional in cyanobacteria. For example, in particular embodiments, the inducible promoter comprises can be isopropyl β-D-1-thiogalactopyranoside-inducible trcE or trcY promoter.

The invention also provides a cyanobacterium comprising an exogenous nucleic acid molecule encoding a transcription factor domain protein, wherein the cyanobacterium produces a greater amount of at least one lipid, free fatty acid, or fatty acid derivative than does a cyanobacterium identical in all respects except that it does not contain an exogenous nucleic acid molecule encoding the transcription factor domain protein. The transcription factor domain protein can be, as non-limiting examples, a member of a helix-turn-helix family, a member of a winged helix family, a response regulator protein, or a histidine kinase. Optionally but preferably, the transcription factor domain protein comprises an amino acid sequence having at least 60%, 65%, 70%, 75%, 80%, 85%, 90%, 95%, or 100% sequence identity to SEQ ID NO:2, SEQ ID NO:4, SEQ ID NO:6, SEQ ID NO:10, SEQ ID NO:12, SEQ ID NO:14, or SEQ ID NO:16, or a functional fragment thereof.

Also provided herein is a recombinant cyanobacterium that includes an endogenous nucleic acid sequence encoding an ortholog of any of the polypeptides of SEQ ID NO:2, SEQ ID NO:4, SEQ ID NO:6, SEQ ID NO:10, SEQ ID NO:12, SEQ ID NO:14, or SEQ ID NO:16, for example an endogenous nucleic acid sequence encoding a polypeptide that has at least 50%, 55%, 60%, 65%, 70%, 75%, 80%, 85%, 90%, 95%, or 100% sequence identity to SEQ ID NO:2, SEQ ID NO:4, SEQ ID NO:6, SEQ ID NO:10, SEQ ID NO:12, SEQ ID NO:14, or SEQ ID NO:16, or a functional fragment thereof, in which the cyanobacterium is engineered to include a heterologous promoter inserted upstream of the endogenous nucleic acid sequence, such that the heterologous promoter is operably linked to the endogenous nucleic acid sequence encoding a transcription factor domain protein. Preferably, the heterologous promoter is regulatable, for example, inducible.

Alternatively or in addition, the transgenic cyanobacterium may include an exogenous gene encoding an homologous transcription factor domain protein, wherein the transcription factor domain protein is overexpressed in the cyanobacterial host. Alternatively, the transcription factor domain protein encoded by an exogenous gene can be a heterologous protein. Additionally, the cyanobacterium can include an exogenous nucleic acid molecule encoding an homologous or heterologous transcription factor domain protein, in which the nucleic acid molecule further comprises a promoter operably linked to the sequence encoding the transcription factor domain protein. The promoter can be heterologous with respect to the transcription factor domain protein, and may be a cyanobacterial promoter or a promoter not derived from a cyanobacterial species. The promoter is preferably a regulatable promoter, for example, an inducible promoter.

The cyanobacterium that includes an exogenous gene encoding a transcription factor domain protein according to some embodiments of the present invention further comprises at least one additional exogenous gene, in which the at least one additional exogenous gene encodes a protein for production of a fatty acid or a fatty acid derivative. For example, the cyanobacterium can further comprise a nucleic acid molecule encoding a thioesterase and/or polypeptide having lipolytic activity. The thioesterase can be, for example, an acyl-ACP thioesterase, an acyl-CoA thioesterase, or a hydroxybenzoyl thioesterase. The polypeptide having lipolytic activity can be, as nonlimiting examples, a lipase that is a member of a Pfam belonging to the AB Hydrolase Pfam clan (CL0028), such as a member of Pfam PF01674, Pfam PF01764, Pfam PF07819, Pfam PF03583, Pfam PF00151, Pfam PF00561, Pfam PF02230, Pfam PF07859, Pfam PF08386, Pfam PF12695, Pfam PF12697, Pfam PF12715, or Pfam PF04083. The lipase can be, for example, SEQ ID NO:22, SEQ ID NO:24, or SEQ ID NO:26. Further, the recombinant microorganism can include a non-native gene encoding an amidase having lipolytic activity, such as but not limited to an amidase that recruits to Pfam PF01425.

Additionally or in various alternative embodiments, the cyanobacterium can further comprise at least one additional exogenous gene encoding an enzyme selected from the group consisting of an acetyl CoA carboxylase, a ketoacyl-CoA synthase, an acyl-CoA synthetase, a fatty acyl-CoA/aldehyde reductase, an alcohol-forming fatty acyl-CoA reductase, a fatty aldehyde-forming fatty acyl-CoA reductase, and acyl-ACP reductase, a carboxylic acid reductase, a fatty acid elongase, a fatty aldehyde reductase, an alcohol acetyl transferase, an acyl-CoA alcohol transacylase, an acyltransferase, a wax synthase, a fatty aldehyde decarbonylase, or a fatty acid decarboxylase. Additionally or alternatively, the cyanobacterium that includes an exogenous gene encoding a transcription factor can further include at least one additional exogenous gene encoding an enzyme selected from the group consisting of a glycerolphosphate acyltransferase (GPAT), lysophosphatidic acid acyltransferase (LPAAT), phosphatidic acid phosphatase (PA), or diacylglycerol O-acyltransferase (DGAT).

In some embodiments, the cyanobacterium described herein is selected from a group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* and *Xenococcus*.

The invention also provides a method of producing a fatty acid or fatty acid derivative, the method comprising culturing a cyanobacterium as described herein under conditions in which the nucleic acid molecule that encodes a transcription factor domain protein is expressed to produce at least one fatty acid or fatty acid derivative. Optionally but preferably, the cyanobacterium is cultured phototrophically. In preferred embodiments, the amount of the fatty acid or fatty acid derivative produced can be at least about 5%, 8%, 10%, 15%, 20%, 30%, 40%, 50%, 60%, 70%, 80%, 90%, 100%, 150%, or 200% more than the amount of the fatty acid or fatty acid derivative produced by a cyanobacterium not including the exogenous gene encoding the transcription factor domain protein, but identical in all other respects. Additionally or alternately, the amount of the fatty acid or fatty acid derivative produced by the transgenic cyanobacterium that includes an exogenous transcription factor domain protein gene as described herein can be at least about 290 mg per liter of culture. Additionally, the method of producing a fatty acid or fatty acid derivative can further comprise isolating at least one free fatty acid or at least one fatty acid derivative from the cyanobacteria or from the growth media.

Figure 4:
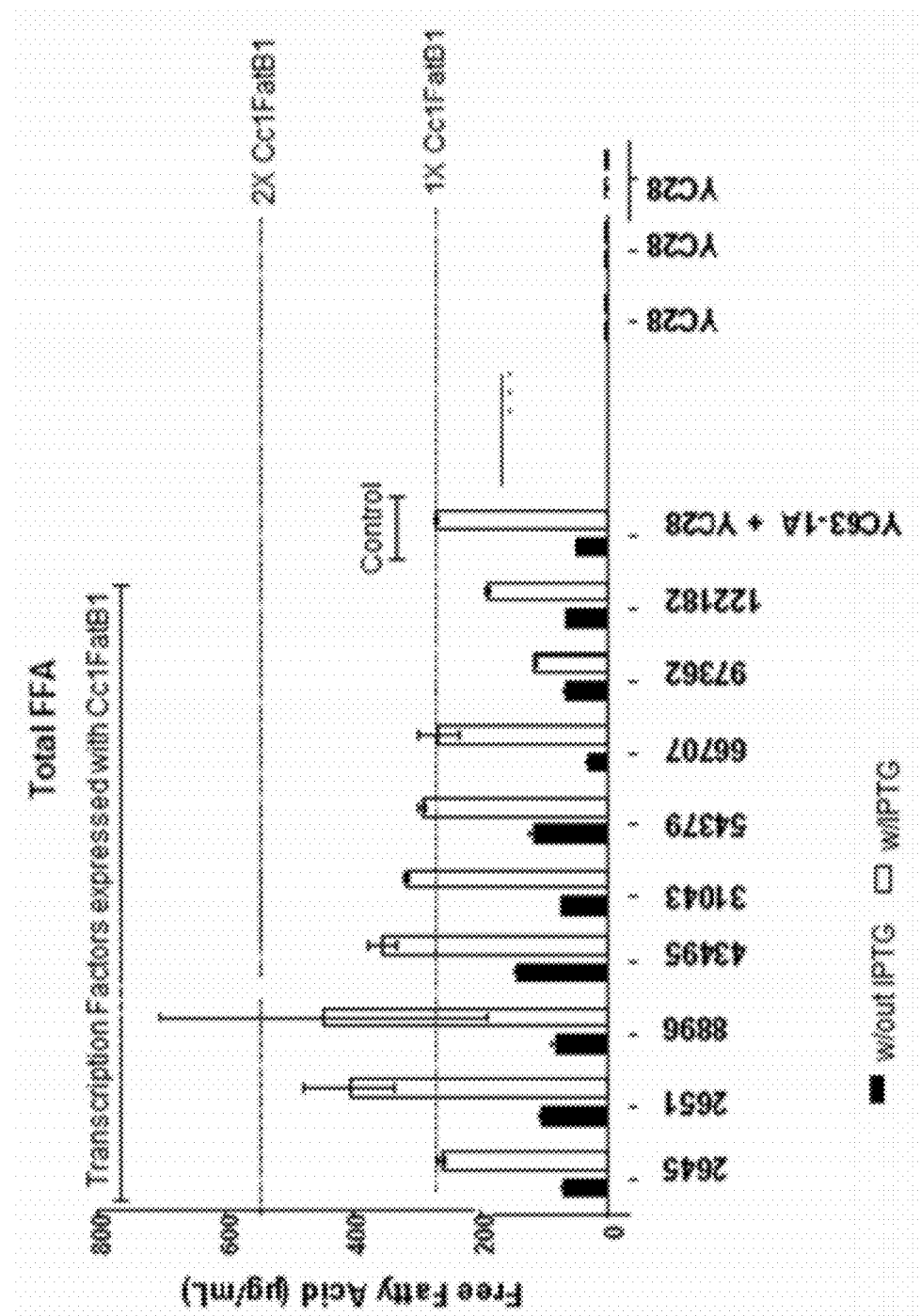

FIG. 4: Graph depicting results of free fatty acid screening in *Synechocystis* 6803. Fatty acid production of cyanobacterial strains containing potential putative transcription factor genes 2645, 2651, 8896, 43495, 31043, 54379, 66707, 97362, and 122182 in combination with the Cc1FatB1 thioesterase gene is shown. Control strains that included the YC63-1A construct that included the Cc1FatB1 thioesterase gene and a YC28 vector lacking a putative transcription factor, and further controls in the form strains containing an empty vector only (YC28) were tested in *Synechocystis* 6803 to determine relative free fatty acid production. Transcription factors in this experiment were under the control of the inducible promoter TrcE, and the results are shown with (dark bars) and without (light bars) IPTG induction.

Figure 5:
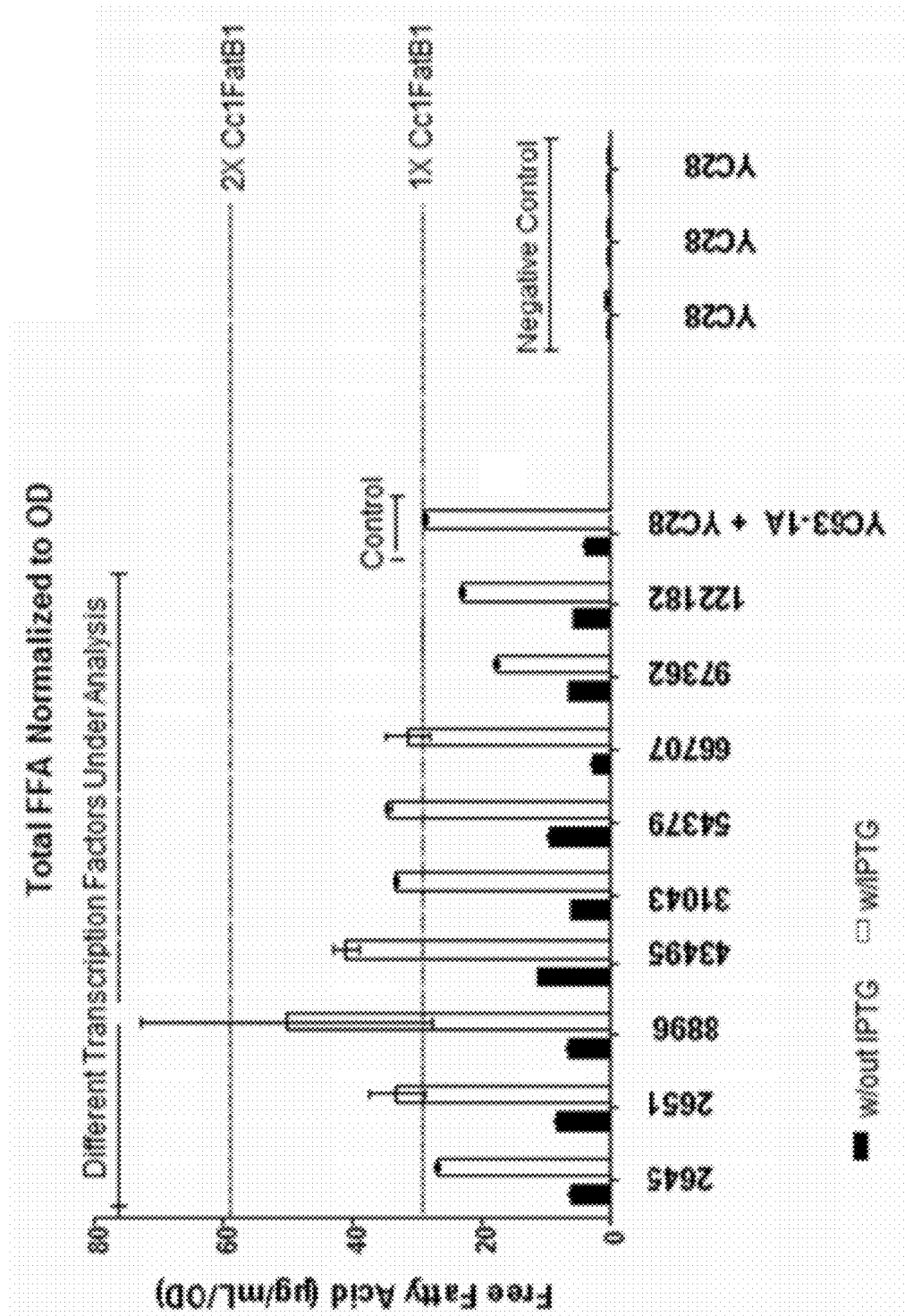

FIG. 5: Graph depicting the amount of free fatty acids per OD unit produced by the *Synechocystis* 6803 strains containing putative transcription factor genes provided in FIG. 4. The data provided in FIG. 4 is normalized for cell density to give the total production capabilities on a per cell basis.

DETAILED DESCRIPTION

Fatty acid synthesis in bacteria is an intricate metabolic pathway involving various intermediate compounds, enzymes and metabolic regulators. The fatty acid biosynthesis (FAB) pathway utilizes various enzymes including, but not limited to, acetyl-CoA carboxylase ("Accase" or AccABCD), malonyl-CoA-ACP transacylase (FabD), beta-ketoacyl-ACP synthase III (FabH), beta-ketoacyl-ACP reductase (FabZ, FabG), beta-hydroxyacyl-ACP dehydrase (FabA, FabZ), enoyl-ACP reductase I (FabI), enoyl-ACP reductase I (FabK), enoyl-ACP reductase III (FabL), beta-ketoacyl-ACP synthase I (FabB), beta-ketoacyl-ACP synthase II (FabF), beta-ketoacyl-ACP synthase III (FabH, also called acetoacetyl-ACP synthase), and 3-enoyl-ACP isomerase (FabM) (herein referred to as FAB enzymes).

Figure 1:
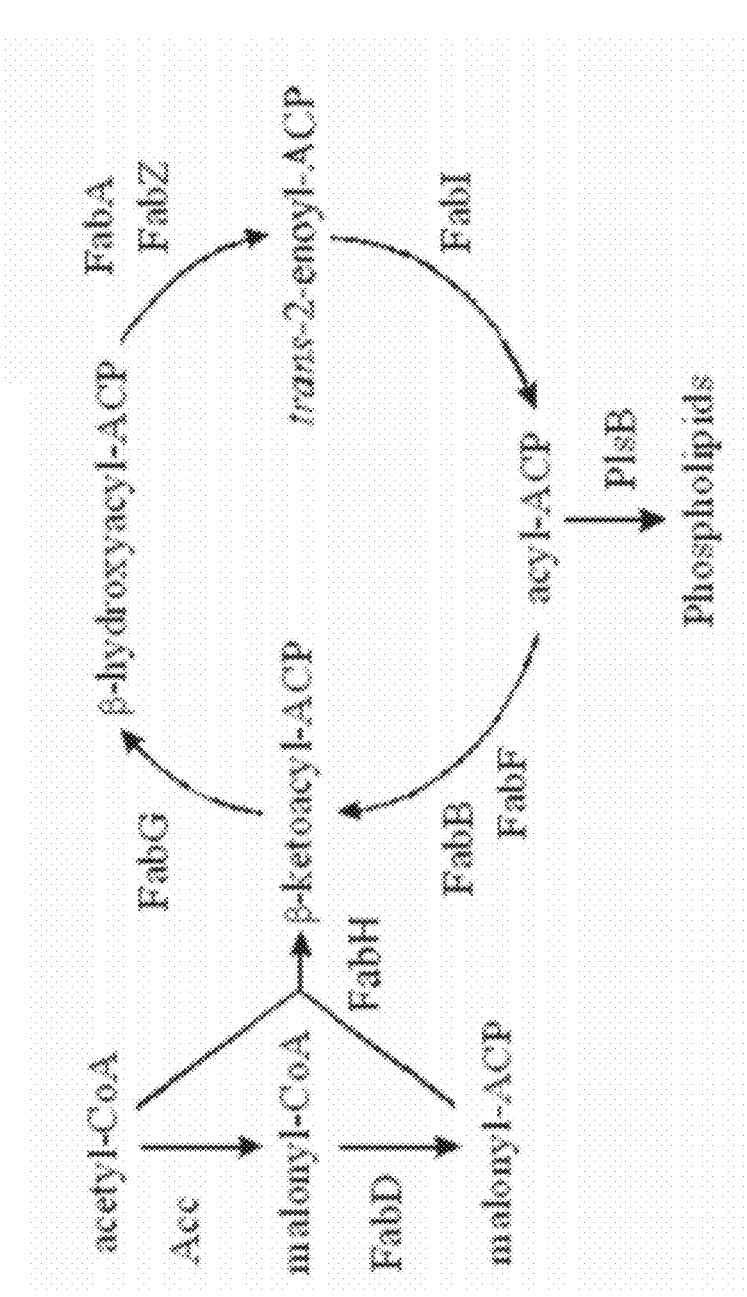
FIG. 1: Summary diagram of the fatty acid biosynthesis pathway in cyanobacteria.

FIG. 1 depicts the FAB pathway, starting from the central metabolite acetyl-CoA, using *E. coli* "Fab" gene designations. In the reaction shown in FIG. 1, fatty acid biosynthesis is initiated by acetyl-CoA being carboxylated to malonyl-CoA, catalyzed by acetyl-CoA carboxylase, or AccABCD. Malonyl-CoA is converted to malonyl-ACP, catalyzed by malonyl-CoA-ACP transacylase (FabD). The elongation cycle is initiated by condensation of malonyl-ACP with acetyl-ACP, catalyzed by a beta-ketoacyl-ACP synthase III (e.g., FabH). The β-ketoacyl-ACP (3-ketoacyl-ACP) from the FabH reaction is reduced to a β-hydroxyacyl-ACP (3-hydroxyacyl-ACP) by 3-ketoacyl-ACP reductase (e.g. FabG). The β-hydroxyacyl-ACP is then acted on by a β-hydroxyacyl-ACP dehydratase (e.g. FabA, FabZ) to form trans-2-enoyl-ACP, which in turn is reduced by enoyl-ACP reductase (e.g. Fab I, Fab K, FabL) to result in the 2 carbon-elongated acyl-ACP product. Subsequent cycles are initiated by a β-ketoacyl-ACP synthase I or II (e.g., FabB or FabF) catalyzed condensation of malonyl-ACP with acyl-ACP. The cycles of condensation, reduction, dehydration, and reduction are repeated, with each cycle adding two carbons from malonyl-ACP, until the acyl chain is cleaved from ACP by a thioesterase, such as FatA or FatB, to form free fatty acid or transferred to another molecule (e.g. glycerol 3-phosphate) by a transacylase.

As provided herein, engineering a production host for the production of fatty acids or fatty acids derivatives, can include transforming the host microorganism with a nucleic acid molecule that encodes a transcription factor domain protein that can be expressed in the host microorganism to increase production levels of lipids, fatty acids, or biomolecules derived from or incorporating fatty acids, including, for example, fatty alcohols, fatty acid esters, wax esters, hydrocarbons, and triglycerides.

Transcription factors are proteins that regulate the expression of specific gene(s) and/or operons. In one aspect, they regulate DNA transcription by recognizing certain DNA sequences and establishing appropriate interactions between the components of the transcription machinery. In other aspects, transcription factors can be proteins that interact with one or more DNA binding proteins to increase or reduce the binding or transcription-promoting activity of the DNA binding protein.

As used herein, the term "transcription factor domain protein" refers to any polypeptide that includes a transcription factor domain. Transcription factor domains include, but are not limited to, (1) DNA binding domains (DBD); (2) signal-sensing domains; and (3) transactivation domains. A transcription factor domain protein as described herein may function alone or with other proteins in a complex, by promoting (as an activator), or blocking (as a repressor) the recruitment of RNA polymerase to specific genes involved in the fatty acid lipid biosynthesis pathway so as to modulate expression of the specific gene.

Transcription factors can be classified based on the similarity of their conserved domains (e.g. Stegmaier (2004) *Genome Inform.* 15, 276-86). The transcription factor domain proteins of the invention may have one or more domains conserved across transcription factors (i.e. conserved domain). A "conserved domain" as used herein, refers to a protein domain within a transcription factor family that exhibits a high degree of sequence identity and structural similarity, to a DNA binding domain, signal-sensing domain, or transactivation domain of any characterized transcription factor. Conserved domains can be identified by searching the Conserved Domain Database (CDD) of annotated sequence alignment models at the National Center for Biotechnology Information website (available at ncbi.nlm.nih.gov/Structure/cdd/wrpsb.cgi). See Marchler-Bauer A et al. (2011) *Nucleic Acids Res.* 39(D): 225-9. Amino acid sequences having lesser degrees of sequence or structural homology but comparable biological activity (i.e. comparable to the biological activity of the transcription factor domain proteins described herein) to those disclosed herein are considered to be equivalents. Assays to demonstrate and measure the activity of any particular transcription factor are well known (e.g. Weisner (2002) *Nucl. Acids Res.* (2002) 30, e80). In some embodiments of the present invention, the biological activity of the transcription factor domain proteins of the invention is to increase the expression of one or more of the proteins in the FAB pathway including, but not limited to, AccABCD, FabD, FabH, FabG, FabA, FabZ, FabI, FabK, FabL, FabM, FabB, and/or FabF, or their homologs.

Alternatively or in addition, transcription factor domain proteins can be identified based on the structural domains that recur among these proteins. The structural characteristics can be characteristic of DNA binding domains, signal-sensing domain proteins, or transactivation domains of transcription regulatory proteins. Many protein domains characteristic of transcription factors are present in the pfam database, in which proteins are grouped by family based on structural features. "Pfam" is a large collection of protein domains and protein families maintained by the Pfam Consortium and available at several sponsored world wide web sites, including: pfam.sanger.ac.uk/ (Welcome Trust, Sanger Institute); pfam.sbc.su.se/ (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 26.0 November 2011, 13672 families) based on the UniProtKB protein. Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) Nucleic Acids Research 26, 263-266; Bateman (2004) *Nucleic Acids Research* 32, Database Issue, D138-D141; Finn (2006) *Nucleic Acids Research* Database Issue 34, D247-251; Finn (2010) *Nucleic Acids Research* Database Issue 38, D211-222). By accessing the Pfam database, for example, using any of the above-reference websites, protein sequences can be queried against the HMMs using HMMER homology search software (e.g. HMMER2, HMMER3, or a higher version, hmmer.janelia.org/). Significant matches that identify a queried protein as being in a Pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

Transcription factor domain proteins in some embodiments include proteins that when queried against the Pfam database have a match with a Pfam family that belongs to the helix-turn-helix Pfam clan, a response regulator Pfam, or a histidine kinase Pfam, in which the bit score for inclusion in the family is greater than the gathering cutoff for the Pfam.

For example, considered herein are genes encoding proteins of prokaryotes that include transcription factor domains such as but not limited to, prokaryotic proteins that may belong to the helix-turn-helix (HTH) clan of DNA binding domain proteins (Pfam clan CL0123), including, as nonlimiting examples, members of the arsR family (PF01022), the crp family (Pfam PF00325), the iron dependent repressor metal binding and dimerization domain family (Pfam PF02742), the lad family (Pfam PF00356), the HTH 10 family (Pfam PF04967), the HTH 14 family (Pfam PF12323), the rpiR family (Pfam PF01418), the AraC family (Pfam PF00165), the Mga family (Pfam PF05043), the FeoC family (Pfam PF09012), the luxR family (Pfam PF00196), the FaeA family (Pfam PF04703), the Trp Repressor family (Pfam PF01371) the MerR family (Pfam PF00376), the TetR family (Pfam PF00440), as well as the winged helix families of transcription factor domains.

The winged helix families of transcriptional regulators, which fall within the helix-turn-helix clan of protein families, include, as nonlimiting examples, the AsnC trans regulator family (Pfam PF01037), the Arg repressor C family (Pfam PF02863), the DeoR-like family (Pfam PF08220), gntR family (Pfam PF00392), the LexA family Pfam (PF01726), the Hx1R family (Pfam PF01638), the HTH 1 lysR family (Pfam PF00126), the ferric uptake regulator (FUR) family (Pfam PF01475), the MarR family (Pfam PF01047), and the Rff2 family (Pfam PF02082).

Further considered for use in the invention are nucleic acid molecules encoding proteins having transcription factor domains in which the proteins are members of two-component signaling systems (West and Stock (2001) *Trends in Biochemical Science* 26: 369-376). A transcription factor domain protein can be, for example, a protein that includes a histidine kinase domain (e.g. a protein that is a member of Pfam PF07730, PF07536, PF00512, PF07568, or PF02518), or a protein that includes a response regulator domain, for example, a protein that recruits to Pfam PF00072 or Pfam PF06490. Two component gene regulatory systems are common in prokaryotes, where the histidine kinase protein phosphorylates its partner response regulator protein in response to an environmental or metabolic signal. The response regulator protein is a DNA binding protein that controls transcription of particular genes.

A transcription factor for use in upregulating fatty acid or lipid biosynthesis may be a transcription factor identified by sequence analysis and may be a naturally-occurring open reading frame sequence that has not been previously characterized as a transcription factor. In some embodiments, genes encoding transcription factor domain proteins may be found in their native genomes located proximal to fatty acid or lipid biosynthesis genes, for example, located on the same strand and separated by no more than three genes from a putative fatty acid or lipid biosynthesis gene, or if on the opposite strand from a putative fatty acid or lipid biosynthesis gene, and with no more than one possible gene intervening between the transcription factor domain-containing ORF and fatty acid or lipid biosynthesis gene. In some embodiments, the nucleotide sequence encoding the transcription factor domain protein gene has at least 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to any of nucleotide sequences disclosed herein as encoding polypeptides having transcription factor domains.

A transcription factor domain protein may act by itself or in combination with at least one other polypeptide to regulate gene expression levels. In one example, a response regulator transcription factor domain protein acts in combination with a histidine kinase transcription factor domain protein to regulate gene expression. A transcription factor domain protein as provided herein typically increases expression levels. However, in some cases a transcription factor domain protein as provided herein may suppress expression of a particular gene or pathway.

Nucleic Acid Molecules and Polypeptides

The novel transcription factor domain proteins (or other regulators) described herein were discovered by a novel bioinformatics approach. Specifically, the inventors hypothesized that open reading frames encoding proteins having transcription factor domains that are located in close proximity to fatty acid or lipid biosynthetic gene(s) may be transcription factors that regulate the expression of fatty acid biosynthesis gene(s). The regulatory effects of the expressed transcription factor domain protein genes may be positive (upregulation) or negative (repression). Identifying either activity can be useful for increasing cellular fatty acid or lipid biosynthesis. As described in Example 1, (a) an extensive list of protein families with functions associated with transcriptional regulation, and (b) a list of protein families with functions associated with fatty acid and lipid biosynthesis, were compiled. Next, all sequences recruiting to these protein families were retrieved from proprietary databases containing cyanobacterial genome sequences and sequences from metagenomic libraries, and finally the two separate lists of accession numbers (in which the accession numbers correspond to genome positions) were compared to ascertain gene neighborhood or proximity between the two classes of genes. Using this approach, open reading frames encoding polypeptides having transcription factor domains were identified from six cyanobacterial genomes and two metagenomes (Table 1). Amino acid sequences of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 and SEQ ID NO:20 represent those polypeptides initially identified as having potential transcription factor domains.

The invention provides an isolated nucleic acid molecule comprising a nucleic acid sequence encoding a polypeptide comprising an amino acid sequence having at least 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:2, SEQ ID NO:4, SEQ ID NO:6, SEQ ID NO:10, SEQ ID NO:12, SEQ ID NO:14, SEQ ID NO:16, or SEQ ID NO:18. Also encompassed are isolated nucleic acid molecules comprising nucleic acid sequences encoding polypeptides that include amino acid sequences having at least 60%, 65%, 70%, 75%, 80%, 85%, 86%, 87%, 88%, 89%, 90%, 91%, 92%, 93%, 94%, 95%, 96%, 97%, 98%, 99% or 100% sequence identity to functional fragments of the referenced polypeptides. The terms "peptide," "polypeptide" and "protein" are used interchangeably herein, although "peptide" may be used to refer to a polypeptide having no more than about 100 amino acids, or no more than about 60 amino acids. The nucleic acid sequences according to some embodiments of the present invention encode cyanobacterial transcription factor domain proteins.

For example, an isolated or recombinant nucleic acid molecule as provided herein can include a sequence that encodes a polypeptide that includes an amino acid sequence that has at least 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:2 or a functional fragment thereof. Additionally, an isolated or recombinant nucleic acid molecule having homology to SEQ ID NO:2 can be a polypeptide that recruits to Pfam PF02518. An isolated or recombinant nucleic acid molecule as provided herein can include a sequence that encodes a polypeptide that includes an amino acid sequence that has at least 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:2 or a functional fragment thereof, where expression of the nucleic acid sequence in a cyanobacterial host can result in a higher level of fatty acid, fatty acid derivative, or lipid being produced by a culture of the cyanobacterium than is produced is a culture of a control cyanobacterium that does not express a nucleic acid sequence that encodes a polypeptide that includes an amino acid sequence that has at least 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:2 or a functional fragment thereof. For example, an isolated or recombinant nucleic acid molecule as provided herein can include a sequence that encodes a polypeptide that includes an amino acid sequence that has at 85% sequence identity to SEQ ID NO:2 or a functional fragment thereof, or at least 90% or at least 95% sequence identity to SEQ ID NO:2 or a functional fragment thereof.

In further examples, an isolated or recombinant nucleic acid molecule as provided herein can include a sequence that encodes a polypeptide that includes an amino acid sequence that has at least 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:4 or a functional fragment thereof. Additionally, an isolated or recombinant nucleic acid molecule having homology to SEQ ID NO:4 can be a polypeptide that recruits to Pfam PF00072. An isolated or recombinant nucleic acid molecule as provided herein can include a sequence that encodes a polypeptide that includes an amino acid sequence that has at least 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:4 or a functional fragment thereof, where expression of the nucleic acid sequence in a cyanobacterial host can result in a higher level of fatty acid, fatty acid derivative, or lipid being produced by a culture of the cyanobacterium than is produced is a culture of a control cyanobacterium that does not express a nucleic acid sequence that encodes a polypeptide that includes an amino acid sequence that has at least 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:4 or a functional fragment thereof. For example, an isolated or recombinant nucleic acid molecule as provided herein can include a sequence that encodes a polypeptide that includes an amino acid sequence that has at 85% sequence identity to SEQ ID NO:4 or a functional fragment thereof, or at least 90% or at least 95% sequence identity to SEQ ID NO:4 or a functional fragment thereof.

In additional examples, an isolated or recombinant nucleic acid molecule as provided herein can include a sequence that encodes a polypeptide that includes an amino acid sequence that has at least 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:6 or a functional fragment thereof. Additionally, an isolated or recombinant nucleic acid molecule having homology to SEQ ID NO:6 can be a polypeptide that recruits to Pfam PF00440. An isolated or recombinant nucleic acid molecule as provided herein can include a sequence that encodes a polypeptide that includes an amino acid sequence that has at least 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:6 or a functional fragment thereof, where expression of the nucleic acid sequence in a cyanobacterial host can result in a higher level of fatty acid, fatty acid derivative, or lipid being produced by a culture of the cyanobacterium than is produced is a culture of a control cyanobacterium that does not express a nucleic acid sequence that encodes a polypeptide that includes an amino acid sequence that has at least 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO:6 or a functional fragment thereof. For example, an isolated or recombinant nucleic acid molecule as provided herein can include a sequence that encodes a polypeptide that includes an amino acid sequence that has at 85% sequence identity to SEQ ID NO:6 or a functional fragment thereof, or at least 90% or at least 95% sequence identity to SEQ ID NO:6 or a functional fragment thereof.

In further examples, an isolated or recombinant nucleic acid molecule as provided herein can include a sequence that encodes a polypeptide that includes an amino acid sequence that has at least 85%, 86%, 87%, 88%, 89%, 90%, 91%, 92%, 93%, 94%, 95%, 96%, 97%, 98%, 99% or 100% sequence identity to SEQ ID NO:10 or a functional fragment thereof. Additionally, an isolated or recombinant nucleic acid molecule having homology to SEQ ID NO:10 can be a polypeptide that recruits to Pfam PF00216. An isolated or recombinant nucleic acid molecule as provided herein can include a sequence that encodes a polypeptide that includes an amino acid sequence that has at least 85%, 86%, 87%, 88%, 89%, 90%, 91%, 92%, 93%, 94%, 95%, 96%, 97%, 98%, 99% or 100% sequence identity to SEQ ID NO:10 or a functional fragment thereof, where expression of the nucleic acid sequence in a cyanobacterial host can result in a higher level of fatty acid, fatty acid derivative, or lipid being produced by a culture of the cyanobacterium than is produced is a culture of a control cyanobacterium that does not express a nucleic acid sequence that encodes a polypeptide that includes an amino acid sequence that has at least 85%, 86%, 87%, 88%, 89%, 90%, 91%, 92%, 93%, 94%, 95%, 96%, 97%, 98%, 99% or 100% sequence identity to SEQ ID NO:10 or a functional fragment thereof. For example, an isolated or recombinant nucleic acid molecule as provided herein can include a sequence that encodes a polypeptide that includes an amino acid sequence that has at 85% sequence identity to SEQ ID NO:10 or a functional fragment thereof, or at least 90% or at least 95% sequence identity to SEQ ID NO:10 or a functional fragment thereof.

In additional examples, an isolated or recombinant nucleic acid molecule as provided herein can include a sequence that encodes a polypeptide that includes an amino acid sequence that has at least 80%, 85%, 86%, 87%, 88%, 89%, 90%, 91%, 92%, 93%, 94%, 95%, 96%, 97%, 98%, 99% or 100% sequence identity to SEQ ID NO:12 or a functional fragment thereof. Additionally, an isolated or recombinant nucleic acid molecule having homology to SEQ ID NO:12 can be a polypeptide that recruits to Pfam PF00376. An isolated or recombinant nucleic acid molecule as provided herein can include a sequence that encodes a polypeptide that includes an amino acid sequence that has at least 80%, 85%, 86%, 87%, 88%, 89%, 90%, 91%, 92%, 93%, 94%, 95%, 96%, 97%, 98%, 99% or 100% sequence identity to SEQ ID NO:12 or a functional fragment thereof, where expression of the nucleic acid sequence in a cyanobacterial host can result in a higher level of fatty acid, fatty acid derivative, or lipid being produced by a culture of the cyanobacterium than is produced is a culture of a control cyanobacterium that does not express a nucleic acid sequence that encodes a polypeptide that includes an amino acid sequence that has at least 80%, 85%, 86%, 87%, 88%, 89%, 90%, 91%, 92%, 93%, 94%, 95%, 96%, 97%, 98%, 99% or 100% sequence identity to SEQ ID NO:12 or a functional fragment thereof. For example, an isolated or recombinant nucleic acid molecule as provided herein can include a sequence that encodes a polypeptide that includes an amino acid sequence that has at 85% sequence identity to SEQ ID NO:12 or a functional fragment thereof, or at least 90% or at least 95% sequence identity to SEQ ID NO:12 or a functional fragment thereof.

In yet further examples, an isolated or recombinant nucleic acid molecule as provided herein can include a sequence that encodes a polypeptide that includes an amino acid sequence at least 99% identical to SEQ ID NO:14 or SEQ ID NO:16 or to a functional fragment of SEQ ID NO:14 or SEQ ID NO:16. Additionally, an isolated or recombinant nucleic acid molecule having homology to SEQ ID NO:14 or SEQ ID NO:16 can be a polypeptide that recruits to Pfam PF00072. An isolated or recombinant nucleic acid molecule as provided herein can include a sequence that encodes a polypeptide that includes an amino acid sequence at least 99% identical to SEQ ID NO:14 or SEQ ID NO:16 or to a functional fragment of SEQ ID NO:14 or SEQ ID NO:16, where expression of the nucleic acid sequence in a cyanobacterial host can result in a higher level of fatty acid, fatty acid derivative, or lipid being produced by a culture of the cyanobacterium than is produced is a culture of a control cyanobacterium that does not express a nucleic acid sequence that encodes a polypeptide that includes the amino acid sequence having at least 99% identity to SEQ ID NO:14 or SEQ ID NO:16 or to a functional fragment of SEQ ID NO:14 or SEQ ID NO:16.

In other examples, an isolated or recombinant nucleic acid molecule as provided herein can include a sequence that encodes a polypeptide that includes an amino acid sequence at least 95% identical to SEQ ID NO:18 or to a functional fragment of SEQ ID NO:18. Additionally, an isolated or recombinant nucleic acid molecule having homology to SEQ ID NO:18 can be a polypeptide that recruits to Pfam PF00072. For example, an isolated or recombinant nucleic acid molecule as provided herein can include a sequence that encodes a polypeptide that includes an amino acid sequence that has at 95% sequence identity to SEQ ID NO:18 or a functional fragment thereof, or at least 97% or at least 99% sequence identity to SEQ ID NO:18 or a functional fragment thereof.

The present invention also includes an isolated or recombinant nucleic acid molecule comprising a nucleic acid sequence having at least about 50%, 60%, 65%, 70%, 75%, 80%, or 85%, for example at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity with the nucleic acid sequence of SEQ ID NO:1, SEQ ID NO:3, SEQ ID NO:5, SEQ ID NO:9, SEQ ID NO:11, SEQ ID NO:13, SEQ ID NO:15, or SEQ ID NO:17. The isolated or recombinant nucleic acid molecules of the invention may encode, for example, polypeptides than include amino acid sequences having at least 70% identity to SEQ ID NO:2, at least 65% identity to SEQ ID NO:4, at least 60% identity to SEQ ID NO:6, at least 85% identity to SEQ ID NO:10, at least 80% identity to SEQ ID NO:12, at least 99% identity to SEQ ID NO:14, at least 99% identity to SEQ ID NO:16, or at least 90% identity to SEQ ID NO:18, respectively.

As used herein, an "isolated" nucleic acid molecule or nucleotide sequence is intended to mean a nucleic acid molecule or nucleotide sequence that is not flanked by nucleotide sequences normally flanking the gene or nucleotide sequence (as in genomic sequences) in the organism from which the nucleic acid molecule or nucleotide sequence is derived and/or has been completely or partially removed from its native environment (e.g. a cell, tissue). For example, nucleic acid molecules that have been removed or purified from cells are considered isolated. In some instances, the isolated material will form part of a composition (for example, a crude extract containing other substances), buffer system or reagent mix. In other circumstances, the material may be purified to near homogeneity, for example as determined by PAGE or column chromatography such as HPLC. Thus, an isolated nucleic acid molecule or nucleotide sequence can includes a nucleic acid molecule or nucleotide sequence which is synthesized chemically, using recombinant DNA technology or using any other suitable method. To be clear, a nucleic acid contained in a vector would be included in the definition of "isolated" as used herein. Also, isolated nucleotide sequences include partially or substantially purified nucleic acids in solution. "Purified," on the other hand is well understood in the art and generally means that the nucleic acid molecules are substantially free of cellular material, cellular components, chemical precursors or other chemicals beyond, perhaps, buffer or solvent. "Substantially free" is not intended to mean that other components beyond the novel nucleic acid molecules are undetectable. The nucleic acid molecules of the present invention may be isolated or purified. Both in vivo and in vitro RNA transcripts of a DNA molecule of the present invention are also encompassed by "isolated" nucleotide sequences.

Expression of an isolated or recombinant nucleic acid molecule encoding a polypeptide comprising an amino acid sequence having at least 60%, 65%, 70%, 75%, 80%, 85%, 86%, 87%, 88%, 89%, 90%, 91%, 92%, 93%, 94%, 95%, 96%, 97%, 98%, 99% or 100% identity to the amino acid sequence of SEQ ID NO:2, SEQ ID NO:4, SEQ ID NO:6, SEQ ID NO:10, SEQ ID NO:12, SEQ ID NO:14, or SEQ ID NO:16 or to a functional fragment thereof, or at least 90%, 91%, 92%, 93%, 94%, 95%, 96%, 97%, 98%, 99% or 100% identity to the amino acid sequence of SEQ ID NO:2, SEQ ID NO:4, SEQ ID NO:6, SEQ ID NO:10, SEQ ID NO:12, SEQ ID NO:14, or SEQ ID NO:16 or to a functional fragment thereof, in a photosynthetic microorganism can result in higher level of a fatty acid, fatty acid derivative, or lipid being produced by the photosynthetic microorganism than is produced by a control photosynthetic microorganism cultured under the same conditions and identical to the transcription factor domain protein transformant in all respects, with the exception that the control microorganism does not express the isolated or recombinant nucleic acid molecule. Additionally, the invention encompasses deletion mutants of the transcription factor domain proteins where one or more amino acids have been deleted from the protein. In one embodiment, the polypeptide is 145, 144, 143, 142, 141, 140, 139, 138, 137, 136 residues or less with each peptide independently comprising an amino acid sequence at least 70%, 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:2. In another embodiment, the polypeptide is 546, 545, 544, 543, 542, 541, 540, 539, 538, 537 residues or less with each peptide independently comprising an amino acid sequence at least 65%, 70%, 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:4. In another embodiment, the polypeptide is 391, 390, 389, 388, 387, 386, 385, 384, 383, 382 residues or less with each peptide independently comprising an amino acid sequence at least 60%, 65%, 70%, 75%, 80%, 85%, 86%, 87%, 88%, 89%, 90%, 91%, 92%, 93%, 94%, 95%, 96%, 97%, 98%, 99% or 100% identical to the amino acid sequence of SEQ ID NO:6 In another embodiment, the polypeptide is 105, 104, 103, 102, 101, 100, 99, 98, 97, 96 residues or less with each peptide independently comprising an amino acid sequence at least 85%, 86%, 87%, 88%, 89%, 90%, 91%, 92%, 93%, 94%, 95%, 96%, 97%, 98%, 99% or 100% identical to the amino acid sequence of SEQ ID NO:10. In another embodiment, the polypeptide is 109, 108, 107, 106, 105, 104, 103, 102, 101, 100 residues or less with each peptide independently comprising an amino acid sequence at least 85%, 86%, 87%, 88%, 89%, 90%, 91%, 92%, 93%, 94%, 95%, 96%, 97%, 98%, 99% or 100% identical to the amino acid sequence of SEQ ID NO:12.

Percent identity or homology with respect to such sequences is defined herein as the percentage of amino acid or nucleotide residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology.

This application discloses and refers to nucleic acids and polypeptides by identifiers used in long-established and extensively referenced databases maintained by the National Center for Biotechnology Information (NCBI). Accession numbers are unique identifiers for a sequence record publicly available at the National Center for Biotechnology Information website (ncbi.nlm.nih.gov) maintained by the United States National Institutes of Health. Searching and obtaining nucleic acid or gene sequences or protein sequences based on Accession numbers and GI (gene identifier) numbers is well known in the arts of, e.g., cell biology, biochemistry, molecular biology, and molecular genetics.

Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e. the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e. the reward score for a pair of matching residues) to N (i.e. the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, the present invention also includes an isolated nucleic acid molecule comprising a nucleic acid sequence encoding a polypeptide comprising an amino acid sequence having the amino acid sequence at least about 60%, 65%, 70%, 75%, 80%, or 85%, for example at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity with the peptide sequence of SEQ ID NO:2, SEQ ID NO:4, SEQ ID NO:6, SEQ ID NO:10, SEQ ID NO:12, SEQ ID NO:14, or SEQ ID NO:16; fragments thereof comprising a consecutive sequence of at least about 50, for example at least about 75, at least about 100, at least about 125, at least about 150 or more amino acid residues of the entire protein; amino acid sequence variants of such sequences, wherein at least one amino acid residue has been inserted N- and/or C-terminal to, and/or within, the disclosed sequence(s) which contain(s) the insertion and substitution; amino acid sequence variants of the disclosed sequence, and/or their fragments as defined above. Contemplated variants can additionally or alternately include those containing predetermined mutations by, e.g. homologous recombination or site-directed or PCR mutagenesis, and the corresponding proteins of other species, including, but not limited to, those described herein, the alleles or other naturally occurring variants of the family of proteins which contain the insertion and substitution; and/or derivatives wherein the protein has been covalently modified by substitution, chemical, enzymatic, or other appropriate means with a moiety other than a naturally occurring amino acid which contains the insertion and substitution (for example, a detectable moiety such as an enzyme).

The nucleic acid molecules disclosed herein include, but are not limited to, nucleic acid molecules that encode transcription factor domain proteins that are members of Pfam helix-turn-helix clan CL0123, such as for example, polypeptides that are members of Pfam PF01022, PF00325, PF02742, PF00356, PF04967, PF12323, PF01418, PF00165, PF05043, PF09012, PF00196, PF0470, PF01371, PF00376, PF00440, PF00072, PF01037, PF02863, PF08220, PF00392, PF01726, PF01638, PF00126, PF01475, PF01047, or PF02082. In some embodiments, a nucleic acid molecule of the invention encodes a polypeptide that recruits to Pfam PF01037.

In further examples, the nucleic acid molecules disclosed herein include, but are not limited to, nucleic acid molecules that encode transcription factor domain proteins that are members of a histidine kinase Pfam such as for example, PF07730, PF07536, PF00512, PF07568, or PF02518. In yet further embodiments, a nucleic acid molecule as disclosed herein can include a response regulator receiver domain, and can be included in Pfam PF00072 or PF06490 with a bit score at least as high as the gathering cutoff for these Pfams when queried against the Pfam database.

For example, a recombinant transcription factor gene of a microorganism as provided herein can encode a protein having an E-value parameter of 3E-5 or less, or having a bit score higher than the gathering cutoff when queried using the Pfam Profile HMM (for example using FastMM version 1.2, or HMMER version 2.0 (HMMER2) (or a higher version of either of these) for any of the aforementioned Pfams, including, for example, Pfam PF00072, Pfam PF02518, Pfam PF00440, Pfam PF00216, and Pfam PF00376.

The invention also encompasses variations of the nucleotide sequences of the invention, such as those encoding functional fragments or variants of the polypeptides as described herein. Such variants can be naturally-occurring, or non-naturally-occurring, such as those induced by various mutagens and mutagenic processes. Intended variations include, but are not limited to, addition, deletion, and substitution of one or more nucleotides which can result in conservative or non-conservative amino acid changes, including additions and deletions.

Additionally, variants of the transcription factor domain proteins described herein having at least about 75%, 80%, 85%, 90%, or 95% identity to SEQ ID NO:2, SEQ ID NO:4, SEQ ID NO:6, SEQ ID NO:10, SEQ ID NO:12, SEQ ID NO:14, or SEQ ID NO:16, retain their ability to regulate a metabolic pathway in a photosynthetic microorganism, at least partially, where expression of the transcription factor domain protein results in increased production of a fatty acid, fatty acid derivative, or lipid. In additional embodiments, the variants described herein are functional and capable of regulating a FAB pathway, such as fatty acid and lipid biosynthesis pathways. For example, variants of the transcription factor domain proteins described herein having at least about 75%, 80%, 85%, 90%, or 95% identity to SEQ ID NO:2, SEQ ID NO:4, SEQ ID NO:6, SEQ ID NO:8, SEQ ID NO:10, or SEQ ID NO:12 or at least about 90% or 95% identity to SEQ ID NO:18, when expressed in a host cell, still retain their ability to enhance expression of one or more of the proteins in the FAB pathway including, but not limited to, an acetyl CoA carboxylase gene (e.g. Accase, including, for example AccA, AccB, AccC, and/or AccD), malonyl-CoA-ACP transacylase (e.g. FabD), a beta ketoacyl-ACP synthase (e.g. FabH, FabF, FabB), a 3-ketoacyl-ACP reductase (e.g. FabG), a beta hydroxyacyl dehyrase (e.g. FabA), and/or an enoyl-ACP reductase (e.g. FabI, FabK, FabL). Alternatively or in addition, expression of the polypeptide encoded by the nucleic acid molecule in a photosynthetic microorganism, such as but not limited to a cyanobacterium, can results in elevated production of a lipid, fatty acid, or fatty acid derivative by the microorganism.

For example, expression of transcription factor domain proteins described herein having at least about 75%, 80%, 85%, 90%, or 95% identity to SEQ ID NO:2, SEQ ID NO:4, SEQ ID NO:6, SEQ ID NO:10, SEQ ID NO:12, SEQ ID NO:14, SEQ ID NO:16 in a transgenic microorganism, such as but not limited to a transgenic cyanobacterium, can result in production of at least about 5%, 8%, 10%, 15%, 20%, 30%, 40%, 50%, 60%, 70%, 80%, 90%, 100%, 150%, or 200% more than the amount of the fatty acid or fatty acid derivative produced by a microorgansim not including the exogenous gene encoding the transcription factor domain protein, but identical in all other respects. Additionally or alternately, the amount of the fatty acid or fatty acid derivative produced by the transgenic microorganism that includes an exogenous transcription factor domain protein gene as described herein can be at least about 290 mg per liter of culture.

Specifically included herein are nucleic acid molecules encoding conservative variants of the transcription factor domain proteins disclosed herein. A "conservative variant" of a polypeptide is a polypeptide having one or more conservative amino acid substitutions with respect to the reference polypeptide, in which the activity (e.g. effect on transcription), affinity for co-regulators or ligands, or DNA-binding affinity of the polypeptide does not substantially differ from that of the reference polypeptide.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained.

A substitution, insertion, or deletion can be said to adversely affect the protein when the altered sequence substantially inhibits a biological function associated with the protein. For example, included herein are variants of transcription factor domain proteins in which the DNA binding activity of the variant or increase in transcription or product levels of a transgenic microorganism transformed with a gene encoding the variant is not reduced by more than 5% with respect to the transcription factor domain protein from which the variant is derived, or in which the production of free fatty acids by a host microorganism that expresses the transcription factor domain protein variant is not less than 95% of the production of free fatty acids by the same microorganism expressing the transcription factor domain protein from which the variant was derived, in which the variant and transcription factor domain protein are expressed under the same conditions using the same expression construct configurations.

In some further embodiments, the nucleotide sequences of the genes encoding the transcription factor domain proteins of the invention may be mutated so as to increase their biological activity and/or enhance their binding specificity so as to increase fatty acid, fatty acid derivative, or lipid production or enhance expression of one or more of the proteins in the FAB pathway including, but not limited to, an acetyl CoA carboxylase gene (e.g. Accase, including, for example AccA, AccB, AccC, and/or AccD), malonyl-CoA-ACP transacylase (e.g. FabD), a beta ketoacyl-ACP synthase (e.g. FabH, FabF, FabB), a 3-ketoacyl-ACP reductase (e.g. FabG), a beta hydroxyacyl dehydrase (e.g. FabA), and/or an enoyl-ACP reductase (e.g. FabI, FabK, FabL).

Such mutations include but are not limited to, codon optimization to enhance expression of the wild-type sequence in transgenic cyanobacteria (e.g. Burgess-Brown (2008) *Protein Expr. Purif.* 59, 94-102) and mutations resulting from site specific mutagenesis to alter the amino acid sequence of the transcription factor domain protein. Such alteration in amino acid sequence can increase the biological activity and/or enhance the specificity of the transcription factor domain protein in one or more species of cyanobacteria.

A given nucleic acid sequence may be modified, for example, according to standard mutagenesis or artificial evolution or domain swapping methods to produce modified sequences. Accelerated evolution methods are described, e.g. by Stemmer (1994) *Nature* 370, 389-391, and Stemmer (1994) *Proc. Natl. Acad. Sci. USA* 91, 10747-10751. Chemical or enzymatic alteration of expressed nucleic acids and polypeptides can be performed by standard methods. For example, sequence can be modified by addition of phosphate groups, methyl groups, lipids, sugars, peptides, organic or inorganic compounds, by the inclusion of modified nucleotides or amino acids, or the like. Further the transcription factor domain protein ORF may be derived from a collection of transcripts, such as a cDNA library, and the sequence of the transcript may be unknown.

The "nucleic acids" or "nucleic acid molecules" of the invention can be DNA or RNA, for example, mRNA. The nucleic acid molecules can be double-stranded or single-stranded; single stranded RNA or DNA can be the coding, or sense, strand or the non-coding, or antisense, strand. In particular, the nucleic acids may encode any polypeptide of the invention, including, but not limited to, the fusion proteins of the present invention. For example, the nucleic acids of the invention include polynucleotide sequences that encode glutathione-S-transferase (GST) fusion protein, poly-histidine (e.g. $His_6$), poly-HN, poly-lysine, hemagglutinin, HSV-Tag and at least a portion of HIV-Tat. If desired, the nucleotide sequence of the isolated nucleic acid can include additional non-coding sequences such as non-coding 3' and 5' sequences (including regulatory sequences, for example).

The invention described herein also relates to fragments of the isolated nucleic acid molecules described herein encompassing a portion of a nucleotide sequence described herein which is from at least about 20 contiguous nucleotides to at least about 50 contiguous nucleotides or longer in length. Such fragments may be useful as probes and primers. In particular, primers and probes may selectively hybridize to the nucleic acid molecule encoding the polypeptides described herein. For example, fragments which encode polypeptides that retain activity, as described below, are particularly useful.

The invention also provides nucleic acid molecules that hybridize under high stringency hybridization conditions, such as for selective hybridization, to the nucleotide sequences described herein (e.g. nucleic acid molecules which specifically hybridize to a nucleotide sequence encoding polypeptides described herein and encode a modified growth factor isooherin). Hybridization probes include synthetic oligonucleotides which bind in a base-specific manner to a complementary strand of nucleic acid. Suitable probes include polypeptide nucleic acids, as described in Nielsen (1991) *Science*, 254, 1497-1500.

Such nucleic acid molecules can be detected and/or isolated by specific hybridization e.g. under high stringency conditions. "Stringency conditions" for hybridization is a term of art that refers to the incubation and wash conditions, e.g. conditions of temperature and buffer concentration, which permit hybridization of a particular nucleic acid to a second nucleic acid; the first nucleic acid may be perfectly complementary, i.e. 100%, to the second, or the first and second may share some degree of complementarity, which is less than perfect, e.g. 60%, 75%, 85%, 95% or more. For example, certain high stringency conditions can be used which distinguish perfectly complementary nucleic acids from those of less complementarity.

"High stringency conditions", "moderate stringency conditions" and "low stringency conditions" for nucleic acid hybridizations are explained in Current Protocols in Molecular Biology (2011) John Wiley & Sons. The exact conditions which determine the stringency of hybridization depend not only on ionic strength, e.g. 0.2×SSC, 0.1×SSC of the wash buffers, temperature, e.g. 23° C., 42° C., 68° C., etc. and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause (1991) *Methods in Enzymology,* 200, 546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC, and 0.1% SDS at about 42° C. (moderate stringency conditions); and washing with 0.1×SSC at about 68° C. (high stringency conditions). Washing can be carried out using only one of these conditions, e.g. high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example.

Vectors

"Expression vector" or "expression construct" refers to a nucleic acid that has been generated via human intervention, including by recombinant means and/or direct chemical synthesis, with a series of specified nucleic acid "expression control elements" that permit transcription and/or translation of a particular nucleic acid in a host cell. The expression vector can be a plasmid, a part of a plasmid, a viral construct, a nucleic acid fragment, or the like, or a combination thereof. Typically, the expression vector can include a nucleic acid to be transcribed operably linked to a promoter in an "expression cassette". According to some preferable embodiments, the present invention can involve recombinant microorganisms transformed with an isolated nucleic acid molecule including a gene encoding a transcription factor domain protein as described herein under control of a heterologous promoter.

In some preferred embodiments of the invention, a gene encoding a transcription factor domain protein can be cloned into an expression vector for transformation into a cyanobacterium. The vector can include sequences that promote expression of any of the transcription factor domain proteins described herein such as a promoter. Alternatively, if the vector does not contain a promoter in operable linkage with the gene encoding the transcription factor domain protein, the gene can be transformed into the cells such that it becomes operably linked to an endogenous promoter by homologous recombination, site specific integration, and/or vector integration. "Operable linkage" is a functional linkage between two nucleic acid sequences, such as a control sequence (typically a promoter) and the linked sequence (typically a sequence that encodes a protein and/or functional RNA (e.g. an antisense RNA or dsRNA). A promoter is in operable linkage with an exogenous gene if it can mediate transcription of the gene. In some embodiments, nucleic acids encoding a transcription factor domain protein of the invention may be operably linked to a cyanobacterial-specific promoter.

In some embodiments, the present invention additionally or alternately provides recombinant microorganisms transformed with an isolated nucleic acid molecule including a nucleic acid sequence that is operably linked to one or more expression control elements. In some instances, it can be advantageous to express the transcription factor domain protein at a certain point during the growth of the transgenic microorganism, e.g. to minimize any deleterious effects on the growth of the transgenic organism and/or to maximize production of the fatty acid product of interest. In such instances, one or more exogenous genes introduced into the transgenic organism can be operably linked to an inducible promoter, i.e. a promoter that mediates transcription of an operably linked gene in response to a particular stimulus. An inducible promoter can be responsive to light or dark or high or low temperature, or can be responsive to specific compounds. The inducible promoter can be, for example, a lac promoter, a tet promoter (e.g. U.S. Pat. No. 5,851,796), a trp promoter, a hybrid promoter that includes either or both of portions of a tet, trp, or lac promoter. The promoter sequences can be from any organism, provided that it is functional in the host organism. Inducible promoters, as used in the constructs of the present invention, can use one or more portions or domains of the aforementioned promoters and/or other inducible promoters fused to at least a portion of a different promoter that can operate in the host organism, e.g. to confer inducibility on a promoter that operates in the host species.

A variety of promoters that function in cyanobacteria can be utilized, including, but not limited to, the lac, tac, and trc promoters, as well as derivatives such as but not limited to the trcE and trcY promoters that are inducible by the addition of isopropyl β-D-1-thiogalactopyranoside (IPTG), promoters that are naturally associated with transposon- or bacterial chromosome-borne antibiotic resistance genes (e.g. neomycin phosphotransferase, chloramphenicol acetyltransferase, spectinomycin adenyltransferase, or the like, or combinations thereof), promoters associated with various heterologous bacterial and native cyanobacterial genes, promoters from viruses and phages, synthetic promoters, or the like, or combinations thereof. Examples of such promoters include, but are not limited to, promoters isolated from cyanobacteria such as the following: secA (secretion; controlled by the redox state of the cell), rbc (Rubisco operon), psaAB (PS I reaction center proteins; light regulated), Pm, NtcA or glnA promoter, and psbA (Dl protein of PSII; light-inducible). Also considered are promoters regulated by nitrogen compounds, such as, for example, nar, ntc, nir, or nrt promoters. Also considered are pho or pst promoters regulated by phosphate and promoters regulated by metals, e.g., the nrs promoter (Liu and Curtis (2009) *Proc Natl Acad Sciences USA* 106: 21550-21554), or the petE promoter (Buikema and Haselkorn (2001) *Proc Natl Acad Sciences USA* 98: 2729-2734)). Promoters for use in cyanobacteria can also be modified from naturally-occurring promoters, and include combinations of naturally-occurring promoters, including, but not limited to, those disclosed herein. Also considered are prokaryotic promoters from a range of species, including eubacterial and cyanobacterial species, such as, for example, an ara promoter, an AraC promoter, a rha promoter, a nir promoter, a nar promoter, a pho promoter, a tet promoter, a cys promoter, a metallothionien promoter, an ftf promoter, a gln promoter, a heat shock promoter, a cold-inducible promoter, or a viral promoter. The foregoing lists are exemplary and not limiting.

Likewise, a wide variety of transcriptional terminators can be used for expression vector construction. Examples of possible terminators can include, but are not limited to, psbA, psaAB, rbc, secA, T7 coat protein, rrnB, and the like, and combinations thereof.

Transformation vectors can additionally or alternately include a selectable marker, such as but not limited to a drug resistance gene, an herbicide resistance gene, a metabolic enzyme and/or factor required for survival of the host (for example, an auxotrophic marker), or the like, or a combination thereof. Transformed cells can be optionally selected based upon the ability to grow in the presence of the antibiotic and/or other selectable marker under conditions in which cells lacking the resistance cassette or auxotrophic marker could not grow. Further additionally or alternately, a non-selectable marker may be present on a vector, such as a gene encoding a fluorescent protein or enzyme that generates a detectable reaction product.

A vector can also be an integration vector that includes one or more sequences that promoter integration of a gene of interest (i.e. the exogenous gene to be transformed into the host microorganism) or the gene expression cassette into the genome of the host microorganism. For example, an integration vector used to transform cyanobacteria can include at least one sequence of at least 50, at least 100, at least 200, at least 300, at least 400, at least 500, or at least 600 nucleotides with homology to a a sequence in the genome of the host organism to allow integration of the transgene or transgene expression cassette into the genome of the host microorganism to occur via homologous recombination. In some examples, the transgene or transgene expression cassette is flanked by sequences homologous to a region of the host chromosome to promote integration of the gene of interest into the host chromosome. Alternatively or in addition, an integration vector can include one or more sequences that promote site-specific recombination or random integration such as, but not limited to, sequences recognized by recombinases, integrases, or transposases. In some embodiments, the integration vector can further include a gene encoding a recombinase, integrase, or transposase.

For optimal expression of a recombinant protein, in many instances it can be beneficial to employ coding sequences that produce mRNA with codons preferentially used by the host cell to be transformed. Thus, for an enhanced expression of transgenes, the codon usage of the transgene can be matched with the specific codon bias of the organism in which the transgene is desired to be expressed. For example, methods of recoding genes for expression in microalgae are described in U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. In some embodiments, only a portion of the codons can be changed to reflect a preferred codon usage of a host microorganism, and in some embodiments, one or more codons can be changed to codons that are not necessarily the most preferred codon of the host microorganism encoding a particular amino acid. Additional information for codon optimization is available, e.g. at the codon usage database of GenBank.

Accordingly, the present invention also provides, in some embodiments, recombinant microorganisms transformed with an isolated nucleic acid molecule as described herein including a nucleic acid sequence that is codon-optimized for expression in the recombinant microorganism.

Vectors can be introduced into cyanobacteria via conventional transformation and/or transfection techniques. The terms "transformation" and "transfection", conjugation and transduction, as used in the present context, are intended to comprise a multiplicity of methods known to those skilled in the art for the introduction of foreign nucleic acid (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Examples of suitable methods for the transformation and/or transfection of host cells, e.g. can be found in Molecular Cloning—A Laboratory Manual (2010), Cold Spring Harbor Laboratory Press.

For example, cyanobacteria can be transformed by any suitable methods, including, as nonlimiting examples, natural DNA uptake (Zang (2007) *J. Microbiol.* 45, 241-245), conjugation (Wolk et al. (1984) *Proc. Natl. Acad. Sci. USA* 81, 1561-1565), transduction, glass bead transformation (Feng (2009) *Mol. Biol. Rep.* 36, 1433-9), silicon carbide whisker transformation (Dunahay (1997) *Methods Mol. Biol.* 62, 503-9), biolistics (Kroth (2007) *Methods Mol. Biol.* 390, 257-267), electroporation (Ludwig (2008) *Appl. Microbiol. Biotechnol.* 78, 729-35), laser-mediated transformation (WO2009/140701), incubation with DNA in the presence of or after pre-treatment with any of poly(amidoamine) dendrimers (Pasupathy (2008) *Biotechnol. J.* 3, 1078-82), polyethylene glycol (Ohnuma (2008) *Plant Cell Physiol.* 49, 117-120), cationic lipids (Muradawa (2008) *J. Biosci. Bioeng.* 105, 77-80), dextran, calcium phosphate, and/or calcium chloride (Mendez-Alvarez (1994) *J. Bacteriol.* 176, 7395-7397), optionally after treatment of the cells with cell wall-degrading enzymes (Perrone (1998) *Mol. Biol. Cell* 9, 3351-3365), or the like, or combinations thereof. *Agrobacterium*-mediated transformation can additionally or alternately be performed on algal cells, for example after removing or wounding the algal cell wall (Kumar (2004) *Plant Sci.* 166, 731-738).

Recombinant Microorganism

The present invention describes a recombinant microorganism transformed with a recombinant or exogenous nucleic acid molecule comprising a nucleic acid sequence encoding a transcription factor domain protein as described herein. Additionally or alternatively, the recombinant microorganism can be transformed with a recombinant or exogenous gene that is capable of regulating a metabolic pathway of the microorganism.

The present invention relates, in some embodiments, to recombinant microorganisms including a recombinant nucleic acid molecule including a nucleic acid sequence that encodes an amino acid sequence that shares at least about 75%, 80% or 85%, for example at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity with the amino acid sequence of SEQ ID NO:2, SEQ ID NO:4, SEQ ID NO:6, SEQ ID NO:10, SEQ ID NO:12, SEQ ID NO:14, SEQ ID NO:16, and/or SEQ ID NO:18, operably linked to a heterologous promoter. Additionally or alternately, the present invention relates, in some embodiments, to recombinant microorganisms transformed with an isolated nucleic acid molecule including a nucleic acid sequence that shares at least about 75%, at least about 80%, at least about 85%, for example at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity with the nucleic acid sequence of SEQ ID NO:1, SEQ ID NO:3, SEQ ID NO:5, SEQ ID NO:9, SEQ ID NO:11, SEQ ID NO:13, SEQ ID NO:15, and/or SEQ ID NO:17. Specifically contemplated are genomic or synthetic DNA sequences, cDNA, and mRNA, as well as nucleic acids based on alternative backbones and/or including alternative bases, whether derived from natural sources or synthesized.

The inventors contemplate that a transgenic microorganism can in some embodiments include more than one exogenous nucleic acid molecule encoding a transcription factor domain protein. For example, a transgenic cyanobacterium that includes a histidine kinase transcription factor domain protein can further include a response regulator transcription factor domain protein. For example, in some embodiments a recombinant microorganism includes an exogenous nucleic acid molecule encoding a polypeptide having at least about 75%, 80% 85%, 90%, 95%, at least about 96%, at least about 97%, at least about 98%, at least about 99%, or about 100% sequence identity with the amino acid sequence of SEQ ID NO:2 and includes a histidine kinase domain (i.e. the polypeptide that recruits to Pfam PF02518), and further includes an exogenous nucleic acid molecule encoding a polypeptide a polypeptide that includes a response regulator receiver domain, for example, a polypeptide that recruits to Pfam PF00072 or PF06490. In some examples, a transgenic microorganism that includes an exogenous nucleic acid molecule encoding a polypeptide having at least 75%, 80% 85%, 90%, 95%, or at least about 99% sequence identity with the amino acid sequence of SEQ ID NO:2 can further include an exogenous nucleic acid molecule encoding a polypeptide having at least 75%, 80% 85%, 90%, 95%, or at least about 99% sequence identity with the amino acid sequence of SEQ ID NO:4.

Additionally or alternatively, a transgenic microorganism that includes an exogenous nucleic acid molecule encoding a polypeptide having at least 75%, 80% 85%, 90%, 95%, at least about 96%, at least about 97%, at least about 98%, at least about 99%, or about 100% sequence identity with the amino acid sequence of SEQ ID NO:4, SEQ ID NO:14, SEQ ID NO:16, or SEQ ID NO:18, in which the polypeptide includes a response regulator receiver domain (recruits to Pfam PF00072), in which the recombinant microorganism further includes an exogenous nucleic acid molecule encoding a polypeptide that includes a histidine kinase domain and recruits to Pfam PF07730, PF07536, PF00512, PF07568, or PF02518.

A recombinant microorganism that includes a recombinant gene encoding a protein that regulates fatty acid biosynthesis and/or lipid pathways, including a transcription factor domain protein can regulate production of at least one free fatty acid or fatty acid derivative, such as one or more of a C6, C8, C10, C12, C14, C16, C18, C20, C22, or C24 free fatty acid or fatty acid derivative. The recombinant microorgansim as provided herein produces, in preferred embodiments, more of at least one free fatty acid or fatty acid derivative than the same microorganism that is not genetically engineered.

Further included are microorganisms that include endogenous genes encoding transcription factor domain proteins having at least 75%, 80% 85%, 90%, 95%, or at least about 99% sequence identity with the amino acid sequence of any of SEQ ID NO:2, SEQ ID NO:4, SEQ ID NO:6, SEQ ID NO:10, SEQ ID NO:12, SEQ ID NO:14, or SEQ ID NO:16, in which the recombinant microorganisms are engineered to include a heterologous promoter inserted into the host genome such that it is operably linked to the gene encoding a transcription factor domain protein.

The recombinant microorganisms of the present invention, in some embodiments, are transformed with exogenous genes by the introduction of appropriate expression vectors described herein.

The term "gene" is used broadly to refer to any segment of nucleic acid molecule (typically DNA, but optionally RNA) encoding a protein or expressed RNA. Thus, genes include sequences encoding expressed RNA (which can include polypeptide coding sequences) and, often, the regulatory sequences required for their expression. Genes can be obtained from a variety of sources, including cloning from a source of interest or synthesizing from known or predicted sequence information and may include sequences designed to have desired parameters.

A "recombinant" or "engineered" nucleic acid molecule is a nucleic acid molecule that has been altered through human manipulation. As non-limiting examples, a recombinant nucleic acid molecule: (1) includes conjoined nucleotide sequences that are not conjoined in nature, (2) has been engineered using molecular cloning techniques such that it lacks one or more nucleotides with respect to the naturally occurring nucleic acid molecule sequence, or (3) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the term recombinant, engineered, or genetically engineered refers to organisms that have been manipulated by introduction of a heterologous or recombinant nucleic acid sequence into the organism, and includes gene knockouts, targeted mutations and gene replacement, promoter replacement, deletion, or insertion, as well as introduction of transgenes into the organism. The heterologous or recombinant nucleic acid molecule can be integrated into the recombinant/genetically engineered organism's genome or in other instances are not integrated into the recombinant/genetically engineered organism's genome.

The term "recombinant protein" as used herein refers to a protein produced by genetic engineering.

An "expression cassette" as used herein, refers to a gene encoding a protein or functional RNA (e.g. a tRNA, a microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

When referring to a gene regulatory sequence or to an auxiliary nucleic acid sequence used for maintaining or manipulating a gene sequence (e.g. a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter", even though the promoter may be derived from the same species (or, in some cases, the same organism) as the gene to which it is linked.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. (A descendent of a cell that was transformed with a nucleic acid molecule is also referred to as "transformed" if it has inherited the exogenous nucleic acid molecule). The exogenous gene may be from a different species (and so "heterologous"), or from the same species (and so "homologous"), relative to the cell being transformed. An "endogenous" nucleic acid molecule, gene, or protein is the organism's own nucleic acid molecule, gene, or protein as it occurs in, or is naturally produced by, the organism.

The term "heterologous" is used broadly in this aspect to indicate that the nucleic acid molecules disclosed herein is introduced into cyanobacteria is derived from an organism other than cyanobacteria. A heterologous gene may have an equivalent in the transformed host, i.e. one which normally performs the same or a similar function, or the exogenous heterologous gene may encode a transcription factor domain protein that does not have an endogenous homologue in the host strain.

Nucleic acid molecules heterologous to a cyanobacterial host strain may be nucleic acid molecules not naturally-occurring in cells of that type, variety or species. In some embodiments, the heterologous nucleic acid encoding a transcription factor domain protein may comprise a coding sequence of, or derived from, an organism other than cyanobacteria. A further possibility is for a nucleic acid sequence to be placed within a cyanobacteria in which it or a homolog is found naturally, but wherein the nucleic acid sequence is linked and/or adjacent to nucleic acid which does not occur naturally within the cell, or cells of that type or species or variety of cyanobacteria, such as operably linked to one or more regulatory sequences, such as a promoter sequence, for control of expression.

The genetically engineered microorganism that includes an exogenous transcription factor domain protein gene, preferably operably linked to a heterologous promoter can be any prokaryotic microorganism, including without limitation, a eubacterium, archaebacterium, green nonsulfur bacterium, or purple nonsulfur bacterium or cyanobacterium.

More than thirty cyanobacterial genomes have been completely sequenced to date, including, for example, the genomes of various *Acaryochloris, Arthrospira, Cyanobacterium, Cyanothece, Gloeobacter, Microcystis, Nostoc, Prochlorococcus, Synechococcus, Synechocystis,* and *Thermosynechococcus* species, and many cyanobacterial species been manipulated using molecular biological techniques, including for example the cyanobacteria *Leptolyngbya, Anabaena (Nostoc)* sp. PCC 7120, *Anabaena variabilis* ATCC 29413, *Nostoc punctiforme* ATCC 29133, *Nostoc* sp. PCC 7422, *Synechocystis* sp. PCC 6803, *Synechococcus elongatus* PCC 7942, *Synechococcus elongatus* PCC 7002, etc. (Taton et al. (2012) *PLoS One* Vol. 7, Iss. 1 e30910; Ruffing (2011) *Bioengineered Bugs* 2:136-149). The genetically engineered microorganisms provided herein can be species of genera including, but not limited to, the following genera of cyanobacteria: *Agmenellum, Anabaena, Anabaenopsis, Anacystis, Aphanizomenon, Arthrospira, Asterocapsa, Borzia, Calothrix, Chamaesiphon, Chroococcus, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechocystis, Tolypothrix, Trichodesmium, Tychonema* and *Xenococcus*. For example, the recombinant cyanobacterium can be a *Synechococcus, Synechocystis,* or *Thermosynechococcus* species. Alternatively, the recombinant photosynthetic microorganism can be a *Cyanobium, Cyanothece,* or *Cyanobacterium* species, or further alternatively, the recombinant photosynthetic microorganism can be a *Lyngbya* or *Leptolyngbya* species.

In certain examples, the recombinant host microorganism can be a species of a genius from which the transcription factor domain protein gene is derived, for example, a cyanobacterium of a species of the genus *Leptolyngbya* can be engineered to include an exogenous gene encoding a transcription factor domain protein having at least 60%, 65%, 70%, 75%, 80%, 85%, 90%, 95% identity to SEQ ID NO:2, SEQ ID NO:4, or SEQ ID NO:6 (e.g., at least 85%, 90%, 95% identity to SEQ ID NO:2, SEQ ID NO:4, or SEQ ID NO:6), or can be engineered to overexpress an endogenous gene encoding an ortholog of the transcription factor domain protein of SEQ ID NO:2, SEQ ID NO:4, or SEQ ID NO:6 (e.g., an endogenous transcription factor domain protein having at least 60%, 65%, 70%, 75%, 80%, 85%, 90%, or 95% identity to SEQ ID NO:2, SEQ ID NO:4, or SEQ ID NO:6). In other examples, a recombinant cyanobacterial *Synechococcus* species can be engineered to include an exogenous gene encoding a transcription factor domain protein having at least 60%, 65%, 70%, 75%, 80%, 85%, 90%, 95% identity to SEQ ID NO:14 or SEQ ID NO:16 (e.g., at least 85%, 90%, 95% identity to SEQ ID NO:14 or SEQ ID NO:16), or can be engineered to overexpress an endogenous gene encoding an ortholog of the transcription factor domain protein of SEQ ID NO:14, or SEQ ID NO:16 (e.g., an endogenous transcription factor domain protein having at least 60%, 65%, 70%, 75%, 80%, 85%, 90%, or 95% identity to SEQ ID NO:14 or SEQ ID NO:16).

As described herein, in some embodiments of the present invention, a microorganism with an altered metabolic pathway is provided that comprises an exogenous nucleic acid molecule encoding a transcription factor domain protein, and the microorganism produces a greater amount of at least one free fatty acid or at least one fatty acid derivative than does a microorganism that does not contain an exogenous nucleic acid molecule encoding the transcription factor domain protein. In some embodiments, the amount of a free fatty acid or fatty acid derivative produced by the microorganism is at least 290 mg per liter of culture, and can be at least 300 mg per liter of culture, at least about 350 mg per liter of culture, at least about 400 mg per liter of culture, at least about 450 mg per liter of culture. In some embodiments, the amount of a free fatty acid or fatty acid derivative produced by a culture of a microorganism that includes an exogenous nucleic acid molecule encoding a transcription factor domain protein as described herein is at least 10%, at least 15%, at least 20%, at least 25%, at least 30%, at least 40%, at least 50%, at least 60%, at least 65%, at least 70%, at least 80%, at least 90%, at least 95%, at least 100%, or at least 200% greater than the amount of free fatty acid or fatty acid derivative produced by a microorganism identical in all respects except that it does not include an exogenous nucleic acid molecule encoding a transcription factor domain protein.

Optionally but preferably, the recombinant microorganism that includes a recombinant or exogenous nucleic acid molecule that encodes a transcription factor domain protein can be transformed with at least one additional recombinant or exogenous gene for producing free fatty acids and/or one or more fatty acid derivatives, such as, for example, a fatty alcohol, a fatty aldehyde, a wax ester, an alkane, or an alkene.

Other Modifications

In addition to providing an expression system for one or more recombinant genes encoding a transcription factor domain protein, further modifications in the microorganism may be made to direct synthesis of free fatty acids or fatty acid derivatives. For example, a host microorganism that includes an exogenous gene encoding a transcription factor domain protein can further include one or more exogenous thioesterase and/or genes encoding polypeptides having lipolytic activity. Fatty acids released from thioester substrates or lipids can optionally be converted to fatty acid derivatives such as fatty aldehydes, fatty alcohols, wax esters, alkanes, or alkenes.

An exogenous thioesterase expressed in the host microorganism can be, for example, an acyl-ACP thioesterase, an acyl-CoA thioesterase, or a hydroxylbenzoyl thioesterase. For example, a microorgansim for the production of free fatty acids in some embodiments can be transformed with a gene encoding an exogenous acyl-ACP thioesterase, such as a gene encoding a polypeptide that when queried against the pfam database, provides a match with Pfam PF01643 having a bit score of less than or equal to 20.3 (the gathering cut-off for PF01643). The exogenous acyl-ACP thioesterase gene can encode an acyl-ACP thioesterase from a higher plant species. Genes encoding acyl-ACP thioesterases derived from higher plants can include, without limitation, genes encoding acyl-ACP thioesterases from *Cuphea* species (e.g. *Cuphea carthagenensis*, *Cuphea wrightii* (e.g., GenBank Accession AAC49784), *Cuphea lanceolata* (e.g., GenBank Accession CAA54060), *Cuphea palustris*, (e.g., GenBank Accessions AAC49783; AAC49179); *Cuphea hookeriana* (e.g., GenBank Accessions AAC72882; AAC49269; AAC72881; AAC72883), *Cuphea calophylla* (e.g., GenBank Accession ABB71580) or genes of various *Cuphea* species disclosed in United States patent application publication US 2011/0020883, incorporated by reference herein) or genes from other higher plant species. In further examples, a microorganism used in the methods and cultures disclosed herein can include a gene encoding an acyl-ACP thioesterase from species such as but not limited to, *Arabidopsis* (e.g., GenBank Accessions XP_002885681; NP_172327); *Arachis hypogaea* (e.g., GenBank Accession ABO38556); *Brassica* species (e.g., GenBank Accession CAA52069.1); *Camellia oleifera* (e.g., GenBank Accession ACQ57189); *Cinnamonum camphorum* (e.g., GenBank Accession AAC49151); *Cocos nucifera* (e.g., GenBank Accessions AEM72519; AEM72520; AEM72521); *Glycine max* (e.g., GenBank Accession ABD91726); *Garcinia mangostana* (e.g., GenBank Accession AAB51525); *Gossypium hirsutum* (e.g., GenBank Accession AAD01982); *Helianthus annuus* (e.g., GenBank Accession AAQ08226); *Jatropha curcas* (e.g., GenBank Accession ABU96744); *Macadamia tetraphylla* (e.g., GenBank Accession ADA79524); *Elaeis oleifera* (e.g., GenBank Accession AAM09524); *Elaeis guineensis* (e.g., GenBank Accession AAD42220); *Oryza sativa* (e.g., GenBank Accession BAA83582); *Populus tomentosa* (e.g., GenBank Accession ABC47311); *Umbellularia californica* (e.g., GenBank Accession AAC49001); *Ulmus Americana* (e.g., GenBank Accession AAB71731); and *Zea mays* (e.g., GenBank Accession ACG41291), or any of those disclosed in U.S. Pat. No. 5,455,167; U.S. Pat. No. 5,654,495; and U.S. Pat. No. 5,455,167; and in U.S. Patent Appl. Pub. Nos. 2009/0298143 and 2011/0020883; all incorporated by reference herein in their entireties. Further included are acyl-ACP thioesterases from mosses (Bryophyta), such as, for example, *Physcomitrella patens*, (e.g., GenBank Accession XP 001770108). The foregoing examples are not limiting with regard to the types or specific examples of acyl-ACP thioesterase genes that can be used.

Further included are acyl-ACP thioesterase genes from prokaryotic organisms. Illustrative examples of prokaryotic acyl-ACP thioesterases that may be expressed by a microorganism useful in the methods and cultures provided herein include, but are not limited to acyl-ACP thioesterases from *Desulfovibrio desulfuricans* (e.g. Q312L1 GI:123552742); *Elusimicrobium minutum* (e.g. ACC98705 GI:186971720); *Carboxydothermus hydrogenoformans* (e.g. YP_359670 GI:78042959); *Clostridium thermocellum* (e.g. YP_001039461 GI:125975551); *Moorella thermoacetica* (e.g. YP_431036 GI:83591027); *Geobacter metallireducens* (e.g. YP_384688 GI:78222941); *Salinibacter ruber* (e.g. YP_444210 GI:83814393); *Microscilla marina* (e.g. EAY28464 123988858); *Parabacteroides distasonis* (e.g. YP_001303423 GI:150008680); *Enterococcus faecalis* (e.g. ZP_03949391 GI:227519342); *Lactobacillus plantarum* (e.g. YP_003062170 GI:254555753); *Leuconostoc mesenteroides* (e.g. YP_817783 GI:116617412); *Oenococcus oeni* (e.g. ZP_01544069 GI:118586629); *Mycobacterium smegmatis* (e.g. AB K74560 GI:118173664); *Mycobacterium vanbaalenii* (e.g. ABM11638 GI:119954633); *Rhodococcus erythropolis* (e.g. ZP_04385507 GI:229491686; *Rhodococcus opacus* (e.g. YP_002778825 GI:226361047), or any of those disclosed in the co-pending, commonly-assigned patent application Ser. No. 13/324,623 entitled "Prokaryotic Acyl-ACP Thioesterases for Producing Fatty Acids in Genetically Engineered Microorganisms", filed on Dec. 13, 2011, which is incorporated herein by reference in its entirety.

In additional embodiments, a gene encoding an acyl-CoA thioesterase can be introduced into a host microorganism that includes an exogenous nucleic acid molecule encoding a transcription factor domain protein. An acyl-CoA thioesterase gene transformed into a microorganism for the production of free fatty acids or fatty acid derivatives can be from a plant, animal, or microbial source. For example, a gene encoding the TesA or TesB thioesterase of *E. coli*, or a variant thereof, for example, an acyl-CoA thioesterase such as not limited to a variant as disclosed in WO 2010/075483, incorporated by reference herein in its entirety, can be introduced into a microorganism. Also included are genes encoding proteins that when queried against the Pfam database of protein families are identified as members of Pfam PF02551 (acyl- CoA thioesterase), where the bit score is equal to or greater than the gathering cut off (20.7).

Alternately or in addition, the microorganism can include one or more genes encoding an exogenous hydroxybenzoyl thioesterase, for example an exogenous 4-hydroxybenzoate thioesterase or 4-chlorobenzoate thioesterase. Genes encoding hydroxybenzoyl thioesterases that may be useful in a microorganism for producing free fatty acids can include, for example, those disclosed in the co-pending, commonly-assigned patent application Ser. No. 13/324,607 entitled "Genetically Engineered Microorganisms Comprising 4-Hydroxybenzoyl-CoA Thioesterases and Methods of Using Same for Producing Free Fatty Acids and Fatty Acid Derivatives", filed on Dec. 13, 2011, incorporated herein by reference in its entirety; 4-hydroxybenzoate thioesterases from *Bacillus* species and *Geobacillus* species; as well as 4-hydroxybenzoate thioesterases of *Acidiphilium, Bartonella, Rhodopseudomonas, Magnetospirillum, Burkholderia, Granulibacter, Rhizobium*, and *Labrenzia* species, or the like; or combinations thereof.

Further additionally or alternatively, the recombinant microorganism can include those genetically engineered with exogenous or endogenous genes encoding polypeptide having lipolytic activity capable of producing free fatty acids from membrane lipids or storage lipids, e.g. phospholipids, triacylglycerols, diacylglycerols, monoacylglycerols, or the like, or combinations thereof. Lipases are enzymes that catalyze the hydrolysis of ester bonds in glycerolipids, including, but not limited to, mono-, di-, and tri-acyl glycerols, as well as combinations thereof, to release free fatty acids and alcohols The use of genes encoding polypeptides having lipolytic activity in microorganisms used in the production of free fatty acids is disclosed in the co-pending, commonly-assigned U.S. patent application Ser. No. 13/324,653 entitled "Production of Free Fatty Acids and Fatty Acid Derivatives by Recombinant Microorganisms Expressing Polypeptides Having Lipolytic Activity," filed on Dec. 13, 2011, and which is incorporated herein by reference in its entirety. The gene encoding a polypeptide having lipolytic activity can be a gene encoding any lipase, e.g. that liberates a fatty acid from a glycerolipid (including a monoglyceride, a diglyceride, a triglyceride, a phospholipid, a galactolipid, etc.) or can be a gene encoding an amidase. For example, a lipase gene can encode a polypeptide having lipase activity that is a member of the Pfam AB Hydrolase clan, CL0028, such as but not limited to, a lipase that is a member of Pfam 01674, Pfam 01764, Pfam 07819, Pfam 03583, and/or Pfam 00151. In some embodiments, an exogenous lipase gene introduced into a microorganism can encode a protein with an amino acid sequence having an E-value parameter of 0.01 or less when queried using the Pfam Profile HMM for any of Pfam PF01674, Pfam PF 01764, Pfam PF07819, Pfam PF03583, Pfam PF00151, Pfam PF00561, Pfam PF02230, Pfam PF07859, Pfam PF08386, Pfam PF12695, Pfam PF12697, Pfam PF12715, and/or Pfam PF04083. Further, the recombinant microorganism can include a non-native gene encoding an amidase having lipolytic activity, such as but not limited to an amidase that recruits to Pfam PF01425 (Amidase) with a bit score greater than the gathering cutoff of 20.1, that can catalyze the release of fatty acids from lipids.

Additionally or alternatively contemplated are recombinant microorganisms that are engineered to include gene regulatory sequences that induce or increase expression of an endogenous lipase gene. For example, a microorganism can be engineered such that a heterologous promoter is inserted upstream of a coding region of an endogenous lipase gene. The heterologous promoter can replace an endogenous promoter and/or can be inserted upstream or downstream of the endogenous promoter that regulates expression of the endogenous lipase gene, for example using homologous recombination or site-specific recombination. The heterologous promoter can be a constitutive promoter or an inducible promoter that increases expression of the endogenous lipase gene.

Still further additionally or alternatively, the microorganism can include nucleic acid molecules encoding variants of naturally-occurring acyl-ACP thioesterases, acyl-CoA thioesterases, hydroxybenzoyl thioesterases, lipases, or amidases, in which the variants have at least 80%, for example at least 85%, at least 90%, or at least 95%, identity to the amino acid sequences accessed by the provided or referenced Genbank Accession Numbers, in which the variants have at least the level of activity (e.g. thioesterase or lipolytic activity) as the reference sequence.

Additionally but optionally, a recombinant microorganism engineered to include an exogenous gene encoding a thioesterase for the production of fatty acids or fatty acid derivatives can further include an exogenous gene encoding a lysophosphatidic acid acyltransferase (LPAAT), where the LPAAT has a different acyl-ACP substrate preference than the acyl-ACP substrate preference of the thioesterase. Alternatively, the genetically engineered microorganism, which can be a genetically engineered cyanobacterium, can overexpress an endogenous LPAAT gene having a different substrate preference than the substrate preference of an exogenous thioesterase gene. The engineering of microorganisms such as cyanobacteria to increase fatty acid production by expression of LPAAT genes is disclosed in co-pending and commonly-assigned U.S. patent application Ser. No. 13/404,717 entitled "Enhanced Production of Fatty Acids and Fatty Acid Derivatives by Recombinant Microorgnanisms" filed Feb. 24, 2012, and incorporated herein by reference in its entirety.

Further Modifications for Producing Fatty Acid Derivatives

Additionally or alternatively, the recombinant microorganisms of the invention can include additional modifications for the production of fatty acid derivatives such as, e.g., fatty aldehydes, fatty alcohols, fatty acid esters, wax esters, and hydrocarbons, including alkanes and alkenes. In some circumstances, the recombinant microorganisms provided herein can include a thioesterase gene and/or a gene encoding a polypeptide having lipolytic activity and can include additional enzymes that convert free fatty acids to fatty acid derivatives. Alternatively, a microorganism as disclosed herein may not express an exogenous thioesterase gene or gene encoding a polypeptide having lipolytic activity, but may include genes such as acyl reductases or wax synthases that can be used to produce fatty aldehydes, alkanes, alkenes, fatty alcohols, or wax esters without requiring expression of an exogenous thioesterase or lipase.

For the production of fatty aldehydes, which can optionally be further converted to products such as fatty alcohols, wax esters, or alkanes, a transgenic microorganism as provided herein can include an exogenous gene(s) that encodes an aldehyde-forming reductase, such as, for example, an aldehyde-forming acyl-CoA reductase, an aldehyde-forming acyl-ACP reductase, or a carboxylic acid reductase. Genes or portions of genes that are listed in GenBank and other genetic databases and that are predicted to encode proteins that are homologous to known acyl-CoA reductases that produce fatty aldehydes, referred to herein as "aldehyde-generating fatty acyl-CoA reductases", can be introduced into various microorganisms in order to test for the production of specific fatty aldehydes or fatty alcohols produced therefrom. Non-limiting examples of fatty aldehyde-generating acyl-CoA reductases include the Acr1 gene of *Acinetobacter baylyi* (Accession U77680, GI:1684885), the AcrM-1 gene of *Acinetobacter* sp. M-1 (Accession YP 001086217, GI:18857900), and the luxC and luxE genes of various photoluminescent bacteria, e.g., an *Altermonas, Photobacterium, Shewanella, Vibrio,* or *Xenorhabdus* species. The enzymes encoded by these and other genes identified, for example, by sequence homology or protein domain can be tested to determine their substrates and products using assays know in the art.

Nonlimiting examples of carboxylic acid reductases that can be used in the invention for the production of fatty aldehydes include the *Nocardia* CAR gene (GenBank Accession AY495697; GI:40796034) and homologs thereof, some of which are disclosed in US2010/0105963, incorporated by reference herein.

In some examples, the host cell can include a non-native gene encoding an aldehyde-forming acyl-ACP reductase such as but not limited to any of those disclosed in WO 2009/140696 and WO 2011/066137. For example, the recombinant host cell may comprise an aldehyde-forming acyl-ACP reductase that has at least 50%, 60%, 70%, 80%, 90% or 95% sequence identity to an aldehyde-forming reductase, e.g., as disclosed in WO 2009/140696 or WO 2011/066137, such as, for example, any of the reductases having the accession numbers AAM82647; AAM82647; BAD78241; ABA22149; BAB76983; ZP_03763674; ACL42791; ZP_01628095; ZP_01619574; YP_001865324; YP_721978; NP_682102; YP_001518341; YP_002371106; ZP_05027136; ZP_03273554; NP_442146; ZP_01728620; ZP_05039135; YP_001802846; NP_926091; YP_001660322; ZP_00516920; CAO90781; ZP_01085337; YP_001227841; ABD96327; NP_897828; YP_001224378; ABD96480; ZP_01123215; ABB92249; ZP_01079773; YP_377636; NP_874926; NP_895058; ABD96274; ABD96442; ZP_01469469; ZP_05045052; YP_001014416; YP_001010913; YP_381056; YP_001550421; NP_892651; YP_001090783; ZP_01472595; YP_293055; ZP_05138243; YP_731192; YP_001483815; YP_001008982; YP_473896; YP_478638; or YP_397030. In some embodiments the recombinant host cell includes an exogenous gene encoding an aldehyde-forming acyl-ACP reductase, where the aldehyde-forming acyl-ACP reductase can be from a cyanobacterial species, and may be from the same species as the host microorganism, or may be from a different species. Alternatively, a cyanobacterial host can be engineered to overexpress an endogenous acyl-ACP reductase gene.

For the production of fatty alcohols, a recombinant microorganism as provided herein can include an exogenous gene encoding an alcohol-forming acyl reductase such as bfar from *Bombyx mmori*; jjfar from *Simmondsia chinensis*, an acyl-CoA reductase from *Titicum aestivum*, mfar1 of *Mus musculus*, mfar2 from *Mus musculus*, hfar from *H. sapiens*, FARXIII of *Ostrinia scapulalis*, MS2 of *Z. mays*, the putative fatty acyl-coA reductase of *Oryza sativa* (Genbank accession BAC84377) or MS2, FAR4, FARE, or CER4 of *Arabidopsis thaliana*. An alcohol-forming fatty acyl-CoA reductase can also be a prokaryotic enzyme, such as for example, those having Genbank accession numbers AAC45217 (*Acinetobacter baylyi* fatty acyl-CoA reductase), YP_047869 (*Acinetobacter* sp. ADP1 fatty acyl-CoA reductase), BAB85476 (*Acinetobacter* sp. M-1 acyl coenzyme A reductase), YP_001086217 (*Acinetobacter baumannii* ATCC 17978 acyl coenzyme A reductase), YP_580344 short-chain dehydrogenase/reductase SDR (*Psychrobacter cryohalolentis* K5), YP_001280274 (*Psychrobacter* sp. PRwf-1 short-chain dehydrogenase/reductase SDR), the acyl reductase of *Marinobacter algicola* DG893 (Accession ZP_01892457), the short chain acyl dehydrogenase of *Marinobacter aquaeolei* Maqu_2507 (YP_959769) *Marinobacter aquaeolei* VT8 Maqu_2220 (YP_959486), *Hahella chejuensis* Hch_05075 (YP_436183), *Marinobacter adhaerens* HP15_810 (ADP96574), or an acyl reductase of an *Oceanobacter* species (e.g., RED65_09894, Accession EAT13695). Alcohol-forming reductases may include those that are able to use acyl-ACP as a substrate, as disclosed in the co-pending, commonly-assigned U.S. patent application No. 61/539,640 entitled "Fatty Alcohol-Forming Acyl-ACP Reductases", filed on Sep. 27, 2011, incorporated herein by reference in its entirety, as well as in the co-pending, commonly-assigned U.S. patent application Ser. No. 13/413,426 entitled "Acyl-ACP Wax Ester Synthases", filed on Mar. 6, 2012 also incorporated herein by reference in its entirety. The use of genes encoding alcohol-forming reductases that utilize acyl-ACP as a substrate can obviate the need to engineer a cyanobacterial host with a gene encoding a thioesterase or lipase and/or a gene encoding an acyl-CoA synthetase.

Alternatively or in addition, the recombinant microorganism or host cell comprises one or more nucleic acid molecules encoding an exogenous acyl-CoA reductase, carboxylic acid reductase, and/or acyl-ACP reductase, and an exogenous wax synthase and can produce a wax ester. Wax esters include an A chain and a B chain linked through an ester bond, one or both of which can be derived from a fatty acid generated by the recombinant microorganisms or host cells of the invention. Wax esters produced by the recombinant microorganisms or host cells of the invention include, e.g., A chain lengths of from 8 to 24 carbons and/or B chain lengths of from 8 to 24 carbons. For example, the wax esters can have A+B chain lengths including, but not limited to, of 16 to 48 carbons, 16 to 36 carbons, 16 to 32 carbons, or 24 to 32 carbons.

Wax synthases include polypeptides having enzyme classification number EC 2.3.1.75, as well as any other peptide capable of catalyzing the conversion of an acyl-thioester to fatty esters, e.g., some acyltransferases, including some DGATs. Some wax synthase peptides can catalyze other reactions as well, for example some wax synthase peptides will accept short chain acyl-CoAs and short chain alcohols to produce fatty esters. Methods to identify wax synthase activity are provided in U.S. Pat. No. 7,118,896, which is herein incorporated by reference. Nonlimiting examples of wax synthases that can be encoded by an exogenous nucleic acid molecule introduced into a recombinant microorganism as disclosed herein include the bifunctional wax ester synthase/acyl-CoA:diacylglycerol acyltransferase of *Simmondsia chinensis* (AAD38041), the wax synthase of *Acinetobacter* sp. strain ADP 1 (CAG67733), *Pseudomonas aeruginosa* (AAG06717), *Arabidopsis thaliana* (Q93ZR6), *Alcanivorax* (EDX90960), *Rhodococcus opacus* (YP_002782647), *Homo sapiens* (Q6E213), *Mus musculus* (Q6E1M8), or *Petunia×hybrida* (AAZ08051), and those disclosed in in co-pending, commonly-assigned U.S. patent application Ser. No. 13/408,270 entitled "Four-Gene Pathway for Wax Ester Synthesis", filed on Feb. 29, 2012, which is incorporated herein by reference in its entirety. Additional examples of wax synthases, including wax synthases that do not require acyl-CoA substrate, and therefore may be used in cyanobacterial strains that lack an exogenous thioesterase or lipase gene, and/or lack an exogenous acyl-CoA synthetase gene, are provided co-pending, commonly-assigned U.S. patent application Ser.

No. 13/413,426 entitled "Acyl-ACP Wax Ester Synthases", filed on Mar. 6, 2012, which is incorporated herein by reference in its entirety.

In some embodiments, the recombinant microorganisms of the invention comprise at least one nucleic acid molecule encoding an exogenous fatty acid decarboxylase or an exogenous fatty aldehyde decarbonylase, or additionally at least one exogenous nucleic acid molecule encoding an exogenous acyl-CoA reductase, carboxylic acid reductase, or acyl-ACP reductase, and can produce an alkane and/or alkene. Alkanes and alkenes produced by the recombinant microorganisms or host cells of the invention can, for example, have chain lengths of 7, 9, 11, 13, 15, 17, 19, 21, and/or 23 carbons, including, for example, chain lengths of 7, 9, 11, 13, 15, and/or 17 carbons, or chain lengths of 7, 9, 11, 13, and/or 15 carbons, or chain lengths of 11, 13, and/or 15 carbons.

Additionally, the recombinant microorganisms of the invention that produce a fatty alcohol, fatty aldehyde, fatty acid ester, wax ester, or hydrocarbons, including an alkane or an alkene, may optionally include a nucleic acid molecule encoding an exogenous acyl-CoA synthetase, or may be engineered to have upregulated expression of an endogenous acyl-CoA synthetase gene.

Further additionally, the recombinant microorganism may optionally be engineered to express an exogenous transmembrane transporter to facilitate secretion of one or more fatty acid products. For example, the recombinant host cell can include a non-native gene encoding an ATP-binding cassette (ABC) transporter or an RND pump. In some embodiments, the transporter is at least 80% identical in sequence to a transporter protein encoded by an *Arabidopsis* genes CER5, WBC11, AtMRPS, AmiS2 and AtPGP1, or fatty acid transporter (FATP) genes from *Saccharomyces, Drosophila,* mycobacterial species, or mammalian species. Also included are genes encoding variants of these and other naturally-occurring enzymes that participate in the synthesis of fatty acid products having at least 65% identity to the referenced or naturally-occurring proteins, in which the activity of the enzyme is not substantially reduced with respect to the wild-type or above-referenced enzyme.

The above-described recombinant microorganisms may be used in any of the methods of producing a fatty acid product as described herein.

Other Modifications for Producing Free Fatty Acids and/or Fatty Acid Derivatives Additionally or alternatively to providing an expression system for one or more exogenous genes encoding a transcription factor domain protein, further modifications in the microorganism may be made. For example, in addition to having an exogenous gene encoding a transcription factor domain protein, a microorganism used in the methods herein can additionally or alternatively include microorganisms having at least one additional exogenous nucleic acid molecule that encodes a polypeptide that participates in the synthesis of a fatty acid. For example, a transgenic microorganism for the production of one or more fatty acids can include an exogenous gene encoding an acetyl-CoA carboxylase, a malonyl CoA: ACP transacylase, or a beta-ketoacyl-ACP synthase.

The present invention also provides recombinant microorganisms that further include at least one endogenous gene that is attenuated or disrupted. Such an endogenous gene that can be attenuated or disrupted in the recombinant microorganism includes, but not limited to, acyl-CoA synthetase, acyl-ACP synthetase, acyl CoA dehydrogenase, glycerol-3-phosphate dehydrogenase, acetaldehyde CoA dehydrogenase, pyruvate dehydrogenase, acetate kinase, and the like, and combinations thereof.

Further additionally or alternatively, the microorganism can be modified such that one or more genes that encode beta-oxidation pathway enzymes have been inactivated and/or downregulated, and/or such that the enzymes themselves that are operative on such beta-oxidation pathways may be inhibited. This could prevent the degradation of fatty acids released from acyl-ACPs, thus enhancing the yield of fatty acids or fatty acid derivatives. In cases where the desired products are medium-chain fatty acids, the inactivation and/or downregulation of genes that encode acyl-CoA synthetase and/or acyl-CoA oxidase enzymes that preferentially use these chain lengths as substrates could be beneficial. Mutations in the genes encoding medium-chain-specific acyl-CoA synthetase and/or medium-chain-specific acyl-CoA oxidase enzymes, such that the activity of the enzymes could be diminished, may additionally or alternately be effective in increasing the yield of produced and/or released fatty acids or fatty acid derivatives. An additional modification can inactivate and/or downregulate the acyl-ACP synthetase gene and/or can inactivate and/or inhibit the encoded protein. Mutations in the genes can be introduced either by recombinant or non-recombinant methods. These enzymes and their genes are known and may be targeted specifically by disruption, deletion, generation of antisense sequences, generation of ribozymes, and/or other recombinant approaches known to the practitioner. Inactivation of the genes can additionally or alternatively be accomplished by random mutation techniques such as exposure to UV and/or chemical mutagens, and the resulting cells can be screened for successful mutants. The proteins themselves can be inhibited by intracellular generation of appropriate antibodies, intracellular generation of peptide inhibitors, or the like, or some combination thereof.

Still further additionally or alternately, the photosynthetic microorganism can be modified such that one or more genes that encode storage carbohydrate and/or polyhydroxyalkanoate (PHA) biosynthesis pathway enzymes can be inactivated or downregulated, and/or such that the enzymes themselves that are operative on such pathways are inhibited. Examples include, but not limited to, enzymes involved in glycogen, starch, or chrysolaminarin synthesis, including glucan synthases and branching enzymes. Other examples include enzymes involved in PHA biosynthesis such as acetoacetyl-CoA synthase and PHA synthase.

Methods of Producing Fatty Acids and Fatty Acid Derivatives

Also included are methods of producing a fatty acid or fatty acid derivative using a microorganism transformed with a recombinant nucleic acid molecule encoding a transcription factor domain protein as disclosed herein The invention encompasses methods of producing a free fatty acid and/or fatty acid derivative by culturing the recombinant microorganisms described herein. The free fatty acid derivative can be, for example, a fatty aldehyde, a fatty alcohol, a wax ester, an alkene, and/or an alkane. The methods can further comprise isolating at least one free fatty acid and/or fatty acid derivative. Optionally, at least a portion of the free fatty acid and/or fatty acid derivative produced by the recombinant microorganisms is released into the growth media by the microorganism. In some embodiments, the expression of the polypeptide encoded by the nucleic acid molecule described herein can be induced in the recombinant microorganism to produce the free fatty acid and/or fatty acid derivative.

Releasing and secreting, as used herein, are used interchangeably to refer to active and/or passive transport mechanisms wherein fatty acids or fatty acid derivatives are able to cross the cell membrane. Examples of such transport mechanisms can include, but are not necessarily limited to, gradient diffusion, facilitated diffusion, active transport, and combinations thereof.

Culturing refers to the intentional fostering of growth (e.g. increases in cell size, cellular contents, and/or cellular activity) and/or propagation (e.g. increases in cell numbers via mitosis) of one or more cells by use of selected and/or controlled conditions. The combination of both growth and propagation may be termed proliferation. Nonlimiting examples of selected and/or controlled conditions can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism can be grown heterotrophically, using a reduced carbon source, or mixotrophically, using both light and a reduced carbon source. Additionally or alternately, the microorganism can be cultured phototrophically. When growing phototrophically, the microorganism can advantageously use light as an energy source. An inorganic carbon source, such as $CO_2$ or bicarbonate, can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. If an organic carbon molecule or compound is provided in the culture medium of a microorganism grown phototrophically, it generally cannot be taken up and/or metabolized by the cell for energy and/or typically is not present in an amount sufficient to provide sustainable energy for the growth of the cell culture.

Microorganisms that can be useful in accordance with the methods of the present invention can be found in various locations and environments throughout the world. Without being bound by theory, it is observed that, perhaps as a consequence of their isolation from other species and/or their evolutionary divergence, the particular growth medium for optimal growth and generation of lipid and/or hydrocarbon constituents can vary. In some cases, certain strains of microorganisms may be unable to grow in a particular growth medium because of the presence of some inhibitory component or the absence of some essential nutritional requirement required by the particular strain of microorganism.

Solid and liquid growth media are generally available from a wide variety of sources, as are instructions for the preparation of particular media suitable for a wide variety of strains of microorganisms. For example, various fresh water and salt water media can include those described in Barsanti (2005) *Algae*: Anatomy, Biochemistry & Biotechnology, CRC Press for media and methods for culturing *algae*. Algal media recipes can also be found at the websites of various algal culture collections, including, as nonlimiting examples, the UTEX Culture Collection of *Algae* (sbs.utexas.edu/utex/media.aspx); Culture Collection of *Algae* and Protozoa (ccap.ac.uk/media/pdfrecipes); and Katedra Botaniky (/botany.natur.cuni.cz/algo/caup-media.html).

In some embodiments, media used for culturing an organism that produces fatty acids can include an increased concentration of a metal (typically provided as a salt and/or in an ionic form) such as, for example, sodium, potassium, magnesium, calcium, strontium, barium, beryllium, lead, iron, nickel, cobalt, tin, chromium, aluminum, zinc, copper, or the like, or combinations thereof (particularly multivalent metals, such as magnesium, calcium, and/or iron), with respect to a standard medium formulation, such as, for example, standard BG-11 medium (ATCC Medium 616, Table 5), or a modified medium such as ATCC Medium 854 (BG-11 modified to contain vitamin B12) or ATCC Medium 617 (BG-11 modified for marine cyanobacteria, containing additional NaCl and vitamin B12).

For example, a medium used for growing microorganisms that produce free fatty acids can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of metal (e.g. calcium) as compared to a standard medium. The medium used for growing microorganisms that can produce free fatty acids can include, for example, at least about 0.5 mM, between about 0.5 mM and about 1 mM, between about 1 mM and about 2 mM, between about 2 mM and about 5 mM, between about 5 mM and about 10 mM, between about 10 mM and about 25 mM, and greater than 25 mM metal (e.g. calcium) in the formulation.

In further embodiments, by using the excess amount of metal (e.g. calcium) in the medium, at least a portion of the fatty acid(s) can be sequestered as soap precipitates, which may result in decreasing the toxic effects of free fatty acid(s). Addition of metal (e.g. calcium) in the medium can additionally or alternately increase the tolerance of microorganism in media with a relatively high concentration of free fatty acids. Additionally or alternately, fatty acid-producing strains can advantageously be more robust with excess metal (e.g. calcium) content. Although the excess component is described herein as a metal, it is contemplated that the component can more generally be described as a carboxylate counterion source, for example an soap-forming counterion source, a metal ion source (noted as "metal" herein), a multivalent (i.e. having a valence of +2 or higher) counterion source, a divalent counterion source, or some combination. Other details regarding this metal/carboxylate counterion source are described in the co-pending, commonly-assigned U.S. patent application Ser. No. 13/324,636, entitled "Culturing a Microorganism in a Medium with an Elevated Level of a Carboxylate Counterion Source", filed on Dec. 13, 2011.

The culture methods can include inducing expression of a particular gene described herein for the production of free fatty acids and/or fatty acid derivative, and/or regulating metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the recombinant microorganisms can be cultured in a bioreactor. "Bioreactor" refers to an enclosure or partial enclosure in which cells are cultured, optionally in suspension and, when suspended, preferably in an aqueous liquid. The bioreactor can be used to culture microalgal cells through the various phases of their physiological cycle. Bioreactors can offer many advantages for use in heterotrophic growth and propagation methods. To produce biomass for use in food, microorganisms are preferably fermented in large quantities in liquid, such as in suspension cultures as an example. Bioreactors such as steel fermentors can accommodate very large culture volumes (40,000 liter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g. bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Cells can additionally or alternately be cultured in a bioreactor equipped with an artificial light source, a "photobioreactor", and/or can have one or more walls that is transparent enough to light, including sunlight, to enable, facilitate, and/or maintain acceptable microorganism growth. For production of fatty acids and/or fatty acid derivatives, photosynthetic microorganisms can additionally or alternately be cultured in shake flasks, test tubes, vials, microtiter dishes, petri dishes, or the like, or combinations thereof.

Further additionally or alternately, genetically engineered photosynthetic microorganisms may be grown in ponds, canals, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose vis-à-vis the growth and/or survival of the microorganisms.

The methods include culturing a host microorganism, such as a photosynthetic microorgansism, such as, for example, a cyanobacterium, that includes a transcription factor domain protein as described herein to produce at least one fatty acid or fatty acid derivative, in which the method results in production of at least about 5%, 8%, 10%, 15%, 20%, 30%, 40%, 50%, 60%, 70%, 80%, 90%, 100%, 150%, or 200% more than the amount of the fatty acid or fatty acid derivative produced by a microorgansim not including the exogenous gene encoding the transcription factor domain protein, but identical in all other respects, cultured under identical conditions. Additionally or alternately, the methods include at least about 290 mg, at least about 300 mg, at least about 350 mg, at least about 400 mg, or at least about 440 mg per liter of culture of a fatty acid or fatty acid derivative by culturing the recombinant microorganisms described herein. The free fatty acid derivative can be, for example, a fatty aldehyde, a fatty alcohol, a wax ester, an alkene, and/or an alkane.

Fatty acids and fatty acid derivatives can be recovered from culture by recovery means known to those of ordinary skill in the art, such as by whole culture extraction, for example, using organic solvents. In some cases, recovery of fatty acids or fatty acid derivatives can be enhanced by homogenization of the cells, as provided in the examples herein. When fatty acids and/or fatty acid derivatives are sufficiently released from the microorganisms into the culture medium, the recovery method can be adapted to efficiently recover only the released fatty acids and/or fatty acid derivatives, only the fatty acids and/or fatty acid derivatives produced and stored within the microorganisms, or both the produced and released fatty acids and/or fatty acid derivatives.

Free fatty acids and/or fatty acid derivatives secreted/released into the culture medium by the recombinant microorganisms described above can be recovered in a variety of ways. A straightforward isolation method, e.g. by partition using immiscible solvents, may be employed. In an alternative method, lipids such as fatty acids, fatty acid derivatives, and/or triglycerides can be isolated from *algae* by extraction of the *algae* with a solvent at elevated temperature and pressure, as described in in the co-pending, commonly-assigned U.S. patent application Ser. No. 13/407,817 entitled "Solvent Extraction of Products from *Algae*", filed on Feb. 29, 2012, which is incorporated herein by reference in its entirety. Additionally or alternately, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acids and/or fatty acid derivatives can then be eluted from the particulate adsorbents, e.g. by the use of an appropriate solvent. In such circumstances, one isolation method can include carrying out evaporation of the solvent, followed by further processing of the isolated fatty acids, fatty acid derivatives and lipids, to yield chemicals and/or fuels that can be used for a variety of commercial purposes.

In fatty acid and/or fatty acid derivative production embodiments with recombinant microorganisms having an exogenous nucleic acid molecule comprising a nucleic acid sequence encoding a transcription factor domain protein and/or a thioesterase and/or lipase, the amount of the fatty acid and/or fatty acid derivative produced and/or recovered by the method described herein can advantageously be at least about 290 mg per liter of culture, for example at least about 300 mg per liter of culture, at least about 350 mg per liter of culture, at least about 400 mg per liter of culture, at least about 450 mg per liter of culture. Although many times the goal can be to produce and/or recover as much fatty acid and/or fatty acid derivative as possible, in some instances the amount of the fatty acid and/or fatty acid derivative produced and/or recovered by the method described herein can be limited to about 600 mg or less per liter of culture, for example about 550 mg or less per liter of culture, about 500 mg or less per liter of culture.

Some embodiments of the present invention include overexpressing an exogenous gene encoding a transcription factor domain protein and/or an endogenous thioesterase and/or lipase gene and/or a gene encoding an enzyme for producing a fatty acid derivative in a cell by increasing the gene expression level of the exogenous transcription factor domain protein gene and increasing a produced amount of free fatty acids and/or fatty acid derivatives, compared to a microorganism in which the exogenous thioesterase and/or the lipase has not been introduced and/or has not been overexpressed. Additionally or alternately, the free fatty acids and/or fatty acid derivative produced by the microorganism overexpressing the exogenous transcription factor domain protein gene and/or the endogenous thioesterase gene, lipase gene, or gene for producing a fatty acid derivative can be released into the culture medium. Overexpressing an exogenous transcription factor domain protein gene can include expressing an exogenous transcription factor domain protein gene in a cell where the exogenous transcription factor domain protein gene was absent initially or where the host microorganism initially expressed an endogenous transcription factor domain protein.

In some embodiments of the methods described herein, the level of a free fatty acid and/or fatty acid derivative, for example a C8-C20 free fatty acid, or a C12-C20 free fatty acid, such as, for example, at least one of a C12, C14, C16, and/or a C18 free fatty acid, can be increased in the culture with respect to a culture of a microorganism of the same strain not transformed with the exogenous nucleic acid molecule encoding a transcription factor domain protein. For instance, the introduction of an exogenous gene encoding a transcription factor domain protein that can control (e.g. mediate) production of fatty acids can increase the yield in free fatty acid and/or fatty acid derivative production by the recombinant microorganism that is increased by at least 50% (e.g. by at least 75%, by at least 100%, by at least 125%, by at least 150%, by at least 175%, by at least 200%, by at least 225%, by at least 250%, by at least 275%, by at least 300%, by at least 325%, by at least 350%, by at least 375%, by at least 400%, by at least 425%, by at least 450%, by at least 475%, by at least 500%, by at least 525%, by at least 550%, by at least 575%, by at least 600%, by at least 625%, by at least 650%, by at least 675%, by at least 700%, by at least 725%, by at least 750%, by at least 775%, by at least 800%, by at least 825%, by at least 850%, by at least 875%, by at least 900%, by at least 925%, by at least 950%, by at least 975%, or by at least 1000%) over a production of a non-recombinant microorganism, a microorganism into which the exogenous gene has not been introduced, a microorganism in which the exogenous gene has not been overexpressed.

The invention additionally or alternately includes a method of producing a free fatty acid and/or fatty acid derivative using a recombinant microorganism, in which the free fatty acid and/or fatty acid derivative is optionally released into the growth media, comprising culturing a recombinant microorganism that includes at least one exogenous gene encoding a transcription factor domain protein operably linked to a promoter, wherein the microorganism produces at least one free fatty acid and/or fatty acid derivative. In some methods, the microorganism is a cyanobacterium. In some methods, the microorganism has a disrupted acyl-ACP synthetase gene. In various embodiments, at least one free fatty acid or fatty acid derivative is recovered from the cells, the media, or the whole culture.

Additionally or alternately, the present invention can include one or more of the following embodiments.

Embodiment 1

An isolated nucleic acid molecule comprising a nucleic acid sequence encoding a transcription factor domain protein comprising an amino acid sequence having at least 60%, 65%, 70%, 75%, 80%, 85%, 90%, 95%, 99%, or 100% sequence identity to SEQ ID NO:2, SEQ ID NO:4, SEQ ID NO:6, SEQ ID NO:10, or SEQ ID NO:12.

Embodiment 2

An isolated nucleic acid molecule according to claim 1, wherein expression of the a nucleic acid sequence encoding a transcription factor domain protein in a photosynthetic microorganism engineered for the production of a free fatty acid or fatty acid derivative results in production of a higher level of the fatty acid or fatty acid derivative than in a control photosynthetic microorganism identical in all respects except that the control photosynthetic microorganism does not express a nucleic acid sequence encoding a transcription factor domain protein comprising an amino acid sequence having at least 60%, 65%, 70%, 75%, 80%, 85%, 90%, 95%, 99%, or 100% sequence identity to SEQ ID NO:2, SEQ ID NO:4, SEQ ID NO:6, SEQ ID NO:10, or SEQ ID NO:12.

Embodiment 3

An isolated nucleic acid molecule according to embodiment 1 or embodiment 2 comprising a nucleic acid sequence encoding a polypeptide wherein:
the polypeptide belongs to a pfam of the helix-turn-helix (HTH) clan of DNA binding domain proteins (pfam clan CL0123) or a two-component signaling system; and/or
the polypeptide is a member of a pfam selected from the group consisting of Pfam PF01022 (the bacterial regulatory protein, arsR family), Pfam PF00325 (the bacterial regulatory protein, crp family), Pfam PF02742 (the iron dependent repressor, metal binding and dimerization domain family), Pfam PF00356 (the bacterial regulatory protein, lacI family), Pfam PF04967 (the HTH 10 DNA binding domain family), Pfam PF12323 (the HTH 14 OrfB IS605 helix-turn-helix domain family), Pfam PF01418 (the HTH 6 helix-turn-helix domain rpiR family), Pfam PF00165 (the AraC family), Pfam PF05043 (the Mga family), Pfam PF09012 (the FeoC family), Pfam PF00196 (the GerE luxR family), Pfam PF04703 (the FaeA family), Pfam PF01371 (the Trp Repressor family), Pfam PF01037 (the AsnC trans regulator family), Pfam PF00376 (the MerR family), Pfam PF00440 (the TetR N, bacterial regulatory proteins family), Pfam PF02863 (the Arg repressor C family), Pfam PF08220 (the DeoR-like family), Pfam PF00392 (the gntR family), Pfam PF01726 (the LexA family), Pfam PF01638 (the Hx1R family), Pfam PF00126 (the HTH 1 lysR family), Pfam PF01475 (the ferric uptake regulator (FUR) family), Pfam PF01047 (the MarR family), Pfam PF02082 (the Rff2 family), Pfam PF07730 (HisKA 3, histidine kinase family), Pfam PF07536 (the HWE HK histidine kinase family), Pfam PF00512 (the HisKA His Kinase A (phosphor-acceptor) domain family), Pfam PF07568 (the HisKA 2, histidine kinase family), Pfam PF02518 (tye HATPase c histidine kinase, DNA gyrse B, and HSP90-like ATPase), Pfam PF00072 (the response reg family) and Pfam PF06490 (the FleQ family).

Embodiment 4

An isolated nucleic acid molecule according to embodiments 1-3, wherein the isolated nucleic acid molecule encodes a polypeptide comprising an amino acid sequence having at least 70%, 75%, 80%, 85%, 90%, 95%, 99%, or 100% sequence identity to SEQ ID NO:2, preferably wherein the encoded polypeptide recruits to pfam PF02518.

Embodiment 5

An isolated nucleic acid molecule according to any of embodiments 1-3, wherein the isolated nucleic acid molecule encodes a polypeptide comprising an amino acid sequence having at least 65%, 70%, 75%, 80%, 85%, 90%, 95%, 99%, or 100% sequence identity to SEQ ID NO:4, preferably wherein the polypeptide recruits to Pfam PF00072.

Embodiment 6

An isolated nucleic acid molecule according to any of embodiments 1-3, wherein the isolated nucleic acid molecule encoding a polypeptide comprising an amino acid sequence having at least 60%, 65%, 70%, 75%, 80%, 85%, 90%, 95%, 99%, or 100% sequence identity to SEQ ID NO:6, preferably wherein the polypeptide recruits to Pfam PF00440.

Embodiment 7

An isolated nucleic acid molecule according any of embodiments 1-3, wherein the isolated nucleic acid molecule encoding a polypeptide comprising an amino acid sequence having at least 85%, 90%, 95%, 99%, or 100% sequence identity to SEQ ID NO:10, preferably wherein the polypeptide recruits to Pfam PF00216.

Embodiment 8

An isolated nucleic acid molecule according to any of embodiments 1-3, wherein the isolated nucleic acid molecule encoding a polypeptide comprising an amino acid sequence having at least 85%, 90%, 95%, 99%, or 100% sequence identity to SEQ ID NO:12, preferably wherein the polypeptide recruits to pfam PF00376.

Embodiment 9

An isolated nucleic acid molecule according to any of embodiments 1-3, wherein one or more of the following are satisfied: the isolated nucleic acid molecule comprises a nucleic acid sequence having at least 50%, 55%, 60%, 65%, 70%, 75%, 80%, 85%, 90%, or 95% identity to SEQ ID NO:1, SEQ ID NO:3, SEQ ID NO:5, SEQ ID NO:9, or SEQ ID NO:11; the nucleic acid molecule is operably linked to one or more expression control elements; and the photosynthetic microorganism is a cyanobacterium.

Embodiment 10

A vector comprising the isolated nucleic acid molecule of any of embodiments 1-9.

Embodiment 11

The vector of embodiment 10, wherein any combination of the following is or are satisfied: the vector is an integration vector; the nucleic acid is under control of an inducible promoter; or the promoter is selected from the group consisting of: a lac promoter, a tac promoter, a trc promoter, a trcE promoter, a trcY promoter, a tet promoter, a trp promoter, a hybrid promoter that includes either or both of portions of a tet, trp, or lac promoter, an ara promoter, a rha promoter, an AraC promoter, a pBad promoter, an rbc promoter, psbA promoter, a psaAB promoter, a Pm promoter, a NtcA promoter, a gln promoter, a glnA promoter, a nar, a ntc, a nir, a nrt promoter, a pho promoter, a pst promoter, an nrs promoter, a petE promoter, a metallothionien promoter, a nir promoter, a nar promoter, a pho promoter, a cys promoter, an ftf promote, ra heat shock promoter, a cold-inducible promoter, a neomycin phosphotransferase promoter, a chloramphenicol acetyltransferase promoter, a spectinomycin adenyltransferase promoter, or a viral promoter.

Embodiment 12

A cyanobacterium comprising an exogenous nucleic acid molecule encoding a transcription factor domain protein, wherein the cyanobacterium produces a greater amount of at least one free fatty acid or at least one fatty acid derivative than does a cyanobacterium that does not contain an exogenous nucleic acid molecule encoding the transcription factor domain protein.

Embodiment 12

A cyanobacterium according to embodiment 11, wherein the nucleic acid sequence encodes a cyanobacterial transcription factor domain protein, optionally wherein the transcription factor domain protein is a homologous protein, wherein the transcription factor domain protein is overexpressed in the cyanobacterium.

Embodiment 13

The cyanobacterium of embodiment 11, wherein the transcription factor domain protein is a heterologous protein.

Embodiment 14

The cyanobacterium of embodiment 11, wherein the transcription factor domain protein comprises an amino acid sequence having at least about 60%, 65%, 70%, 75%, 80%, 85%, 90%, 95%, 99%, or 100% sequence identity to SEQ ID NO:4, SEQ ID NO:6, SEQ ID NO:10, SEQ ID NO:12, SEQ ID NO:14, or SEQ ID NO:16, wherein the cyanobacterium produces a greater amount of at least one free fatty acid as does a cyanobacterium that does not contain an exogenous nucleic acid molecule encoding the transcription factor domain protein.

Embodiment 15

The cyanobacterium of embodiment 11, wherein one or more of the following are satisfied: the exogenous nucleic acid molecule further comprises a promoter operably linked to the sequence encoding the transcription factor domain protein; the cyanobacterium further comprises a nucleic acid molecule encoding a thioesterase and/or a polypeptide having lipolytic activity; the cyanobacterium further comprises at least one additional exogenous gene, wherein at least one additional exogenous gene encodes a protein for production of a fatty acid or a fatty acid derivative.

Embodiment 16

The cyanobacterium of embodiment 15, wherein the thioesterase is selected from a group consisting of an acyl-ACP thioesterase, an acyl-CoA thioesterase, and a hydroxylbenzoyl thioesterase; the polypeptide having lipolytic activity is a member of Pfam AB Hydrolase clan CL0028, Pfam PF01674, Pfam PF01764, Pfam PF07819, Pfam PF03583, Pfam PF00151 Pfam 00151, Pfam PF00561, Pfam PF02230, Pfam PF07859, Pfam PF08386, Pfam PF12695, Pfam PF12697, Pfam PF12715, Pfam PF04083 or Pfam PF01425 (Amidase); or both.

Embodiment 17

The cyanobacterium of embodiment 15, wherein the cyanobacterium further comprises at least one additional exogenous gene encoding a protein for production of a fatty acid or a fatty acid derivative selected from the group consisting of an acetyl CoA carboxylase, a ketoacyl-CoA synthase, an acyl-CoA synthetase, a fatty acyl-CoA/aldehyde reductase, an alcohol-forming fatty acyl-CoA reductase, a fatty aldehyde-forming fatty acyl-CoA reductase, an acyl-ACP reductase, a carboxylic acid reductase, a fatty acid elongase, a fatty aldehyde reductase, an alcohol acetyl transferase, an acyl-CoA alcohol transacylase, an acyltransferase, a wax synthase, a fatty aldehyde decarbonylase, or a fatty acid decarboxylase.

Embodiment 18

A cyanobacterium according to any of embodiments 11-17, wherein the cyanobacterium is selected from a group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* and *Xenococcus*.

Embodiment 19

A method of producing a fatty acid or fatty acid derivative, the method comprising culturing the cyanobacterium of any of embodiments 11-18 under conditions in which the nucleic acid molecule is expressed to produce at least one fatty acid or fatty acid derivative.

Embodiment 20

The method of embodiment 20, wherein the amount of the fatty acid produced is at least about 290 mg per liter of culture, at least about 300 mg per liter of culture, at least about 350 mg per liter of culture, at least about 400 mg per liter of culture, or at least about 450 mg per liter of culture.

Embodiment 21

The method of embodiment 20, wherein the amount of fatty acid produced is equal to or less than about 600 mg per liter of culture, equal to or less than about 550 mg per liter of culture, or equal to or less than about 500 mg per liter of culture.

Embodiment 22

The method of embodiment 19, wherein the amount of the fatty acid or fatty acid derivative produced is at least 10%, at least 15%, at least 20%, at least 25%, at least 30%, at least 40%, at least 50%, at least 60%, at least 65%, at least 70%, at least 80%, at least 90%, at least 95%, or at least 100% greater than the amount of free fatty acid or fatty acid derivative produced by a cyanobacterium identical in all respects except that it does not include an exogenous nucleic acid molecule encoding a transcription factor domain protein.

Embodiment 23

The method of embodiment 22, wherein the amount of the fatty acid produced is between about 10% and about 200%, between about 10% and about 100%, or between about 10% and about 80%, or between about 10% and about 70%, or between about 10% and about 65% greater than the amount of free fatty acid or fatty acid derivative produced by a cyanobacterium identical in all respects except that it does not include an exogenous nucleic acid molecule encoding a transcription factor domain protein.

Embodiment 24

A method according to any of embodiments 19-23, wherein the medium used for culturing the fatty acid-producing organism can include an increased concentration of a saponifying ion source (e.g. an inorganic saponifying ion source, a metal ion source, a multivalent metal ion source, a divalent metal ion source, or some combination thereof, such as sodium, potassium, magnesium, calcium, iron, or combinations thereof, particularly multivalent metals, such as magnesium, calcium, and/or iron), with respect to a standard medium formulation (e.g. standard BG-11 medium) or a modified medium (e.g. ATCC Medium 854 or ATCC Medium 617), which increased concentration can optionally be at least about 0.5 mM (e.g. between about 0.5 mM and about 1 mM, between about 1 mM and about 2 mM, between about 2 mM and about 5 mM, between about 5 mM and about 10 mM, between about 10 mM and about 25 mM, and/or greater than 25 mM) and/or can optionally but preferably be at least 2-fold (e.g. at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold) as compared to said standard/modified medium.

Embodiment 25

A method according to any of embodiments 19-24, wherein the fatty acid or fatty acid derivative is recovered from the cells, from the media, or from the whole culture.

Without further description, it is believed that one of ordinary skill in the art can, using the preceding description and the following illustrative examples, make and utilize the present invention and practice the claimed methods. The following working examples, therefore, specifically point out representative embodiments of the present invention, some preferred, and are not to be construed as limiting in any way the remainder of the disclosure.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and/or alterations can be employed without departing from the scope of the presently disclosed subject matter.

Example 1

Identification of Putative Transcription Factor Genes Proximal to Fatty Acid Biosynthesis Genes The genomes of proprietary cyanobacterial strains and two environmental metagenomes isolated from various locations within California were examined for the presence of genes sequences that encoded sequences having transcription factor domains. The entire set of sequences predicted to encode proteins with transcription factor domains from each genome and metagenome were queried against the Pfam database using the FastHMM version 1.2 algorithm and then predicted protein sequences recruiting to a delineated subset of Pfams (over 200 Pfam models) were selected. Regions of the genomes and metagenomes that included sequences predicted to encode proteins having transcription factor domains were analyzed for the presence of sequences predicted to encode enzymes that catalyzed reactions in fatty acid or lipid biosynthesis pathways. Sequences encoding domains that recruited to about 80 Pfam domain accessions corresponding to fatty acid and lipid metabolism genes were identified using the FastHMM algorithm. A putative transcription factor domain protein (TFDP) open reading frame (ORF) was characterized as being proximal to putative fatty acid or lipid biosynthesis genes if the predicted TFDP ORF was located on the same strand and was separated by no more than three likely genes from a putative fatty acid or lipid biosynthesis gene or if the predicted TFDP ORF was on the opposite strand from a putative fatty acid or lipid biosynthesis gene with no more than one possible gene intervening between the putative TF ORF and fatty acid or lipid biosynthesis gene. By identifying putative transcription factor genes that were proximal to fatty acid or lipid biosynthesis or modification enzymes, potential fatty acid pathway-related transcription factors were identified. The putative transcription factor identification numbers are provided in Table 1, along with the pfam designation and description of the domain, and the bit score and e value for their relatedness to the pfam. In each case, bit score is greater than the gathering cutoff specified by the pfam database for the particular pfam.

TABLE 1

Putative transcription factor ORF proximal to likely fatty acid or lipid biosynthesis genes

| Gene ID | Pfam ID | Description | E-value |
|---|---|---|---|
| Library003-*Leptolyngbya* sp. | | | |
| 2645 (SEQ ID NO: 1) | PF02518 | Histidine kinase-, DNA gyrase | 7.80E−08 |
| 2651 (SEQ ID NO: 3) | PF00072 | Response regulator receiver domain | 2.2E−20 |
| 8896 (SEQ ID NO: 5) | PF00440 | Bacterial regulatory protein, tetR family | 4.5E−15 |
| Library472-*Thermosynechococcus* sp. | | | |
| 66707 (SEQ ID NO: 7) Metagenome 279 | PF00990 | GGDEF domain | 5.80E−63 |
| 31043 (SEQ ID NO: 9) | PF00216 | Bacterial DNA-binding protein | 1.50E−37 |
| 31046 (SEQ ID NO: 11) | PF00376 | MerR family regulatory protein | 3.00E−05 |
| Library004-*Synechococcus* sp. | | | |
| 43495 (SEQ ID NO: 13) | PF00072 | Response regulator receiver domain | 3E−44 |
| Library272-*Synechococcus* sp. | | | |
| 54379 (SEQ ID NO: 15) | PF00072 | Response regulator receiver domain | 9.4E−44 |
| Library276-*Cyanobacterium* sp. | | | |
| 97362 (SEQ ID NO: 17) | PF00072 | Response regulator receiver domain | 4.9E−34 |
| Library001-*Synechocystis* sp. | | | |
| 122182 (SEQ ID NO: 19) | DUF1821 | Domain of unknown function | 3.40E−86 |

Example 2

Cloning of Putative Transcription Factor Genes in Expression Vectors

Putative transcription factor genes 2645 (SEQ ID NO:1), 2651 (SEQ ID NO:3), 8896 (SEQ ID NO:5), 66707 (SEQ ID NO:7), 31043 (SEQ ID NO:9), 43495 (SEQ ID NO:13), 54379 (SEQ ID NO:15), 97362 (SEQ ID NO:17), and 122182 (SEQ ID NO:19), were cloned into expression vector pSGI-YC28 which contains the TrcE promoter from pTrcHisA (Invitrogen) the lacIq gene, and homology arms that enable integration of the expression cassette into the "RS1" site of the *Synechocystis* PCC 6803 genome (Williams (1988) Methods Enzymol. 167, 766-778).

Figure 2:
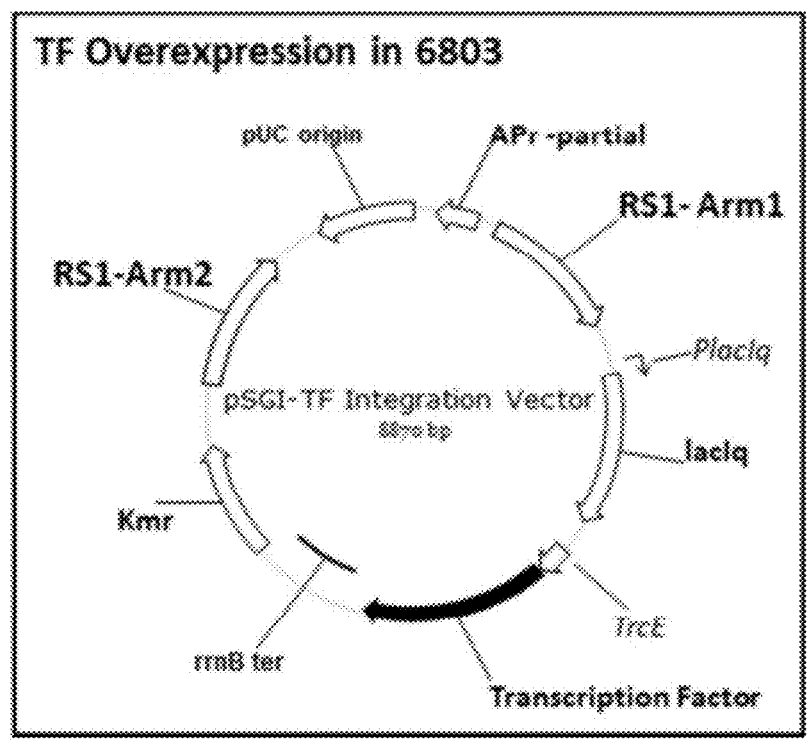
FIG. 2: Diagram of the pSGI-TF integration vector used for site specific integration of transcription factors in cyanobacteria. The vector includes a kanamycin marker and the inducible TrcE promoter for expression of transcription factor domain proteins.

The RS1 upstream (RS1-up) and downstream (RS1-down) fragments were amplified from *Synechocystis* PCC 6803 genomic DNA by the following primer pairs: For RS1-up, the primers RS6803-(ATTGCTGAAGCGGAATCCCTG; SEQ ID NO:27) and RSMCS-3 (CATGGAGATCTGAGCTCG-CATGCATATGGTACCATATAACCAT-CAAAGCCATAGTTGG; SEQ ID NO:28) were used, and for RS1-down, the primers RSMCS-5 (ATATGCATGC-GAGCTCAGATCTCCATGGAATTCGGTAC-CGGTATGGATGGCACCGATG; SEQ ID NO:29) and RS6803-3 (TGGGGGACCATTCTCTGGATC; SEQ ID NO:30) were used. The complete RS1 sequence was re-amplified by the end primers, RS6803-5 (SEQ ID NO:27) and RS6803-3 (SEQ ID NO:30), using the RS1-up and RS1-down fragments as the templates. The re-amplified 2-kb RS1 complete sequence was then ligated into the pUC118 backbone to make pSGI-YC02. A DNA fragment carrying the kanamycin resistance gene and the rrnB terminator, 1579-KmR that was amplified from another cyanobacterial vector by primers NS2-5MCS (GCATGCGAGCTCAGATCTACCAGGT-TGTCCTTGGCGCAG; SEQ ID NO:31) and NS21-3MCS (CCATACCGGTACCGAATTCGCCACGT-TACTGCTCGATGG; SEQ ID NO:32), was inserted between EcoRI and BglII sites on pSGI-YC02. An EcoRI fragment containing the lacIq gene from pTrcHis A (Invitrogen) was inserted into the EcoRI site of the pSGI-YC02 RS1 vector, between the RS1 "down" sequence and the 1579-KmR fragment. The trcE promoter (SEQ ID NO:33) was inserted between SpeI and NcoI sites of the RS1 vector to allow for regulation using this IPTG-inducible promoter. This vector, referred to as pSGI-YC28, replicates autonomously in *E. coli* and allows gene expression in both *E. coli* and *Synechocystis* sp. (FIG. 2).

The putative transcription factor genes were amplified from genomic or metagenomic libraries using primers that included regions of homology to the insertion site of the vector, such that the synthesized genes had vector-homologous sequences at either end. All amplifications were completed with New England Biolabs Phusion DNA Polymerase. Primers used for gene amplification are listed in are listed in Table 2.

TABLE 2

Primers for amplifying genes from genomic and metagenomic DNA

| Gene of Interest | Forward Primer | Reverse Primer |
|---|---|---|
| 2645 | ATGAAGACTGAACTTCACGTTC CGAG (SEQ ID NO: 34) | TCTGGATGATTGTGCTGACATTTCTA (SEQ ID NO: 35) |
| 2651 | ATGAGGCGAGAAAAACTCAAG CTGTTG (SEQ ID NO: 36) | GAGAACCTCCAGAGACAGAATCGTTT GATC (SEQ ID NO: 37) |
| 8896 | ATGCCTACCCCACGCAACTCGA (SEQ ID NO: 38) | TTTAGCAATTGACCGAGGTGGCTGAT (SEQ ID NO: 39) |
| 66707 | ATGGTTAGCCGTCAAGGGTATA GATTC (SEQ ID NO: 40) | CAAAACCGATAGCGCTCAACCAG (SEQ ID NO: 41) |
| 31043 | GTGGCAGGAGAGTTCACGATG (SEQ ID NO: 42) | CCCCCCGCTCACGATCCGGTCGCGCA GCATCT (SEQ ID NO: 43) |
| 31046 | ATGACGGTCGGTCCGGAGAA (SEQ ID NO: 44) | GCAATCCTCGTCCAGCGCCGCCTGCA (SEQ ID NO: 45) |
| 97362 | ATGTCTCGAATACTCGTAATTG ACGATG (SEQ ID NO: 50) | GTTATCCGTATTCAATTCTAAGCAATA ACCAGC (SEQ ID NO: 51) |
| 43495 | TTGGAAAATCGCAAGGAAAAA ATCCT (SEQ ID NO: 46) | TCGCGTGATTAACGGCCTTCTT (SEQ ID NO: 47) |
| 54379 | TTGGAAAATCGCAAGGAAAAA ATCC (SEQ ID NO: 48) | TCTAGCGGCCTTCTTCACCTGG (SEQ ID NO: 49) |
| 122182 | ATGCCTGGGGCCGGTTCA (SEQ ID NO: 52) | AAACACGCTCTAAGCGCCGTAT (SEQ ID NO: 53) |

The amplified gene fragments were then combined in a 1:1 ratio with two linear pSGI-YC28 fragments, each of which had homology to one end of the gene fragment (by incorporation of vector homologous sequences into the primers used to amplify the genes).

TABLE 3

Primers for generating YC28 shuttle vector backbone fragments for ligation

| Fragments of Interest | Forward Primer Name | Forward Primer Sequence | Reverse Primer Name | Reverse Primer |
|---|---|---|---|---|
| YC28-Fragment 1 | E65 | GGTTTATTCCTCCTTAT TTAATCGATAC (SEQ ID NO: 54) | E87 | GACGAGCATCACAA AAATCGAC (SEQ ID NO: 55) |
| YC28-Fragment 2 | E66 | TAATGATAGGATCCGA GCTCAGATC (SEQ ID NO: 56) | E88 | GTCGATTTTTGTGAT GCTCGTC (SEQ ID NO: 57) |

The vector and transcription factor gene fragments were ligated using the BPS Bioscience Inc. QUICK PCR cloning kit. Vector fragments were added at a 1:1 ratio to gene fragments with a final DNA concentration of 150 ng/10 µL reaction. The mix was incubated at room temperature for 30 minutes to overnight.

Ligated constructs were transformed into *E. coli*-K19 cells that carried the Cc1FatB1 thioesterase gene in the pSGI-YC63 vector that includes RS2 *Synechocystis* integration sites, a TrcY promoter for driving expression of the Cc1FatB1 gene, and a spectinomycin/streptomycin resistance gene. *E. coli*-K19 lacks a functional FadE (acyl-CoA dehydrogenase) gene, which functions in the fatty acid degradation pathway.

The pYC vector for expressing the N-terminally truncated Cc1FatB1 *Cuphea carthagenensis* thioesterase gene (SEQ ID NO:81; WO 2011/008565, herein incorporated by reference) was derived from a pUC19 backbone, which includes a bacterial origin of replication for maintenance of the plasmid in *E. coli*. The pYC vector included the RS2 "up" (5') and RS2 "down" (3') sequences from the *Synechocystis* genome for homologous recombination (Williams (1988) *Methods in Enzymology* 167, 766-778). In addition, the expression vector included an omega-Sp cassette providing spectinomycin resistance, and the isopropyl β-D-1-thiogalactopyranoside (IPTG)-inducible trcY promoter (SEQ ID NO:83).

The pYC63 vector was constructed by amplifying the RS2 integration site sequence from *Synechocystis* PCC 6803 genomic DNA using the primers: RS2-5 (GGGC-CCTATTTGCCCGTATTCTGCCCTATCC; SEQ ID NO:58) and RS2-3 (GGGCCCGACTGCCTTTGGTGGTATTAC-CGATG; SEQ ID NO:59). Plasmid pUC19 was digested with HindIII and EcoRI to remove the multiple cloning site (MCS), and then treated with T4-DNA polymerase to blunt the ends. The RS2 sequence (comprising RS2 up and RS2 down, 1.8 kb) was ligated then into the pUC19 backbone. The resulting plasmid was named pYC34. The pYC34 plasmid was digested then with BglII, which cut within the RS2 sequence, opening up the integration site. A copy of the omega-Sp cassette (BamHI fragment) was ligated into the BglII site of pYC34 to make pYC36. The pYC36 plasmid was digested with FspI to remove the majority of the Ampicillin resistance gene ($Amp^R$), making spectinomycin/streptomycin as the only selectable marker. The constructed plasmid was named pYC37. An EcoRI fragment containing the lacIq gene was inserted into the EcoRI site of pYC37, between the RS2 "up" sequence and the omega-Sp cassette to allow for regulation of lac-inducible promoters. The vector further included a TrcY promoter. The TrcY promoter (SEQ ID NO:83) was amplified using the following primers: 4YC-trcY-5 (ACTAGTCCTGAGGCTGAAATGAGCTGT-TGACAATTAATCATCCGGCTCGTATAATGTGTGGA ATTGTGAG; SEQ ID NO:60) and 4YC-trcY-3 (CCATG-GTTTTTTTCCTCCTTAGTGTGAAATTGT-TATCCGCTCACAATTCCACACATTATACGA GCCG-GAT; SEQ ID NO:61) and inserted into the vector digested with SpeI-XbaI. The plasmid was called pYC45.

The Cc1FatB1 *Cuphea carthagenensis* thioesterase gene, codon-optimized for *Synechocystis* (SEQ ID NO:81) and encoding an N-terminally truncated acyl-ACP thioesterase (SEQ ID NO:82), was cloned into the pYC63 expression vector by amplifying the truncated and *Synechocystis* codon-optimized Cc1 FatB1 sequence using primers designed to the 5' and 3' ends of the gene, in which the 5' primer had homology to the region of the pYC vector upstream of the NcoI cloning site, and the 3' primer had homology to the region of the pYC vector downstream of the XbaI cloning site, both downstream of the TrcY promoter. The resulting expression construct had a pUC origin of replication, the truncated and codon-optimized Cc1 FatB1 thioesterase gene cloned downstream of the TrcY promoter and upstream of the T4 terminator and flanked by the RS2 up and RS2 down sequences; the omega-Sp cassette, and the lacIq gene positioned between the RS2 down and RS2 up sequences. The construct was transformed into *Synechocystis* cells and transformants were selected using spectinomycin.

To generate bacterial clones that included a transcription factor gene in Cc1FatB1 strains, 5 µL of the BPS transcription factor domain protein ligation reaction was added to 50 µL of competent pSGI-YC63-Cc1FatB1 cells. Reactions were mixed and cells were incubated on ice for 30 minutes. Each reaction was heat shocked for 30 seconds at 42° C. then replaced on ice. Cells were shaken at 3TC for 1 hour following then plated on selection plates and grown overnight for 14-20 hours.

The colonies were then streaked on a second selective plate and screened with the forward primers provided in Table 2 and reverse primer GTCTAGAGGCCTGTCGACGA (SEQ ID NO:62). All screening was completed with Sigma RedTaq DNA Polymerase. All fragments for sequencing were amplified using New England Biolabs Phusion DNA Polymerase.

Example 3

Expression of Transcription Factor Genes in *E. coli*

*E. coli* cells were grown overnight in 5 mL tubes, with selective media (50 µg/mL kanamycin for selection of the YC28 vector including the putative transcription factor gene, and 50 µg/mL spectinomycin for selection of the YC63 vector including the Cc1 FatB1 gene), on a shaker at 250 rpm, at 30° C. Non-induced or induced (1 mM IPTG final concentration) cultures were 600 µL overnight culture plus 600 µL fresh LB selective media in 96-well 2-mL depth culture plates grown for 6 hours to overnight. Optical density was taken at the start of growth and the end. 600 µL was transferred to 1.5 mL GC-vials for GC-Free Fatty Acid Analysis.

Example 4

Analysis of Fatty Acid Samples from *E. coli*

Free fatty acids were analyzed by gas chromatography (GC) with flame ionization detection (GC-FID). Specifically, 0.6 mL of the *E. coli* cultures were added to 2 mL glass gas chromatography vials with PTFE (polytetrafluoroethylene)-lined caps (National Scientific). Fifty microliters of an internal standard set that included the free fatty acids C9:0, C13:0, and C17:0, each at a concentration of 600 µg/mL, in hexane, were added to the culture sample, followed by 50 microliters of 50% $H_2SO_4$, 100 microliters of 5M NaCl, and 850 microliters of hexane. The final concentration of each internal standard was 50 µg/mL relative to sample volume. The fatty acids for making the internal standard set were purchased from Fluka or Nu-Chek Prep, Inc. The cultures were then vortexed on a multi-tube vortexer at 2,500 rpm for 30 min. The vials were finally centrifuged for 3 min. at 2500 rpm to provide good separation between organic and aqueous phases. The hexane layers were sampled by a Gerstel MPS2L Autosampler. *E. coli* fatty acid samples were analyzed on an Agilent model 7890A gas chromatograph equipped with an FID (flame ionization detector) that included a J&W Scientific DB-FFAP capillary column (15 m length, 0.25 mm internal diameter, 0.25 µm film thickness). The GC oven was programmed as follows: 140° C. for 0.5 min., then heated at 20° C./min. to 230° C. (hold 5 minutes). The injector temperature was kept at 250° C., and a 40:1 split 1.0 µL injection was used. Helium was used as a carrier gas at a flow rate of 1.2 mL/min. The analytes were identified by comparison of retention times to individually injected standards. The calibration range for the analytes was 2 µg/mL to 200 µg/mL for C8:0-C16:1 fatty acids and 0.5 µg/mL to 50 µg/mL for C18:0-C18:2 fatty acids. Spiking and recovery experiments into whole cell culture showed that the extraction method recovered consistently within a range of 85%-115% of each analyte.

Figure 3:
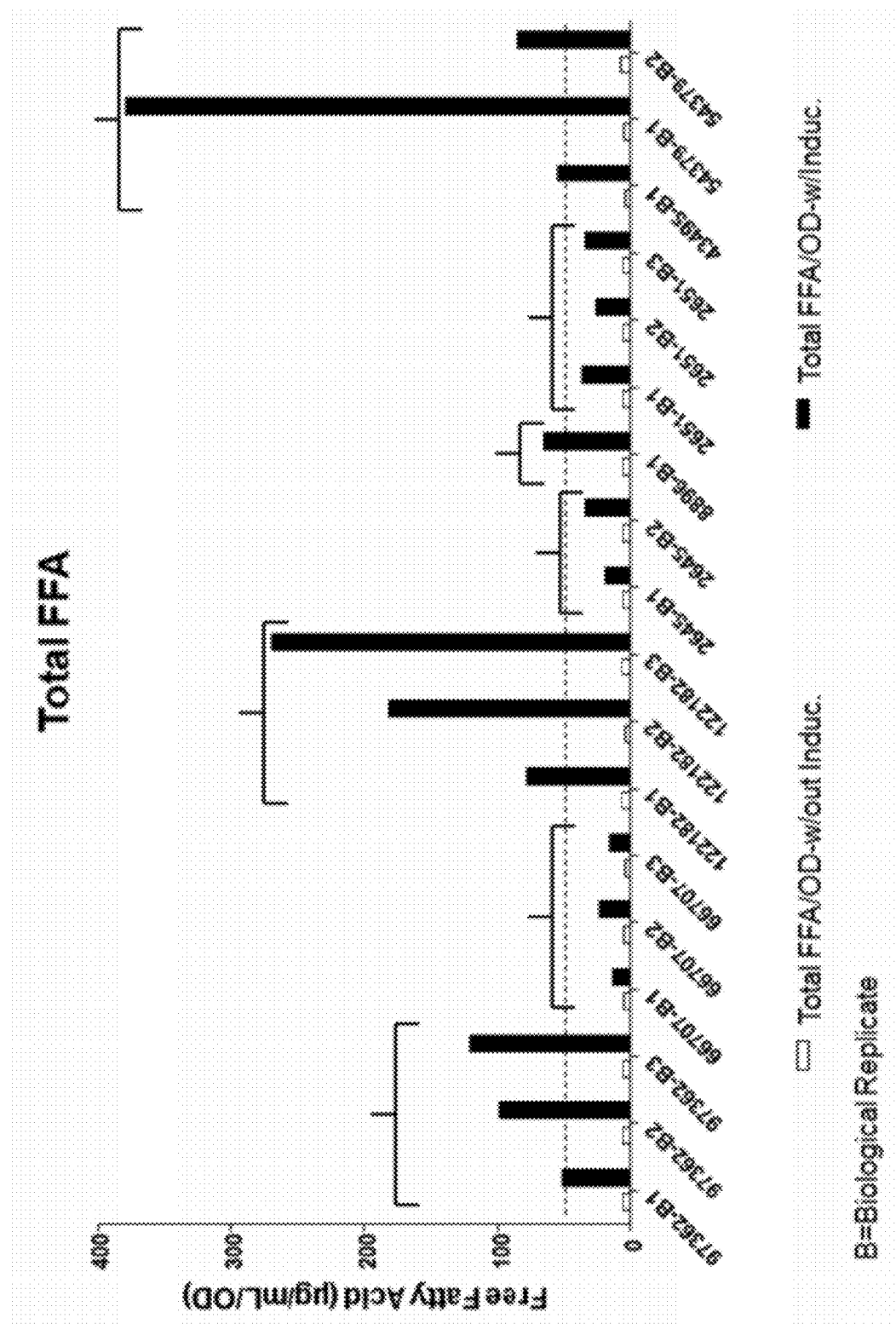
FIG. 3: Graph depicting results of initial free fatty acid screening in *E. coli* K19. The graph shows the amounts of free fatty acids produced by *E. coli* strains expressing putative transcription factors 97362, 66707, 122182, 2645, 8896, 2651, 43495 and 543579 in combination with the Cc1FatB1 thioesterase gene. Putative transcription factors in this experiment were under the control of the inducible promoter TrcE. YC63-1A is the vector that includes the Cc1FatB1 gene, and YC28 is the vector used for cloning the putative transcription factor genes.

Analysis of the results of expressing the putative transcriptional regulator genes in *E. coli* is shown in FIG. 3. Different "B" numbers refer to different transformants ("biological replicates") having the particular gene. The dashed line represents the average level of free fatty acids produced by *E. coli* strains that express the Cc1FatB1 gene from the YC63 vector, but lack an exogenous transcription factor domain protein gene.

Example 5

Transformation of Cyanobacteria

The transcription factor domain protein constructs described in Example 4 were also used to transform a *Synechocystis* sp.PCC 67803 strain that carried the Cc1FatB1 gene that had been introduced into the *Synechocystis* cells on the pYC63 vector used to transform the *E. coli* host cells.

For transforming constructs containing putative transcription factor genes into *Synechocystis* cells having the integrated Cc1FatB1 gene, were grown overnight in 30 mL BG11 to O.D. 0.7-0.9 (730 nm) in 30° C. with constant light. The cells were collected by centrifuging at 3,000 g for 10 minutes. The media was discarded and cells were resuspended in 3 mL fresh BG11. 300 µL of suspension were pipetted into a 1.5 mL tube, adding a maximum volume of 10 μL or maximum amount of 5 μg DNA. Cells were then incubated at 30° C., low light (<50 μE/m$^2$/s) for 5 hours, mixed gently at 21 hours. Cells were then spread on a membrane which was either: a Pall Life Sciences BioTrace NT Nitrocellulose Transfer Membrane: 0.2 μm (pore size), 140 μm (thickness), 82 mm (VWR No. 27377-032, Pall No. P/N 66487), or a GE Osmonics Nitrocellulose Hybridization and Transfer Membrane: 0.22 μm NitroPure, 82 mm (Fisher No. WP2HY08250), or a Whatman Nuclepore Polycarbonate Track-Etched Membrane, PC 47 mm, 0.2 μm (Fisher No. 09-300-69, Whatman No. 111106), or a Millipore MF-Millipore Mixed Cellulose Ester Membrane, MCE 25 mm, 0.025 μm (Fisher No. VSWP-025-00, Millipore Corp No. VSWP02500) on top of a BG11 plate with no antibiotics. Plates were incubated with constant light, and after overnight growth, membranes were transferred to BG11 plates with antibiotic (kanamycin at 20 μg/mL or spectinomycin at 20 μg/mL) for 7-10 days or until colonies appeared.

For screening, colonies were streaked on a second selective plate and screened with the appropriate primers. All screening was performed with Sigma RedTaq DNA Polymerase using the same primers that were used for screening *E. coli*. A second amplification was then gel purified and clean fragment integration was confirmed by sequencing. All fragments for sequencing were amplified using New England Biolabs Phusion DNA Polymerase using the primers as shown in Table 4.

Example 6

Culturing Cyanobacteria

*Synechocystis* cells transformed with the transcription factor expression constructs were diluted to O.D. 0.6 (730 nm) and either grown in selective BG11 (containing 20 μg/mL kanamycin for selection of the YC28 vector insertion including the putative transcription factor gene, and 20 μg/mL spectinomycin for selection of the YC63 vector insertion including the Cc1FatB1 gene) or selective BG11 with 1 mM IPTG, in 10 mL of media in a 20 mL scintillation vial for 6 days, shaking at (150 rpm) at 30° C. with constant illumination (40 μEinsteins m$^{-2}$ sec$^{-1}$).

The ingredients of the BG-11 medium (ATCC medium: 616 Medium BG-11 for blue-green *algae*) are shown in Table 5.

TABLE 5

| ATCC 616 Medium BG-11 for Blue-green Algae | |
|---|---|
| NaNO$_3$ | 1.5 g |
| K$_2$HPO$_4$ | 0.04 g |
| MgSO$_4$ * 7H$_2$O | 0.075 g |
| CaCl$_2$ * 2H$_2$O | 0.036 g |
| Citric acid | 6.0 mg |
| Ferric ammonium citrate | 6.0 mg |
| EDTA | 1.0 mg |

TABLE 4

Primers used in the screening.

| Gene of Interest | Forward Primer | Reverse Primer |
|---|---|---|
| RS1 Integration | ACCCTGGCCCTCAGTGCGAG (SEQ ID NO: 63) | CTACCGTTTGCCGTTCGTTG (SEQ ID NO: 64) |
| RS2 Integration | CCACCGATTCCGTGGTCAGC (SEQ ID NO: 65) | GTACCTATCTCCATCCTGACCGC AG (SEQ ID NO: 66) |
| Cc1FatB1 Integration | ATGGTATGGGTCGTGATTGG (SEQ ID NO: 67) | CTCTTGGCTGACTTCGTAAGG (SEQ ID NO: 68) |
| YC28 Sequencing Primer #1 | CTGACGGGCTTGTCTGCTC (SEQ ID NO: 69) | GAGCAGACAAGCCCGTCAG (SEQ ID NO: 70) |
| YC28 Sequencing Primer #2 | CAGTCGTTGCTGATTGGCGTT (SEQ ID NO: 71) | AACGCCAATCAGCAACGACTG (SEQ ID NO: 72) |
| YC28 Sequencing Primer #3 | CAACAAACCATGCAAATGCTG (SEQ ID NO: 73) | CAGCATTTGCATGGTTTGTTG (SEQ ID NO: 74) |
| YC28 Sequencing Primer #4 | TAGCGCGAATTGATCTGGT (SEQ ID NO: 75) | ACCAGATCAATTCGCGCTA (SEQ ID NO: 76) |
| YC28 Sequencing Primer #5 | TCAGACAATCTGTGTGGGCA (SEQ ID NO: 77) | TGCCCACACAGATTGTCTGA (SEQ ID NO: 78) |
| YC28 Sequencing Primer #6 | TCGTCGACAGGCCTCTAGAC (SEQ ID NO: 79) | GTCTAGAGGCCTGTCGACGA (SEQ ID NO: 80) |

TABLE 5-continued

ATCC 616 Medium BG-11 for Blue-green Algae

| | |
|---|---|
| $Na_2CO_3$ | 0.02 g |
| Trace Metal Mix A5[#] | 1.0 mL |
| Agar (if needed) | (up to) 10.0 g |
| Distilled water | 1.0 L |

[#]Trace Metal Mix A5
$H_3BO_3$ 2.86 g
$MnCl_2 * 4H_2O$ 1.81 g
$ZnSO_4 * 7H_2O$ 0.22 g
$Na_2MoO_4 * 2H_2O$ 0.39 g
$CuSO_4 * 5H_2O$ 0.080 g
$Co(NO_3)_2 * 6H_2O$ 49.4 mg
Distilled water to 1.0 L

Example 7

Analysis of Fatty Acid Samples from Cyanobacteria (*Synechocystis*)

*Synechocystis* fatty acid samples were analyzed on an Agilent model 7890A gas chromatograph equipped with an FID (flame ionization detector) that included a J&W Scientific DB-FFAP capillary column (15 m length, 0.25 mm internal diameter, 0.25 μm film thickness). The gas chromatography oven was programmed as follows: 140° C. for 0.5 minutes, then heated at 20° C./min. to 230° C. (hold 5 minutes). The injector temperature was kept at 250° C., and a 40:1 split 1.0 μL injection was used. Helium was used as a carrier gas at a flow rate of 1.2 mL/min. The analytes were identified by comparison of retention times to individually injected standards. The calibration range for the analytes was 2 μg/mL to 200 μg/mL for C8:0-C16:1 fatty acids and 0.5 μg/mL to 50 μg/mL for C18:0-C18:2 fatty acids.

TABLE 6

Production of Free Fatty acids by Synechocystis transformed with potential Transcription Factor Domain Proteins and a FatB thioesterase gene (YC63-1A)

| Constructs | Total FFA (average) | Standard deviation | FFA per OD (average) | Standard deviation |
|---|---|---|---|---|
| YC63-1A + YC28-2645 + IPTG | 290 | 6.60 | 26.92 | 0.53 |
| YC63-1A + YC28-2651 + IPTG | 404 | 70.86 | 33.08 | 4.36 |
| YC63-1A + YC28-8896 #1 + IPTG | 445 | 255.59 | 50.20 | 22.60 |
| YC63-1A + YC28-8896 #2 + IPTG | 395 | 92.57 | 54.75 | 10.40 |
| YC63-1A + YC28-43495 + IPTG | 352 | 21.42 | 40.96 | 2.12 |
| YC63-1A + YC28-31043 + IPTG | 316 | 4.14 | 33.16 | 0.35 |
| YC63-1A + YC28-54379 + IPTG | 293 | 5.47 | 34.42 | 0.56 |
| YC63-1A + YC28-66707 + IPTG | 266 | 33.27 | 31.43 | 3.48 |
| YC63-1A + YC28-97362 + IPTG | 114 | 2.37 | 17.72 | 0.28 |
| YC63-1A + YC28-122182 #1 + IPTG | 190 | 4.95 | 22.34 | 0.50 |
| YC63-1A + YC28-122182 #2 + IPTG | 187 | 3.92 | 23.06 | 0.34 |
| YC63-1A + YC28-closed (#1) + IPTG | 268 | 3.37 | 28.76 | 0.28 |
| YC28-1A #1 + IPTG | 141 | 5.69 | 11.02 | 0.32 |
| YC28-1A #2 + IPTG | 127 | 9.65 | 11.18 | 0.72 |
| YC28-9-8 Empty Control Vector #1 + IPTG | 6 | 0.26 | 0.47 | 0.01 |
| YC28-9-8 Empty Control Vector #2 + IPTG | 5 | 0.32 | 0.41 | 0.02 |
| YC28-9-8 Empty Control Vector #3 + IPTG | 5 | 0.29 | 0.43 | 0.02 |

Graphs depicting the results of expressing the putative transcriptional regulator genes in *Synechocystis* are shown in FIG. 4, in which the amount of fatty acid produced is provided on a per volume basis, and FIG. 5, in which the amount of fatty acid produced is normalized to the optical density of the cultures. Expression of the transcription factor domain proteins 2651, 8896, 43495, and 31043 in *Synechocystis* strains that also expressed an acyl-ACP thioesterase gene resulted in a higher level of free fatty acids being produced than in control cells that expressed the thioesterase gene but lacked an exogenous transcription factor domain protein gene.

Expression of 2645 was not observed to increase fatty acid production in *Synechocystis*; however, this polypeptide it is a member of the histidine kinase protein family (Table 2). Proteins of this family are typically part of two-component regulatory systems that require a response regulator protein partner for regulating transcription. Gene 2651 is proximal to gene 2645 in the *Leptolyngba* sp. genome and encodes a protein having a response regulator receiver domain. Thus it is hypothesized that these two genes may interact to regulate transcription. It was concluded after further sequence analysis that the polypeptide sequences designated 66707 (SEQ. ID NO:8) and 12282 (SEQ. ID NO:20) were not transcription factor domain proteins.

The invention claimed is:

1. A recombinant cyanobacterium comprising an exogenous nucleic acid molecule encoding a transcription factor domain protein,
wherein the transcription factor domain protein has transcription factor activity and comprises an amino acid sequence having at least 85% amino acid sequence identity to the amino acid sequence of SEQ ID NO:4, SEQ ID NO:6, SEQ ID NO:10, or SEQ ID NO:12, and
wherein the recombinant cyanobacterium produces a greater amount of at least one free fatty acid or at least one fatty acid derivative than does a control cyanobacterium that does not comprise the exogenous nucleic acid molecule encoding the transcription factor domain protein, and
further wherein the exogenous nucleic acid molecule is operably linked to a promoter that is heterologous relative to the cyanobacterium and/or the exogenous nucleic acid molecule.

2. The cyanobacterium of claim 1, wherein the cyanobacterium further comprises a nucleic acid molecule encoding a thioesterase and/or polypeptide having lipolytic activity.

3. The cyanobacterium of claim 1, wherein the cyanobacterium further comprises at least one additional exogenous nucleic acid molecule, encoding a protein for the production of a fatty acid or a fatty acid derivative.

4. The cyanobacterium of claim 3, wherein the cyanobacterium further comprises at least one additional exogenous nucleic acid molecule encoding an enzyme selected from the group consisting of an acetyl CoA carboxylase, a ketoacyl-CoA synthase, an acyl-CoA synthetase, a fatty acyl-CoA/aldehyde reductase, an alcohol-forming fatty acyl-CoA reductase, a fatty aldehyde-forming fatty acyl-CoA reductase, an acyl-ACP reductase, a carboxylic acid reductase, a fatty aldehyde reductase, an alcohol acetyl transferase, an acyl-CoA alcohol transacylase, an acyltransferase, a wax synthase, a fatty aldehyde decarbonylase, and a fatty acid decarboxylase.

5. The cyanobacterium of claim 1, wherein the cyanobacterium is an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Micro cystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus* species.

6. A method of producing a free fatty acid or fatty acid derivative, the method comprising culturing the recombinant cyanobacterium of claim 1 in a growth medium under conditions in which the exogenous nucleic acid molecule encoding the transcription factor domain protein is expressed to produce at least one free fatty acid or fatty acid derivative.

7. The method of claim 6, wherein the cyanobacterium is cultured phototrophically.

8. The method of claim 6, wherein the amount of the fatty acid or fatty acid derivative produced is at least 10% more than the amount of the fatty acid or fatty acid derivative produced by the control cyanobacterium cultured under substantially identical conditions.

9. The method of claim 6, wherein the cyanobacterium is selected from the group consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* and *Xenococcus*.

10. The method of claim 6, further comprising isolating at least one free fatty acid or at least one fatty acid derivative from the cyanobacteria or from the growth medium.

11. An expression cassette comprising a nucleic acid molecule encoding: (a) a polypeptide comprising an amino acid sequence having at least about 85% sequence identity to the amino acid sequence of SEQ ID NO:2, wherein the nucleic acid molecule encoding the polypeptide is operably linked to a heterologous promoter, and wherein the polypeptide has histidine kinase activity; or (b) a polypeptide comprising an amino acid sequence having at least about 85% sequence identity to the amino acid sequence of SEQ ID NO:4, SEQ ID NO:6, SEQ ID NO:10, or SEQ ID NO:12, wherein the nucleic acid molecule encoding a lithe polypeptide is operably linked to a heterologous promoter, and wherein the polypeptide has transcription factor activity.

12. The expression cassette according to claim 11, wherein the nucleic acid molecule encodes a polypeptide comprising an amino acid sequence having at least about 95% sequence identity to the amino acid sequence of SEQ ID NO:2, SEQ ID NO:4, SEQ ID NO:6, SEQ ID NO:10, or SEQ ID NO:12.

13. The expression cassette of claim 11, wherein the promoter is inducible.

14. The expression cassette of claim 11, wherein the expression cassette is in an expression vector.

15. The expression cassette of claim 11, wherein the expression cassette is in an integration vector.

16. The cyanobacterium of claim 1, wherein the cyanobacterium comprises an exogenous nucleic acid molecule encoding a polypeptide having an amino acid sequence with at least about 85% amino acid sequence identity to the amino acid sequence of SEQ ID NO:2 and an exogenous nucleic acid molecule encoding a polypeptide having an amino acid sequence with at least 85% amino acid sequence identity to the amino acid sequence of SEQ ID NO:4.

17. A recombinant cyanobacterium comprising an exogenous nucleic acid molecule encoding a transcription factor domain protein,
   wherein the transcription factor domain protein has transcription factor activity and comprises an amino acid sequence having at least 85% amino acid sequence identity to the amino acid sequence of SEQ ID NO:14 or SEQ ID NO:16, and
   wherein the recombinant cyanobacterium further comprises at least one additional exogenous nucleic acid molecule encoding an enzyme selected from the group consisting of an acetyl CoA carboxylase, a ketoacyl-CoA synthase, an acyl-CoA synthetase, a fatty acyl-CoA/aldehyde reductase, an alcohol-forming fatty acyl-CoA reductase, a fatty aldehyde-forming fatty acyl-CoA reductase, an acyl-ACP reductase, a carboxylic acid reductase, a fatty aldehyde reductase, an alcohol acetyl transferase, an acyl-CoA alcohol transacylase, an acyltransferase, a wax synthase, a fatty aldehyde decarbonylase, and a fatty acid decarboxylase, and
   further wherein the recombinant cyanobacterium produces a greater amount of at least one free fatty acid or at least one fatty acid derivative than does a control cyanobacterium that does not comprise the exogenous nucleic acid molecule encoding the transcription factor domain protein, and
   still further wherein the exogenous nucleic acid molecule is operably linked to a promoter that is heterologous relative to the cyanobacterium and/or the exogenous nucleic acid molecule.

18. The recombinant cyanobacterium of claim 17, wherein the transcription factor domain protein has 100% amino acid sequence identity to the amino acid sequence of SEQ ID NO:14 or SEQ ID NO:16.

* * * * *

```
SEQUENCE LISTING

<160> NUMBER OF SEQ ID NOS: 83

<210> SEQ ID NO 1
<211> LENGTH: 435
<212> TYPE: DNA
<213> ORGANISM: Leptolyngbya sp.

<400> SEQUENCE: 1
atgaagactg aacttcacgt tccgagcgat ttgcgatttc tcacggtagt tgaatcctgg      60
ctattagaga gtctcaaaat tgaaattggc gaccaaattg attggacacg acaatcgagt     120
```

```
cggctacggt tggctttggt tgaggcttac tcaaatgtgg tgcggcatgc ccaccgcaat      180
caaccggatc ttccggtcgt ggtgcgattg gaattgagac atcgagattt agcgatcgag      240
atctgggatc acggacaggg gtttgacatt tcgagctatt tggctccatc tcctgaaatg      300
atgcaagagc atggctatgg ctggctgatt ctgaatcgac tgatggatcg ggtgaatat       360 cagcttcagg tcaatgggcg gaattgtttg aaacttcaag ccaatctgct agaaatgtca      420
gcacaatcat ccaga                                                       435
```

```
<210> SEQ ID NO 2
<211> LENGTH: 145
<212> TYPE: PRT
<213> ORGANISM: Leptolyngbya sp.

<400> SEQUENCE: 2

Met Lys Thr Glu Leu His Val Pro Ser Asp Leu Arg Phe Leu Thr Val
1               5                   10                  15

Val Glu Ser Trp Leu Leu Glu Ser Leu Lys Ile Glu Ile Gly Asp Gln
            20                  25                  30

Ile Asp Trp Thr Arg Gln Ser Ser Arg Leu Arg Leu Ala Leu Val Glu
        35                  40                  45

Ala Tyr Ser Asn Val Val Arg His Ala His Arg Asn Gln Pro Asp Leu
    50                  55                  60

Pro Val Val Val Arg Leu Glu Leu Arg Asp Arg Asp Leu Ala Ile Glu
65                  70                  75                  80

Ile Trp Asp His Gly Gln Gly Phe Asp Ile Ser Ser Tyr Leu Ala Pro
                85                  90                  95

Ser Pro Glu Met Met Gln Glu His Gly Tyr Gly Trp Leu Ile Leu Asn
            100                 105                 110

Arg Leu Met Asp Arg Val Glu Tyr Gln Leu Gln Val Asn Gly Arg Asn
        115                 120                 125

Cys Leu Lys Leu Gln Ala Asn Leu Leu Glu Met Ser Ala Gln Ser Ser
    130                 135                 140

Arg
145
```

```
<210> SEQ ID NO 3
<211> LENGTH: 1638
<212> TYPE: DNA
<213> ORGANISM: Leptolyngbya sp.

<400> SEQUENCE: 3
atgaggcgag aaaaactcaa gctgttgatc gtggatgatg agccggataa tctcgatctg       60
ctttaccgta ccttccggcg agacttcgac gtgattcggg cggaaagcgc gatcgaagcg      120
ctcaaagtcc ttgatgaaca aggcgaagtc gcaattatta tttcagatca gcgaatgcca      180
gaaatgctgg gaactgagtt ctcagtcga accgtcgatc gctttccgga cacgattcgg       240
attgtgctaa cgggctatac cgatgtcgaa gatctcgtcg atgccattaa ctctggcaaa      300
gtattcaaat acatcaccaa gccttggaag tctcaacagc ttcaagtcgt tgtcgagcag      360
gcggctgaga cctatcaagt gctaaaacag cgcacagcgg atttacgacg ggcactcaga      420
cgcgaatcgt cgttgaatgc cattacaacc gcgattcgcg aatcgctgga ttatcaaaac      480
atgctgcaca cgatcgtgga aacgatcggg ctgacctttg aggcaagttg ctgcatgtta      540
catccagtcg aaggtgaacg gttgaaatcc aattcagcca tgtattgtgc agtgaatgtg      600
```

```
cccttcaaga gttgtgaaga cgatcgcact tcagacctgg tacaaatcgt actgcacgat      660
agcacagcca gaatgaagag ccaaaatcca ccgcattttg tgctgccgtt gcgctaccaa      720
aaagacctcc tcgcgattct gtctctgcat cgagaatccg atcagccatt ctggtcaaca      780
gaagacttag aactgatcga agtcgtcaca gaacaagcag ccttggcgat ttctcaagca      840
agactctatc gtcgaactca ggagcaagcg aacaaattc gagccgagtt agaagtcgca       900
cgccagattc agaccaatct cctgcggcag acgcttccgc gattagacaa tcttaaagta      960
caagcttgtt gtcatcccgc tcgtgaagtt ggaggagact tttttgaagt ctatcagcat     1020
ccccaaggcg atttatggct agccgtgggc gatgtctcag gcaagggagt tccggcagct     1080
ctgtttatgg caagtgcgat tccgtgttg cggcgggaat tgtcacaaga gtttctcca      1140 gaaccagatg aagtgatgcg aaatttaaac agcattctct cgcaagactt aatgggcaca     1200 aactgttta ttacaatggt tttagcgcga tacacccgat cgagcggaca attagtttat      1260
gcgaatgcag gtcatatcta cccttagtt tggtcaaagc atacgatcgc gcaagccatt      1320
gagccaactt atttgaaagt ccgaggcatt ccctaggga tattaccgaa atggaacgcg      1380
attgccggaa aacgattgct tcaagatgga gaaatcttat tattaaccag cgatggaatt     1440
actgaggcaa ccgtgcgacc agaaggagaa gtcaatttag cgagcgatcc cgcaagggcg     1500
atgttacgac aaaccgggtt atggaagtta ctacagcaag cgggagaaag tttggatctc     1560
aaacagctgc ttgcccaaat tcaggcgcac aatgcgattc aagaagatga tcaaacgatt     1620
ctgtctctgg aggttctc                                                   1638

<210> SEQ ID NO 4
<211> LENGTH: 546
<212> TYPE: PRT
<213> ORGANISM: Leptolyngbya sp.

<400> SEQUENCE: 4

Met Arg Arg Glu Lys Leu Lys Leu Leu Ile Val Asp Asp Glu Pro Asp
1               5                   10                  15

Asn Leu Asp Leu Leu Tyr Arg Thr Phe Arg Arg Asp Phe Asp Val Ile
            20                  25                  30

Arg Ala Glu Ser Ala Ile Glu Ala Leu Lys Val Leu Asp Glu Gln Gly
        35                  40                  45

Glu Val Ala Ile Ile Ser Asp Gln Arg Met Pro Glu Met Leu Gly
    50                  55                  60

Thr Glu Phe Leu Ser Arg Thr Val Asp Arg Phe Pro Asp Thr Ile Arg
65                  70                  75                  80

Ile Val Leu Thr Gly Tyr Thr Asp Val Glu Asp Leu Val Asp Ala Ile
                85                  90                  95

Asn Ser Gly Lys Val Phe Lys Tyr Ile Thr Lys Pro Trp Lys Ser Gln
            100                 105                 110

Gln Leu Gln Val Val Val Glu Gln Ala Ala Glu Thr Tyr Gln Val Leu
        115                 120                 125

Lys Gln Arg Thr Ala Asp Leu Arg Arg Ala Leu Arg Arg Glu Ser Ser
    130                 135                 140

Leu Asn Ala Ile Thr Thr Ala Ile Arg Glu Ser Leu Asp Tyr Gln Asn
145                 150                 155                 160

Met Leu His Thr Ile Val Glu Thr Ile Gly Leu Thr Phe Glu Ala Ser
                165                 170                 175

Cys Cys Met Leu His Pro Val Glu Gly Glu Arg Leu Lys Ser Asn Ser
            180                 185                 190
```

```
Ala Met Tyr Cys Ala Val Asn Val Pro Phe Lys Ser Cys Glu Asp Asp
        195                 200                 205

Arg Thr Ser Asp Leu Val Gln Ile Val Leu His Asp Ser Thr Ala Arg
    210                 215                 220

Met Lys Ser Gln Asn Pro Pro His Phe Val Leu Pro Leu Arg Tyr Gln
225                 230                 235                 240

Lys Asp Leu Leu Ala Ile Leu Ser Leu His Arg Glu Ser Asp Gln Pro
                245                 250                 255

Phe Trp Ser Thr Glu Asp Leu Glu Leu Ile Glu Val Val Thr Glu Gln
            260                 265                 270

Ala Ala Leu Ala Ile Ser Gln Ala Arg Leu Tyr Arg Arg Thr Gln Glu
        275                 280                 285

Gln Ala Glu Gln Ile Arg Ala Glu Leu Glu Val Ala Arg Gln Ile Gln
    290                 295                 300

Thr Asn Leu Leu Arg Gln Thr Leu Pro Arg Leu Asp Asn Leu Lys Val
305                 310                 315                 320

Gln Ala Cys Cys His Pro Ala Arg Glu Val Gly Gly Asp Phe Phe Glu
                325                 330                 335

Val Tyr Gln His Pro Gln Gly Asp Leu Trp Leu Ala Val Gly Asp Val
            340                 345                 350

Ser Gly Lys Gly Val Pro Ala Ala Leu Phe Met Ala Ser Ala Ile Ser
        355                 360                 365

Val Leu Arg Arg Glu Leu Ser Gln Glu Val Ser Pro Glu Pro Asp Glu
    370                 375                 380

Val Met Arg Asn Leu Asn Ser Ile Leu Ser Gln Asp Leu Met Gly Thr
385                 390                 395                 400

Asn Cys Phe Ile Thr Met Val Leu Ala Arg Tyr Thr Arg Ser Ser Gly
                405                 410                 415

Gln Leu Val Tyr Ala Asn Ala Gly His Ile Tyr Pro Leu Val Trp Ser
            420                 425                 430

Lys His Thr Ile Ala Gln Ala Ile Glu Pro Thr Tyr Leu Lys Val Arg
        435                 440                 445

Gly Ile Pro Leu Gly Ile Leu Pro Lys Trp Asn Ala Ile Ala Gly Lys
    450                 455                 460

Arg Leu Leu Gln Asp Gly Glu Ile Leu Leu Thr Ser Asp Gly Ile
465                 470                 475                 480

Thr Glu Ala Thr Val Arg Pro Glu Gly Glu Val Asn Leu Ala Ser Asp
                485                 490                 495

Pro Ala Arg Ala Met Leu Arg Gln Thr Gly Leu Trp Lys Leu Leu Gln
            500                 505                 510

Gln Ala Gly Glu Ser Leu Asp Leu Lys Gln Leu Leu Ala Gln Ile Gln
        515                 520                 525

Ala His Asn Ala Ile Gln Glu Asp Asp Gln Thr Ile Leu Ser Leu Glu
    530                 535                 540

Val Leu
545

<210> SEQ ID NO 5
<211> LENGTH: 1173
<212> TYPE: DNA
<213> ORGANISM: Leptolyngbya sp.

<400> SEQUENCE: 5
atgcctaccc cacgcaactc gacccgggaa cgcctcatcc aagccgcctt agagttattc      60
```

```
acggcgaacg gtattaccga cactactacc aaacaaatcg ctgaattagc cgacgtaaat      120
gaagtgactc tgtttcggca ttttggcaac aaacatgggc tgttactggc tgcgatcgaa      180
gaagcggcgg tttttactca actcggtcaa cgctggtag aacgggcaga tcaagctgat       240
tatatcgacc aagcgctgaa agaatatgcg atcgcctgtt tggaagcgct ggagcaggtt      300
ccagaaatgg tgcgatcagt ggtgggtgaa gcgggacaat acccgaccga aaatcgagaa      360
gcgttagggc ggggtctgac ccaagccaat cgctatgtgg cggaatattt cgatcgcgtg      420
attcatcgcc gccaaatgca gcctaattta tcgtctgaaa gtcttgcaag tcttctaaat      480
ggcatgctgt taggctatgc agtgatcgaa ttcaccagcg aatttcatga gctttggcaa      540
agccgcgacg attttctaac gaatttggtg acttattttt tgcaaggcgc gattcagccg      600
acccaggctg agtctttaga ggttcgagat ttgccagcag acacggttca tcaaatttta      660
cagcgggcaa aaaagcaagg cgttcaggat tatgcgatcg cttatgtttt attcggtgca      720
ggcttaagtg cgcgagaact cactgaattg acgcgatcgg attaccacgt caagcagatt      780
caagtttcga cgcgccaagt tccgttaaat caatggatat tagaaaaacg ctacggttct      840
catacaaaaa atccgctgac tcaatggctc aaaactcgta aagatgcgct tcctgccatg      900
tttctagcga gtgagaatca gcccattacc gaagctgata ttctgcaacg ttggactgat      960
tggactgagg gaattccaaa tgaaccaggg atcgaacaag cctatcaaac ttggtgtgtt     1020
gatctcttaa tgcgaggcat tacgatcgca gatctgaaga ttttgacgca acaaaccgaa     1080
gcgcaacttc agccatttgt cgatcgagca cgagagaaat tagcaattga caagcaatc      1140 agacttgatc agccacctcg gtcaattgct aaa                                  1173

<210> SEQ ID NO 6
<211> LENGTH: 391
<212> TYPE: PRT
<213> ORGANISM: Leptolyngbya sp.

<400> SEQUENCE: 6

Met Pro Thr Pro Arg Asn Ser Thr Arg Glu Arg Leu Ile Gln Ala Ala
1               5                   10                  15

Leu Glu Leu Phe Thr Ala Asn Gly Ile Thr Asp Thr Thr Lys Gln
            20                  25                  30

Ile Ala Glu Leu Ala Asp Val Asn Glu Val Thr Leu Phe Arg His Phe
        35                  40                  45

Gly Asn Lys His Gly Leu Leu Leu Ala Ala Ile Glu Glu Ala Ala Val
    50                  55                  60

Phe Thr Gln Leu Gly Gln Thr Leu Val Glu Arg Ala Asp Gln Ala Asp
65                  70                  75                  80

Tyr Ile Asp Gln Ala Leu Lys Glu Tyr Ala Ile Ala Cys Leu Glu Ala
                85                  90                  95

Leu Glu Gln Val Pro Glu Met Val Arg Ser Val Gly Glu Ala Gly
            100                 105                 110

Gln Tyr Pro Thr Glu Asn Arg Glu Ala Leu Gly Arg Gly Leu Thr Gln
        115                 120                 125

Ala Asn Arg Tyr Val Ala Glu Tyr Phe Asp Arg Val Ile His Arg Arg
    130                 135                 140

Gln Met Gln Pro Asn Leu Ser Ser Glu Ser Leu Ala Ser Leu Leu Asn
145                 150                 155                 160

Gly Met Leu Leu Gly Tyr Ala Val Ile Glu Phe Thr Ser Glu Phe His
                165                 170                 175
```

```
Glu Leu Trp Gln Ser Arg Asp Asp Phe Leu Thr Asn Leu Val Thr Leu
            180                 185                 190
Phe Leu Gln Gly Ala Ile Gln Pro Thr Gln Ala Glu Ser Leu Glu Val
        195                 200                 205
Arg Asp Leu Pro Ala Asp Thr Val His Gln Ile Leu Gln Arg Ala Lys
    210                 215                 220
Lys Gln Gly Val Gln Asp Tyr Ala Ile Ala Tyr Val Leu Phe Gly Ala
225                 230                 235                 240
Gly Leu Ser Ala Arg Glu Leu Thr Glu Leu Thr Arg Ser Asp Tyr His
                245                 250                 255
Val Lys Gln Ile Gln Val Ser Thr Arg Gln Val Pro Leu Asn Gln Trp
            260                 265                 270
Ile Leu Glu Lys Arg Tyr Gly Ser His Thr Lys Asn Pro Leu Thr Gln
        275                 280                 285
Trp Leu Lys Thr Arg Lys Asp Ala Leu Pro Ala Met Phe Leu Ala Ser
    290                 295                 300
Glu Asn Gln Pro Ile Thr Glu Ala Asp Ile Leu Gln Arg Trp Thr Asp
305                 310                 315                 320
Trp Thr Glu Gly Ile Pro Asn Glu Pro Gly Ile Glu Gln Ala Tyr Gln
                325                 330                 335
Thr Trp Cys Val Asp Leu Leu Met Arg Gly Ile Thr Ile Ala Asp Leu
            340                 345                 350
Lys Ile Leu Thr Gln Gln Thr Glu Ala Gln Leu Gln Pro Phe Val Asp
        355                 360                 365
Arg Ala Arg Glu Lys Leu Ala Ile Glu Gln Ala Ile Arg Leu Asp Gln
    370                 375                 380
Pro Pro Arg Ser Ile Ala Lys
385                 390

<210> SEQ ID NO 7
<211> LENGTH: 2088
<212> TYPE: DNA
<213> ORGANISM: Thermosynechococcus sp.

<400> SEQUENCE: 7
atggttagcc gtcaagggta tagattcgac tttccaacag gtgcagatcc ttacgagtta     60
atacggacaa tttgtgcgcg gctacccta ttaatgattt tttacgggaa cgaaggccaa    120
atcctttcca taaatcaaga agtgacgacc catttgggat gggatgtcgg agatttactc    180
tcacgagatt ttttgagcca gtgtttccct gaccccgaaa cccagcgcca attccgctac    240
tggatgctcc atccccccac gggttggcaa gagattccct gtcattctgc ctatggccaa    300
atgttagaga tgatctgggc gtttgtgcgt tttcccaatg gtgaaggctt ggtctgtggc    360
cacaacgtta ccgatgcaaa gctcacccaa tcggcactgc tagaaaccag cgatcgctat    420
gcattgctgg tcgggggcat gaatgatggc gtgtgggact ggaaccttgt gaccgatgaa    480
acgttctact cctcgcgctg gaaaacgcta cttgggtacc aagaccacga aattgggaat    540
cacattgatg actggctacg gcgcatccac cctcaggatg cagagcgggt gaagctcaat    600
ttaaccttac atgtgcgcgg tcaaaccca cacttccacc aagagtttcg cattcaacat    660
cgcaacggct cctatcgctg ggcgttagca cgggggttag tcttgcggga tgcctacggc    720
aaagcctatc gcgtggctgg ctccctaacg gatttaaccg aacaccgttt agcagaggcg    780
cagttacttc acgatgccct ccacgattct ttaacggggt tagccaaccg gacgttgctt    840
```

-continued

```
tttgatcgga ttgaacaggc cgcgcggcat ggtcgtcgcc gccccgacta taaatttgcc      900
attttgttta ttgatattga tcgctttaag gtcattaacg acagtttggg acacagttgt      960
ggggatgcca ttttaattga actggggcag cgccttcagc gcatcgtgcg tcctgatgat     1020
acagttgccc gcattggtgg cgatgaattt gttatcttgc tggatgatat tactggcaat     1080
agcgatgcct gggggtgtgt cgatcgcatt cactatgaat acaaacccc ctttacccctc     1140
aaggatcagc agattatgct gcgggtcagt attggcgttg ccacccgtgc gccccacatc     1200
gaaaaagcag aaaattatct gcgcaatgcg gacattgcca tgtatcgtgc caagctggca     1260
gggggaagcc gctaccaaat ttttagtgaa gaaatgcact taatggcgcg cgatcgccta     1320
tcgttggaag ttggactgcg gcaagccatt gagcgcgatg aatttacgct ccactatcag     1380
cctatttatc gcctcagcga caaccgtctt tacggctttg aagccttaat tcgctggcac     1440
catcccaccg aaggcttact caaccccgat cgtttcatcg ccttagctga gaaacgggc     1500
ttaattttac cgattgggga ttgggtattg tggcgcgcct gtcgggatct gcaacgctgg     1560
caagagcagg atccccagca ccctctgtgt gtcaatgtga atctttccaa tcgccaactc     1620
atgcatcctg cccttgtgga gcaggtgtta gcggcgcttg agcaaaccca agtgcccct     1680
gagtctctgc accttgagat tacagaaagc gtgggtattg ataaacctga gcaggtgcgg     1740
gacattttgc tagccctcaa ggctcatggc ctcaaactga gtatggatga ttttggcacg     1800
gggtactcgt cccttagcta tctcacgaac ttacccattg acattctcaa ggtggatcgc     1860
tcgtttgtga agttaattac cgagaccaac caacaacact cggtcattga tgcgattctg     1920
agtttggcaa aggggctaga gctagaggtg gttgccgaag gggttgagca cgcctatcag     1980
gtcactcgct tgcgggaatt ggggtgtggc tatgcccaag gctattactt ttcacggcct     2040
ttgacgcgag agcaggtgga tcagttgctg gttgagcgct atcggttt                   2088
```

<210> SEQ ID NO 8
<211> LENGTH: 696
<212> TYPE: PRT
<213> ORGANISM: Thermosynechococcus sp.

<400> SEQUENCE: 8

```
Met Val Ser Arg Gln Gly Tyr Arg Phe Asp Phe Pro Thr Gly Ala Asp
1               5                   10                  15

Pro Tyr Glu Leu Ile Arg Thr Ile Cys Ala Arg Leu Pro Leu Leu Met
            20                  25                  30

Ile Phe Tyr Gly Asn Glu Gly Gln Ile Leu Ser Ile Asn Gln Glu Val
        35                  40                  45

Thr Thr His Leu Gly Trp Asp Val Gly Asp Leu Leu Ser Arg Asp Phe
    50                  55                  60

Leu Ser Gln Cys Phe Pro Asp Pro Glu Thr Gln Arg Gln Phe Arg Tyr
65                  70                  75                  80

Trp Met Leu His Pro Pro Thr Gly Trp Gln Glu Ile Pro Cys His Ser
                85                  90                  95

Ala Tyr Gly Gln Met Leu Glu Met Ile Trp Ala Phe Val Arg Phe Pro
            100                 105                 110

Asn Gly Glu Gly Leu Val Cys Gly His Asn Val Thr Asp Ala Lys Leu
        115                 120                 125

Thr Gln Ser Ala Leu Leu Glu Thr Ser Asp Arg Tyr Ala Leu Leu Ala
    130                 135                 140

Arg Gly Met Asn Asp Gly Val Trp Asp Trp Asn Leu Val Thr Asp Glu
145                 150                 155                 160
```

```
Thr Phe Tyr Ser Ser Arg Trp Lys Thr Leu Leu Gly Tyr Gln Asp His
                165                 170                 175

Glu Ile Gly Asn His Ile Asp Asp Trp Leu Arg Arg Ile His Pro Gln
            180                 185                 190

Asp Ala Glu Arg Val Lys Leu Asn Leu Thr Leu His Val Arg Gly Gln
        195                 200                 205

Thr Pro His Phe His Gln Glu Phe Arg Ile Gln His Arg Asn Gly Ser
    210                 215                 220

Tyr Arg Trp Ala Leu Ala Arg Gly Leu Val Leu Arg Asp Ala Tyr Gly
225                 230                 235                 240

Lys Ala Tyr Arg Val Ala Gly Ser Leu Thr Asp Leu Thr Glu His Arg
                245                 250                 255

Leu Ala Glu Ala Gln Leu Leu His Asp Ala Leu His Asp Ser Leu Thr
            260                 265                 270

Gly Leu Ala Asn Arg Thr Leu Leu Phe Asp Arg Ile Glu Gln Ala Ala
        275                 280                 285

Arg His Gly Arg Arg Pro Asp Tyr Lys Phe Ala Ile Leu Phe Ile
    290                 295                 300

Asp Ile Asp Arg Phe Lys Val Ile Asn Asp Ser Leu Gly His Ser Cys
305                 310                 315                 320

Gly Asp Ala Ile Leu Ile Glu Leu Gly Gln Arg Leu Gln Arg Ile Val
                325                 330                 335

Arg Pro Asp Asp Thr Val Ala Arg Ile Gly Gly Asp Glu Phe Val Ile
            340                 345                 350

Leu Leu Asp Asp Ile Thr Gly Asn Ser Asp Ala Leu Gly Val Cys Asp
        355                 360                 365

Arg Ile His Tyr Glu Leu Gln Thr Pro Phe Thr Leu Lys Asp Gln Gln
    370                 375                 380

Ile Met Leu Arg Val Ser Ile Gly Val Ala Thr Arg Ala Pro His Ile
385                 390                 395                 400

Glu Lys Ala Glu Asn Tyr Leu Arg Asn Ala Asp Ile Ala Met Tyr Arg
                405                 410                 415

Ala Lys Leu Ala Gly Gly Ser Arg Tyr Gln Ile Phe Ser Glu Glu Met
            420                 425                 430

His Leu Met Ala Arg Asp Arg Leu Ser Leu Glu Val Gly Leu Arg Gln
        435                 440                 445

Ala Ile Glu Arg Asp Glu Phe Thr Leu His Tyr Gln Pro Ile Tyr Arg
    450                 455                 460

Leu Ser Asp Asn Arg Leu Tyr Gly Phe Glu Ala Leu Ile Arg Trp His
465                 470                 475                 480

His Pro Thr Glu Gly Leu Leu Asn Pro Asp Arg Phe Ile Ala Leu Ala
                485                 490                 495

Glu Glu Thr Gly Leu Ile Leu Pro Ile Gly Asp Trp Val Leu Trp Arg
            500                 505                 510

Ala Cys Arg Asp Leu Gln Arg Trp Gln Glu Gln Asp Pro Gln His Pro
        515                 520                 525

Leu Cys Val Asn Val Asn Leu Ser Asn Arg Gln Leu Met His Pro Ala
    530                 535                 540

Leu Val Glu Gln Val Leu Ala Ala Leu Glu Gln Thr Gln Val Pro Pro
545                 550                 555                 560

Glu Ser Leu His Leu Glu Ile Thr Glu Ser Val Gly Ile Asp Lys Pro
                565                 570                 575
```

```
Glu Gln Val Arg Asp Ile Leu Leu Ala Leu Lys Ala His Gly Leu Lys
            580                 585                 590

Leu Ser Met Asp Asp Phe Gly Thr Gly Tyr Ser Ser Leu Ser Tyr Leu
        595                 600                 605

Thr Asn Leu Pro Ile Asp Ile Leu Lys Val Asp Arg Ser Phe Val Lys
    610                 615                 620

Leu Ile Thr Glu Thr Asn Gln Gln His Ser Val Ile Asp Ala Ile Leu
625                 630                 635                 640

Ser Leu Ala Lys Gly Leu Glu Leu Glu Val Ala Glu Gly Val Glu
                645                 650                 655

His Ala Tyr Gln Val Thr Arg Leu Arg Glu Leu Gly Cys Gly Tyr Ala
            660                 665                 670

Gln Gly Tyr Tyr Phe Ser Arg Pro Leu Thr Arg Glu Gln Val Asp Gln
                675                 680                 685

Leu Leu Val Glu Arg Tyr Arg Phe
        690                 695

<210> SEQ ID NO 9
<211> LENGTH: 315
<212> TYPE: DNA
<213> ORGANISM: Unknown
<220> FEATURE:
<223> OTHER INFORMATION: Bacterial DNA-binding protein derived from
      metagenome of environmental isolates collected at various
      California locations

<400> SEQUENCE: 9
gtggcaggag agttcacgat ggcaatcgcc gcgacgctga ccagggccga tcttgccgat      60
gcattgcacc gcgatgttgg cttgtcccgc gcggatgctt cccgcctcgt cgaacaattg     120
ctcggccata tgtgcgacgc gcttgcccgt ggcgagaatg tgaagatttc agggttcggc     180
agctttgtcc tgcgtgacaa gggtgagcgg atcggccgca accccaagac cggggtcgaa     240
gtgccgatcg caccccgccg cgtcctcacc ttccgtgcca gcagatgct gcgcgaccgg      300 atcgtgagcg ggggg                                                      315

<210> SEQ ID NO 10
<211> LENGTH: 105
<212> TYPE: PRT
<213> ORGANISM: Unknown
<220> FEATURE:
<223> OTHER INFORMATION: Bacterial DNA-binding protein derived from
      metagenome of environmental isolates collected at various
      California locations

<400> SEQUENCE: 10

Met Ala Gly Glu Phe Thr Met Ala Ile Ala Ala Thr Leu Thr Arg Ala
1               5                   10                  15

Asp Leu Ala Asp Ala Leu His Arg Asp Val Gly Leu Ser Arg Ala Asp
            20                  25                  30

Ala Ser Arg Leu Val Glu Gln Leu Leu Gly His Met Cys Asp Ala Leu
        35                  40                  45

Ala Arg Gly Glu Asn Val Lys Ile Ser Gly Phe Gly Ser Phe Val Leu
    50                  55                  60

Arg Asp Lys Gly Glu Arg Ile Gly Arg Asn Pro Lys Thr Gly Val Glu
65                  70                  75                  80

Val Pro Ile Ala Pro Arg Arg Val Leu Thr Phe Arg Ala Ser Gln Met
                85                  90                  95

Leu Arg Asp Arg Ile Val Ser Gly Gly
            100                 105
```

<210> SEQ ID NO 11
<211> LENGTH: 327
<212> TYPE: DNA
<213> ORGANISM: Unknown
<220> FEATURE:
<223> OTHER INFORMATION: MerR family regulatory protein derived from
metagenome of environmental isolates collected at various
California locations

<400> SEQUENCE: 11

```
atgacggtcg gtccggagaa gggccccgag gccttccgga ccatcggtga gcttgcgcag    60
gaaatcgggc ggccccagca tatcttgcgt tattgggaaa ctcgcttccc gcagttgcga   120
ccgctgcagc gcgcgggtgg ccgccgctat tatcgtcctg ccgatgtcgc gctggtccgc   180
cgcatcgatg cgctgctcac ccatgagggc tatacgatcc gcggcgttca gcgcctgctg   240
gcggccgagg gcgcgtcgcg ccgtgaccgc gcggcgccat tgcgggcggt gcgcgccgag   300
ctgcaggcgg cgctggacga ggattgc                                       327
```

<210> SEQ ID NO 12
<211> LENGTH: 109
<212> TYPE: PRT
<213> ORGANISM: Unknown
<220> FEATURE:
<223> OTHER INFORMATION: MerR family regulatory protein derived from
metagenome of environmental isolates collected at various
California locations

<400> SEQUENCE: 12

```
Met Thr Val Gly Pro Glu Lys Gly Pro Glu Ala Phe Arg Thr Ile Gly
 1               5                  10                  15

Glu Leu Ala Gln Glu Ile Gly Arg Pro Gln His Ile Leu Arg Tyr Trp
            20                  25                  30

Glu Thr Arg Phe Pro Gln Leu Arg Pro Leu Gln Arg Ala Gly Gly Arg
        35                  40                  45

Arg Tyr Tyr Arg Pro Ala Asp Val Ala Leu Val Arg Arg Ile Asp Ala
    50                  55                  60

Leu Leu Thr His Glu Gly Tyr Thr Ile Arg Gly Val Gln Arg Leu Leu
65                  70                  75                  80

Ala Ala Glu Gly Ala Ser Arg Arg Asp Arg Ala Ala Pro Leu Arg Ala
                85                  90                  95

Val Arg Ala Glu Leu Gln Ala Ala Leu Asp Glu Asp Cys
           100                 105
```

<210> SEQ ID NO 13
<211> LENGTH: 732
<212> TYPE: DNA
<213> ORGANISM: Synechococcus sp.

<400> SEQUENCE: 13

```
ttggaaaatc gcaaggaaaa aatcctcgtt gttgatgatg aagcgagtat ccggcgcatt    60
ctcgaaaccc ggttggcgat gattggctac gaagtcgtga cggcagccga cggcgaagag   120
gcgctcacca ctttccgcaa cagcacgccc gatctggtgg tgctcgatgt catgatgccc   180
aagctggatg gctacggcgt tgccaagag ctgcgcaaag agtcggatgt tcccatcatc   240
atgctgacgg cgctgggtga tgtggccgat cgcatcaccg tcttgagct gggcgccgat   300 gattatgtcg tcaaacccctt ctcgcccaag gaactggaag cccggattcg ctcagtcctg   360
```

```
cgtcgggttg aaaaaagcgg tgccaatggc attcccagct cgggcgtcat tcaaatcaac      420
agcattcgca tcgacaccaa taagcgccaa gtctacaaag gcgatgagcg catccgtctg      480
acaggcatgg aatttagcct gctcgaactg ctggtcagcc gctctggtga acccttcagc      540
cgcgccgaaa tcctacaaga agtctggggc tacacgcccg agcgccacgt ggatacccgc      600
gtggtcgatg tccatatttc gcggttgcgc gccaagctgg aagacgatcc gggtaatccc      660
gagttgatcc tgacggctcg cggcacgggc tatttgttcc agcgaattgt cgagcccggc      720
gaagaaggcc gt                                                         732
```

<210> SEQ ID NO 14
<211> LENGTH: 244
<212> TYPE: PRT
<213> ORGANISM: Synechococcus sp.

<400> SEQUENCE: 14

```
Met Glu Asn Arg Lys Glu Lys Ile Leu Val Val Asp Asp Glu Ala Ser
1               5                   10                  15

Ile Arg Arg Ile Leu Glu Thr Arg Leu Ala Met Ile Gly Tyr Glu Val
            20                  25                  30

Val Thr Ala Ala Asp Gly Glu Glu Ala Leu Thr Thr Phe Arg Asn Ser
        35                  40                  45

Thr Pro Asp Leu Val Val Leu Asp Val Met Met Pro Lys Leu Asp Gly
    50                  55                  60

Tyr Gly Val Cys Gln Glu Leu Arg Lys Glu Ser Asp Val Pro Ile Ile
65                  70                  75                  80

Met Leu Thr Ala Leu Gly Asp Val Ala Asp Arg Ile Thr Gly Leu Glu
                85                  90                  95

Leu Gly Ala Asp Asp Tyr Val Val Lys Pro Phe Ser Pro Lys Glu Leu
            100                 105                 110

Glu Ala Arg Ile Arg Ser Val Leu Arg Arg Val Glu Lys Ser Gly Ala
        115                 120                 125

Asn Gly Ile Pro Ser Ser Gly Val Ile Gln Ile Asn Ser Ile Arg Ile
    130                 135                 140

Asp Thr Asn Lys Arg Gln Val Tyr Lys Gly Asp Glu Arg Ile Arg Leu
145                 150                 155                 160

Thr Gly Met Glu Phe Ser Leu Leu Glu Leu Leu Val Ser Arg Ser Gly
                165                 170                 175

Glu Pro Phe Ser Arg Ala Glu Ile Leu Gln Glu Val Trp Gly Tyr Thr
            180                 185                 190

Pro Glu Arg His Val Asp Thr Arg Val Val Asp Val His Ile Ser Arg
        195                 200                 205

Leu Arg Ala Lys Leu Glu Asp Asp Pro Gly Asn Pro Glu Leu Ile Leu
    210                 215                 220

Thr Ala Arg Gly Thr Gly Tyr Leu Phe Gln Arg Ile Val Glu Pro Gly
225                 230                 235                 240

Glu Glu Gly Arg
```

<210> SEQ ID NO 15
<211> LENGTH: 732
<212> TYPE: DNA
<213> ORGANISM: Synechococcus sp.

<400> SEQUENCE: 15

```
ttggaaaatc gcaaggaaaa aatcctcgtt gttgacgatg aagcgagcat ccggcggatt       60
```

-continued

```
cttgaaactc ggttggccat gattggctac gaagtcgtca ccgcagccga tggcgaagaa    120
gccttaacca cattccgcaa tgctacgccg gatctcgtgg tgctcgatgt catgatgccc    180
aagctcgacg gctatggcgt ttgccaagaa ctacgcaaag agtcagatgt gccaatcatc    240
atgctgacgg cgttgggcga cgtcgccgat cgcatcaccg gccttgaact tggcgctgat    300
gactacgtcg tcaaaccttt ctctcccaag gaactagaag cgcggatccg ctcagtcctc    360
agacgggtcg aaaaaagcgg tgccaatggc atccccagtt caggcgtcat ccagatcaac    420
agcatccgca tcgacaccaa taagcgtcag gtttacaaag gcgatgagcg gattcgcctg    480
acgggcatgg agttcagtct gctagaactg ctggtcagtc gctccggtga gccttttagt    540
cgcgccgaaa tcctgcaaga ggtctgggc tacacgcccg agcgccacgt cgatacccgc     600
gtcgtcgatg tccatatctc gcggctgcgc gccaagctcg aagatgatcc gggcaaccca    660
gagctgattc tgacggcacg gggaactggc tacctcttcc agcgcatcgt tgagccaggt    720
gaagaaggcc gc                                                         732
```

<210> SEQ ID NO 16
<211> LENGTH: 244
<212> TYPE: PRT
<213> ORGANISM: Synechococcus sp.

<400> SEQUENCE: 16

```
Met Glu Asn Arg Lys Glu Lys Ile Leu Val Val Asp Asp Glu Ala Ser
  1               5                  10                  15

Ile Arg Arg Ile Leu Glu Thr Arg Leu Ala Met Ile Gly Tyr Glu Val
             20                  25                  30

Val Thr Ala Ala Asp Gly Glu Glu Ala Leu Thr Thr Phe Arg Asn Ala
         35                  40                  45

Thr Pro Asp Leu Val Val Leu Asp Val Met Met Pro Lys Leu Asp Gly
     50                  55                  60

Tyr Gly Val Cys Gln Glu Leu Arg Lys Glu Ser Asp Val Pro Ile Ile
 65                  70                  75                  80

Met Leu Thr Ala Leu Gly Asp Val Ala Asp Arg Ile Thr Gly Leu Glu
                 85                  90                  95

Leu Gly Ala Asp Asp Tyr Val Val Lys Pro Phe Ser Pro Lys Glu Leu
            100                 105                 110

Glu Ala Arg Ile Arg Ser Val Leu Arg Arg Val Glu Lys Ser Gly Ala
        115                 120                 125

Asn Gly Ile Pro Ser Ser Gly Val Ile Gln Ile Asn Ser Ile Arg Ile
    130                 135                 140

Asp Thr Asn Lys Arg Gln Val Tyr Lys Gly Asp Glu Arg Ile Arg Leu
145                 150                 155                 160

Thr Gly Met Glu Phe Ser Leu Leu Glu Leu Leu Val Ser Arg Ser Gly
                165                 170                 175

Glu Pro Phe Ser Arg Ala Glu Ile Leu Gln Glu Val Trp Gly Tyr Thr
            180                 185                 190

Pro Glu Arg His Val Asp Thr Arg Val Val Asp Val His Ile Ser Arg
        195                 200                 205

Leu Arg Ala Lys Leu Glu Asp Asp Pro Gly Asn Pro Glu Leu Ile Leu
    210                 215                 220

Thr Ala Arg Gly Thr Gly Tyr Leu Phe Gln Arg Ile Val Glu Pro Gly
225                 230                 235                 240

Glu Glu Gly Arg
```

<210> SEQ ID NO 17
<211> LENGTH: 705
<212> TYPE: DNA
<213> ORGANISM: Unknown
<220> FEATURE:
<223> OTHER INFORMATION: Cyanobacterium

<400> SEQUENCE: 17

```
atgtctcgaa tactcgtaat tgacgatgat ccagcgatca ctgaattagt ctccataaac    60
ttagaaatgg caggttatac aaccgcccaa gctgaagatg cataaaagg acaagctctc   120
gccttacaaa tgcaaccaga tttaattatg ttagacctca tgttaccaaa agtggacggt   180
ttaacagtct gtcaaagatt aagacgagat gagagaacgg caaatatacc tgttttaatg   240
ttaactgctt tagggcaaac tcaagataaa gtcgatggtt ttaacgctgg tgcagatgat   300
taccttacga aaccttttga agtagaagaa atgttggcac gggtgaaagc cttactgaga   360
agaagtgaaa gaacctctcc tgtcgctaaa cactcagaaa ttcttagtta tggtcccttta  420
accttagttc cagaaagatt tgaggctatt tggttcgaga agacaattaa actaactcat   480
ttagaatttg aactattaca ctgttttacta caacgtcatg gcaaacagt tccccccagt   540
gatattctta aagaggtatg gggttacgat ccagatgat atatagagac tattagagta    600
cacgttcgcc atttacgtac taaactagaa cctgatcctc gtaaacctcg ctatattaaa    660
actgtttatg gtgctggtta ttgcttagaa ttgaatacgg ataac                    705
```

<210> SEQ ID NO 18
<211> LENGTH: 235
<212> TYPE: PRT
<213> ORGANISM: Unknown
<220> FEATURE:
<223> OTHER INFORMATION: Cyanobacterium

<400> SEQUENCE: 18

```
Met Ser Arg Ile Leu Val Ile Asp Asp Pro Ala Ile Thr Glu Leu
1               5                   10                  15

Val Ser Ile Asn Leu Glu Met Ala Gly Tyr Thr Thr Ala Gln Ala Glu
            20                  25                  30

Asp Gly Ile Lys Gly Gln Ala Leu Ala Leu Gln Met Gln Pro Asp Leu
        35                  40                  45

Ile Met Leu Asp Leu Met Leu Pro Lys Val Asp Gly Leu Thr Val Cys
    50                  55                  60

Gln Arg Leu Arg Arg Asp Glu Arg Thr Ala Asn Ile Pro Val Leu Met
65                  70                  75                  80

Leu Thr Ala Leu Gly Gln Thr Gln Asp Lys Val Asp Gly Phe Asn Ala
                85                  90                  95

Gly Ala Asp Asp Tyr Leu Thr Lys Pro Phe Glu Val Glu Glu Met Leu
            100                 105                 110

Ala Arg Val Lys Ala Leu Leu Arg Arg Ser Glu Arg Thr Ser Pro Val
        115                 120                 125

Ala Lys His Ser Glu Ile Leu Ser Tyr Gly Pro Leu Thr Leu Val Pro
    130                 135                 140

Glu Arg Phe Glu Ala Ile Trp Phe Glu Lys Thr Ile Lys Leu Thr His
145                 150                 155                 160

Leu Glu Phe Glu Leu Leu His Cys Leu Leu Gln Arg His Gly Gln Thr
                165                 170                 175

Val Pro Pro Ser Asp Ile Leu Lys Glu Val Trp Gly Tyr Asp Pro Asp
            180                 185                 190
```

Asp Asp Ile Glu Thr Ile Arg Val His Val Arg His Leu Arg Thr Lys
        195                 200                 205

Leu Glu Pro Asp Pro Arg Lys Pro Arg Tyr Ile Lys Thr Val Tyr Gly
        210                 215                 220

Ala Gly Tyr Cys Leu Glu Leu Asn Thr Asp Asn
225             230                 235

<210> SEQ ID NO 19
<211> LENGTH: 513
<212> TYPE: DNA
<213> ORGANISM: Synechocystis PCC 6803

<400> SEQUENCE: 19

```
atgcctgggg ccggttcacc gttagacttg ggttggaact ttagcgttga gcatatgact    60
atggcatccc ccgcaccaga gttggcccct accaccatgg ctgaaatggc ccccgttagt   120
caccacgacg ttgtcgaaac ggttatttcc ggcatggccc aggaaaatag cgcctttgtg   180
caagataacg accagggtag catctggaaa tttgcctatg gcagtgtgga agtgctagta   240
cagctcactg gagaagggga aaatgatctg tttcgggtgt gggctgaggt gatgccctta   300
ccaacagatc cgggccaatt attggcggaa gtgatggaat aaactggtc agatacgttt   360
gaagcctgtt tgctgtgcg ggaaaatcat ttagtggccc tccatcagcg cactgtggcg   420
gatctttccc ccagtgaaat tcccgggcc attaccctgg tggcaacatt ggctgatgac   480
catgacgatc gcctgaagga aaaatacggc gct                               513
```

<210> SEQ ID NO 20
<211> LENGTH: 171
<212> TYPE: PRT
<213> ORGANISM: Synechocystis PCC 6803

<400> SEQUENCE: 20

Met Pro Gly Ala Gly Ser Pro Leu Asp Leu Gly Trp Asn Phe Ser Val
1               5                   10                  15

Glu His Met Thr Met Ala Ser Pro Ala Pro Glu Leu Ala Pro Thr Thr
            20                  25                  30

Met Ala Glu Met Ala Pro Val Ser His His Asp Val Glu Thr Val
        35                  40                  45

Ile Ser Gly Met Ala Gln Glu Asn Ser Ala Phe Val Gln Asp Asn Asp
    50                  55                  60

Gln Gly Ser Ile Trp Lys Phe Ala Tyr Gly Ser Val Glu Val Leu Val
65                  70                  75                  80

Gln Leu Thr Gly Glu Gly Glu Asn Asp Leu Phe Arg Val Trp Ala Glu
                85                  90                  95

Val Met Pro Leu Pro Thr Asp Pro Gly Gln Leu Leu Ala Glu Val Met
            100                 105                 110

Glu Leu Asn Trp Ser Asp Thr Phe Glu Ala Cys Phe Ala Val Arg Glu
        115                 120                 125

Asn His Leu Val Ala Leu His Gln Arg Thr Val Ala Asp Leu Ser Pro
    130                 135                 140

Ser Glu Ile Ser Arg Ala Ile Thr Leu Val Ala Thr Leu Ala Asp Asp
145                 150                 155                 160

His Asp Asp Arg Leu Lys Glu Lys Tyr Gly Ala
                165                 170

<210> SEQ ID NO 21

<211> LENGTH: 609
<212> TYPE: DNA
<213> ORGANISM: Synechocystis PCC 6803

<400> SEQUENCE: 21

```
atggtagcag aatttccgga ccgtcatcct gttgtgttag tccatggcat ttacgacacc      60
agggctaaat ttgccaccat ggtggatttt ttgaccaagg gcggctggtc agttcattgt     120
ttagacctag tgcccaacga tggcagtact tccctagcat tgttggcgga gcaagtgaag     180
caatatattg atcaaaaatt tgcgcccag caaccagtgg atttaattgg ttttagtatg      240
ggagggttag taacccgtta ttatttacaa cgactggggg gggggaacg ggttaggcgc      300
tacatcacca tttcagcccc caaccaaggt actctcctgg gttatagttt gccccaccaa     360
ggagtgaggg aaatggcctg gcagagtgac tttttgaggg atttaaaccg agattgttgt     420
cagttattag cgggactcca ggtgacggtg atttggaccc ccttcgactt gatgattctg     480
ccccccagta gttccatttt agaaattgga caagaaatta ttttgcctgt gctggtccat     540
gcctggatgg tgtcggatgc ccgttgtttg gcagaggtgg cttcggcttt ggctaaaccg     600
ttgccctga                                                             609
```

<210> SEQ ID NO 22
<211> LENGTH: 202
<212> TYPE: PRT
<213> ORGANISM: Synechocystis PCC 6803

<400> SEQUENCE: 22

```
Met Val Ala Glu Phe Pro Asp Arg His Pro Val Val Leu Val His Gly
1               5                   10                  15
Ile Tyr Asp Thr Arg Ala Lys Phe Ala Thr Met Val Asp Phe Leu Thr
            20                  25                  30
Lys Gly Gly Trp Ser Val His Cys Leu Asp Leu Val Pro Asn Asp Gly
        35                  40                  45
Ser Thr Ser Leu Ala Leu Leu Ala Glu Gln Val Lys Gln Tyr Ile Asp
    50                  55                  60
Gln Lys Phe Ala Pro Gln Gln Pro Val Asp Leu Ile Gly Phe Ser Met
65                  70                  75                  80
Gly Gly Leu Val Thr Arg Tyr Tyr Leu Gln Arg Leu Gly Gly Gly Glu
                85                  90                  95
Arg Val Arg Arg Tyr Ile Thr Ile Ser Ala Pro Asn Gln Gly Thr Leu
            100                 105                 110
Leu Gly Tyr Ser Leu Pro His Gln Gly Val Arg Glu Met Ala Trp Gln
        115                 120                 125
Ser Asp Phe Leu Arg Asp Leu Asn Arg Asp Cys Cys Gln Leu Leu Ala
    130                 135                 140
Gly Leu Gln Val Thr Val Ile Trp Thr Pro Phe Asp Leu Met Ile Leu
145                 150                 155                 160
Pro Pro Ser Ser His Leu Glu Ile Gly Gln Glu Ile Ile Leu Pro
                165                 170                 175
Val Leu Val His Ala Trp Met Val Ser Asp Ala Arg Cys Leu Ala Glu
            180                 185                 190
Val Ala Ser Ala Leu Ala Lys Pro Leu Pro
        195                 200
```

<210> SEQ ID NO 23
<211> LENGTH: 1224
<212> TYPE: DNA

<213> ORGANISM: Synechocystis PCC 6803

<400> SEQUENCE: 23

```
atgccaatgg cgctttgggg catcgtttcc atcaaccagt ccagcccgac caggagagca      60
tcaaccatgg gcatctttaa ccgccgccga ctattgctgg ggggagtggc cctgggggga     120
gcattcacca taggccggga ggaacgccat cgccaggaaa tcagggaatt acaggcatta     180
gccaaagccc aagcggccaa caccgaccgc accagcatgt taaatgccgc ctttgaagcg     240
gatgcggaaa aaatttaccg gggcgaggaa attattaaca gtgttaggct cactccccct     300
atcctgccct acgatcgcca aatttcccaa ttgctgatcc gttgcagtaa aatcgccacc     360
cagcaatact taactgggaa aaccatccct agctacgacg gcaatattcg ccagttaccg     420
gcctatagct ccgacctgga tgagtataaa caaattgctt cttttcgcgg tagggaagct     480
cacatttccg aatccgttgc ggtgcaaatt cccctggata taccggtga ccccttagat      540
aaaacctggg accaagcgga agattccctg ggggaaacca ttcgtcaagt ggtcaaagta     600
acccaggaaa tccccgttta cctgggtttt atcctcagtt ctccccgccg caatctcatt     660
gtttttcggg gtacccaaac caccatggaa tgggtcaata atctccgggc caacaaatt      720
cccttcaccg aacggcgatc ggggcaatat tttggcaaaa ttcaccaggg ctttatcgaa     780
aattatctcc gtattgtcag tcccattccg agggaaattg cccagcagtt agacccggcc     840
gtgccctgtt acgtcactgg ccatagtttg ggggcttccc tggcggtgct ggcggcgttg     900
gatctagcgg ttaacctccc caacttacgg tcccagattc aactttatag ctatgcctgc     960
cccagggtcg gcgatgtgac ctttgcccaa ctccattccc gccaagtgcc caacagttac    1020
cgtattgtta acctcgcaga cgtgattccc ctcctgcccc ccactacggg gttaggcacc    1080
tatgtccatg tcgggcaaag ttggagtttc tcagccaag gaggggacat cttacccaac     1140
catgtggtgg atacctacca gggagcagtg gataggaag tggaaacgga tcagtccaga     1200
gattatccaa tcgccgccgt ttga                                            1224
```

<210> SEQ ID NO 24
<211> LENGTH: 407
<212> TYPE: PRT
<213> ORGANISM: Synechocystis PCC 6803

<400> SEQUENCE: 24

```
Met Pro Met Ala Leu Trp Gly Ile Val Ser Ile Asn Gln Ser Ser Pro
1               5                   10                  15

Thr Arg Arg Ala Ser Thr Met Gly Ile Phe Asn Arg Arg Leu Leu
            20                  25                  30

Leu Gly Gly Val Ala Leu Gly Gly Ala Phe Thr Ile Gly Arg Glu Glu
        35                  40                  45

Arg His Arg Gln Glu Ile Arg Glu Leu Gln Ala Leu Ala Lys Ala Gln
    50                  55                  60

Ala Ala Asn Thr Asp Arg Thr Ser Met Leu Asn Ala Ala Phe Glu Ala
65                  70                  75                  80

Asp Ala Glu Lys Ile Tyr Arg Gly Glu Glu Ile Ile Asn Ser Val Arg
                85                  90                  95

Leu Thr Pro Pro Ile Leu Pro Tyr Asp Arg Gln Ile Ser Gln Leu Leu
            100                 105                 110

Ile Arg Cys Ser Lys Ile Ala Thr Gln Gln Tyr Leu Thr Gly Lys Thr
        115                 120                 125

Ile Pro Ser Tyr Asp Gly Asn Ile Arg Gln Leu Pro Ala Tyr Ser Ser
```

```
                130              135               140
Asp Leu Asp Glu Tyr Lys Gln Ile Ala Ser Phe Arg Gly Arg Glu Ala
145                 150                 155                 160

His Ile Ser Glu Ser Val Ala Val Gln Ile Pro Leu Asp Asn Thr Gly
                165                 170                 175

Asp Pro Leu Asp Lys Thr Trp Asp Gln Ala Glu Asp Ser Leu Gly Glu
            180                 185                 190

Thr Ile Arg Gln Val Val Lys Val Thr Gln Glu Ile Pro Val Tyr Leu
        195                 200                 205

Gly Phe Ile Leu Ser Ser Pro Arg Arg Asn Leu Ile Val Phe Arg Gly
    210                 215                 220

Thr Gln Thr Thr Met Glu Trp Val Asn Asn Leu Arg Ala Gln Gln Ile
225                 230                 235                 240

Pro Phe Thr Glu Arg Arg Ser Gly Gln Tyr Phe Gly Lys Ile His Gln
                245                 250                 255

Gly Phe Ile Glu Asn Tyr Leu Arg Ile Val Ser Pro Ile Pro Arg Glu
            260                 265                 270

Ile Ala Gln Gln Leu Asp Pro Ala Val Pro Cys Tyr Val Thr Gly His
        275                 280                 285

Ser Leu Gly Ala Ser Leu Ala Val Leu Ala Ala Leu Asp Leu Ala Val
    290                 295                 300

Asn Leu Pro Asn Leu Arg Ser Gln Ile Gln Leu Tyr Ser Tyr Ala Cys
305                 310                 315                 320

Pro Arg Val Gly Asp Val Thr Phe Ala Gln Leu His Ser Arg Gln Val
                325                 330                 335

Pro Asn Ser Tyr Arg Ile Val Asn Leu Ala Asp Val Ile Pro Leu Leu
            340                 345                 350

Pro Pro Thr Thr Gly Leu Gly Thr Tyr Val His Val Gly Gln Ser Trp
        355                 360                 365

Ser Phe Leu Ser Gln Gly Gly Asp Ile Leu Pro Asn His Val Val Asp
    370                 375                 380

Thr Tyr Gln Gly Ala Val Asp Arg Glu Val Glu Thr Asp Gln Ser Arg
385                 390                 395                 400

Asp Tyr Pro Ile Ala Ala Val
            405
```

<210> SEQ ID NO 25
<211> LENGTH: 981
<212> TYPE: DNA
<213> ORGANISM: Saccharomyces cerevisiae

<400> SEQUENCE: 25

```
atgaaaaatg ataataaagc taatgatata ataatagact ccgtcaaagt tcctgattcg    60
tacaagcccc caaaaaatcc tattgtattt tgccatggtt tatcaggatt tgacaaatta   120
attctaatcc cttctgtatt ccatctgaca aacctaattt ccaattcaat agtacataat   180
atggcagaaa atttcatgca ggatgacgaa gataagagtg ataacaagta cacaaatttg   240
ttggagattg aatattggat tggcgttaaa aaatttcttc aatctaaggg atgtactgtt   300
atcaccacta aggtaccagg ttttggtagc atcgaggaaa gagcaatggc tttggatgct   360
cagttacaga agaagtaaa gaaaatcgag tcgaaggata agcgacattc gttaaatcta   420
atcgcacact caatgggggg actagactgc cgatatctaa tttgcaatat aaaaaatagg   480
aattacgata tattgagcct aaccactatt tcaactccac atagagggtc agaaatggcc   540
```

```
gattacgtag tcgacctttt tgaaaatcta atgccttga gagttagcca aaagatattg    600
ccaatatgtt tctaccaact cacgactgcg tatatgaaat atttcaattt ggttacgcca    660
aatagtccaa aagtctctta tttttcgtat ggatgctcct ttgtgcctaa gtggtacaat    720
gtcttttgta ctccctggaa aattgtttat gaaaggtcta aaggttgccc caacgatggc    780
cttgtaacca taaatagtag taaatggggt gaatacaggg ggactttgaa ggacatggat    840
catctggacg tcatcaattg gaaaaataag ttacaggatg attggagtaa atttttcgt     900 accactactg tcggagagaa ggttgacatc ctgaattttt acttgaagat aaccgatgac    960
ttggcaagaa aaggatttta a                                              981
```

<210> SEQ ID NO 26
<211> LENGTH: 326
<212> TYPE: PRT
<213> ORGANISM: Saccharomyces cerevisiae

<400> SEQUENCE: 26

```
Met Lys Asn Asp Asn Lys Ala Asn Asp Ile Ile Ile Asp Ser Val Lys
1               5                   10                  15

Val Pro Asp Ser Tyr Lys Pro Lys Asn Pro Ile Val Phe Cys His
            20                  25                  30

Gly Leu Ser Gly Phe Asp Lys Leu Ile Leu Pro Ser Val Phe His
        35                  40                  45

Leu Thr Asn Leu Ile Ser Asn Ser Ile Val His Asn Met Ala Glu Asn
    50                  55                  60

Phe Met Gln Asp Glu Asp Lys Ser Asp Asn Lys Tyr Thr Asn Leu
65                  70                  75                  80

Leu Glu Ile Glu Tyr Trp Ile Gly Val Lys Lys Phe Leu Gln Ser Lys
                85                  90                  95

Gly Cys Thr Val Ile Thr Thr Lys Val Pro Gly Phe Gly Ser Ile Glu
            100                 105                 110

Glu Arg Ala Met Ala Leu Asp Ala Gln Leu Gln Lys Glu Val Lys Lys
        115                 120                 125

Ile Glu Ser Lys Asp Lys Arg His Ser Leu Asn Leu Ile Ala His Ser
    130                 135                 140

Met Gly Gly Leu Asp Cys Arg Tyr Leu Ile Cys Asn Ile Lys Asn Arg
145                 150                 155                 160

Asn Tyr Asp Ile Leu Ser Leu Thr Thr Ile Ser Thr Pro His Arg Gly
                165                 170                 175

Ser Glu Met Ala Asp Tyr Val Val Asp Leu Phe Glu Asn Leu Asn Ala
            180                 185                 190

Leu Arg Val Ser Gln Lys Ile Leu Pro Ile Cys Phe Tyr Gln Leu Thr
        195                 200                 205

Thr Ala Tyr Met Lys Tyr Phe Asn Leu Val Thr Pro Asn Ser Pro Lys
    210                 215                 220

Val Ser Tyr Phe Ser Tyr Gly Cys Ser Phe Val Pro Lys Trp Tyr Asn
225                 230                 235                 240

Val Phe Cys Thr Pro Trp Lys Ile Val Tyr Glu Arg Ser Lys Gly Cys
                245                 250                 255

Pro Asn Asp Gly Leu Val Thr Ile Asn Ser Ser Lys Trp Gly Glu Tyr
            260                 265                 270

Arg Gly Thr Leu Lys Asp Met Asp His Leu Asp Val Ile Asn Trp Lys
        275                 280                 285

Asn Lys Leu Gln Asp Asp Trp Ser Lys Phe Phe Arg Thr Thr Thr Val
```

```
                290                 295                 300
Gly Glu Lys Val Asp Ile Leu Asn Phe Tyr Leu Lys Ile Thr Asp Asp
305                 310                 315                 320

Leu Ala Arg Lys Gly Phe
            325
```

<210> SEQ ID NO 27
<211> LENGTH: 21
<212> TYPE: DNA
<213> ORGANISM: Artificial Sequence
<220> FEATURE:
<223> OTHER INFORMATION: forward primer RS6803-5

<400> SEQUENCE: 27
attgctgaag cggaatccct g                                            21

<210> SEQ ID NO 28
<211> LENGTH: 58
<212> TYPE: DNA
<213> ORGANISM: Artificial Sequence
<220> FEATURE:
<223> OTHER INFORMATION: reverse primer RSMCS-3

<400> SEQUENCE: 28
catggagatc tgagctcgca tgcatatggt accatataac catcaaagcc atagttgg    58

<210> SEQ ID NO 29
<211> LENGTH: 58
<212> TYPE: DNA
<213> ORGANISM: Artificial Sequence
<220> FEATURE:
<223> OTHER INFORMATION: forward primer RSMCS-5

<400> SEQUENCE: 29
atatgcatgc gagctcagat ctccatggaa ttcggtaccg gtatggatgg caccgatg    58

<210> SEQ ID NO 30
<211> LENGTH: 21
<212> TYPE: DNA
<213> ORGANISM: Artificial Sequence
<220> FEATURE:
<223> OTHER INFORMATION: reverse primer RS6803-3

<400> SEQUENCE: 30
tgggggacca ttctctggat c                                            21

<210> SEQ ID NO 31
<211> LENGTH: 39
<212> TYPE: DNA
<213> ORGANISM: Artificial Sequence
<220> FEATURE:
<223> OTHER INFORMATION: forward primer NS2-5MCS

<400> SEQUENCE: 31
gcatgcgagc tcagatctac caggttgtcc ttggcgcag                         39

<210> SEQ ID NO 32
<211> LENGTH: 39
<212> TYPE: DNA
<213> ORGANISM: Artificial Sequence
<220> FEATURE:
<223> OTHER INFORMATION: reverse primer NS21-3MCS

<400> SEQUENCE: 32
ccataccggt accgaattcg ccacgttact gctcgatgg                         39

<210> SEQ ID NO 33
<211> LENGTH: 220
<212> TYPE: DNA
<213> ORGANISM: Eschericia coli

<400> SEQUENCE: 33
tgttgacaat taatcatccg gctcgtataa tgtgtggaat tgtgagcgga taacaatttc      60
acacaggaaa cagcgccgct gagaaaaagc gaagcggcac tgctctttaa caatttatca    120
gacaatctgt gtgggcactc gaccggaatt atcgattaac tttattatta aaaattaaag    180
aggtatatat taatgtatcg attaaataag gaggaataaa                           220

<210> SEQ ID NO 34
<211> LENGTH: 26
<212> TYPE: DNA
<213> ORGANISM: Artificial Sequence
<220> FEATURE:
<223> OTHER INFORMATION: forward primer 2645

<400> SEQUENCE: 34
atgaagactg aacttcacgt tccgag                                           26

<210> SEQ ID NO 35
<211> LENGTH: 26
<212> TYPE: DNA
<213> ORGANISM: Artificial Sequence
<220> FEATURE:
<223> OTHER INFORMATION: reverse primer 2645

<400> SEQUENCE: 35
tctggatgat tgtgctgaca tttcta                                           26

<210> SEQ ID NO 36
<211> LENGTH: 27
<212> TYPE: DNA
<213> ORGANISM: Artificial Sequence
<220> FEATURE:
<223> OTHER INFORMATION: forward primer 2651

<400> SEQUENCE: 36
atgaggcgag aaaaactcaa gctgttg                                          27

<210> SEQ ID NO 37
<211> LENGTH: 30
<212> TYPE: DNA
<213> ORGANISM: Artificial Sequence
<220> FEATURE:
<223> OTHER INFORMATION: reverse primer 2651

<400> SEQUENCE: 37
gagaacctcc agagacagaa tcgtttgatc                                       30

<210> SEQ ID NO 38
<211> LENGTH: 22
<212> TYPE: DNA
<213> ORGANISM: Artificial Sequence
<220> FEATURE:
<223> OTHER INFORMATION: forward primer for 8896

<400> SEQUENCE: 38
atgcctaccc cacgcaactc ga                                               22

<210> SEQ ID NO 39

-continued

```
<211> LENGTH: 26
<212> TYPE: DNA
<213> ORGANISM: Artificial Sequence
<220> FEATURE:
<223> OTHER INFORMATION: reverse primer 8896

<400> SEQUENCE: 39
tttagcaatt gaccgaggtg gctgat                                              26

<210> SEQ ID NO 40
<211> LENGTH: 27
<212> TYPE: DNA
<213> ORGANISM: Artificial Sequence
<220> FEATURE:
<223> OTHER INFORMATION: forward primer 66707

<400> SEQUENCE: 40
atggttagcc gtcaagggta tagattc                                             27

<210> SEQ ID NO 41
<211> LENGTH: 23
<212> TYPE: DNA
<213> ORGANISM: Artificial Sequence
<220> FEATURE:
<223> OTHER INFORMATION: reverse primer 66707

<400> SEQUENCE: 41
caaaaccgat agcgctcaac cag                                                 23

<210> SEQ ID NO 42
<211> LENGTH: 21
<212> TYPE: DNA
<213> ORGANISM: Artificial Sequence
<220> FEATURE:
<223> OTHER INFORMATION: forward primer 31043

<400> SEQUENCE: 42
gtggcaggag agttcacgat g                                                   21

<210> SEQ ID NO 43
<211> LENGTH: 32
<212> TYPE: DNA
<213> ORGANISM: Artificial Sequence
<220> FEATURE:
<223> OTHER INFORMATION: reverse primer 31043

<400> SEQUENCE: 43 cccccgctc acgatccggt cgcgcagcat ct                                        32

<210> SEQ ID NO 44
<211> LENGTH: 20
<212> TYPE: DNA
<213> ORGANISM: Artificial Sequence
<220> FEATURE:
<223> OTHER INFORMATION: forward primer 31046

<400> SEQUENCE: 44
atgacggtcg gtccggagaa                                                     20

<210> SEQ ID NO 45
<211> LENGTH: 26
<212> TYPE: DNA
<213> ORGANISM: Artificial Sequence
<220> FEATURE:
<223> OTHER INFORMATION: reverse primer 31046

<400> SEQUENCE: 45
```

```
gcaatcctcg tccagcgccg cctgca                                          26

<210> SEQ ID NO 46
<211> LENGTH: 26
<212> TYPE: DNA
<213> ORGANISM: Artificial Sequence
<220> FEATURE:
<223> OTHER INFORMATION: forward primer 43495

<400> SEQUENCE: 46
ttggaaaatc gcaaggaaaa aatcct                                          26

<210> SEQ ID NO 47
<211> LENGTH: 22
<212> TYPE: DNA
<213> ORGANISM: Artificial Sequence
<220> FEATURE:
<223> OTHER INFORMATION: reverse primer 43495

<400> SEQUENCE: 47
tcgcgtgatt aacggccttc tt                                              22

<210> SEQ ID NO 48
<211> LENGTH: 25
<212> TYPE: DNA
<213> ORGANISM: Artificial Sequence
<220> FEATURE:
<223> OTHER INFORMATION: forward primer 54379

<400> SEQUENCE: 48
ttggaaaatc gcaaggaaaa aatcc                                           25

<210> SEQ ID NO 49
<211> LENGTH: 22
<212> TYPE: DNA
<213> ORGANISM: Artificial Sequence
<220> FEATURE:
<223> OTHER INFORMATION: reverse primer 54379

<400> SEQUENCE: 49
tctagcggcc ttcttcacct gg                                              22

<210> SEQ ID NO 50
<211> LENGTH: 28
<212> TYPE: DNA
<213> ORGANISM: Artificial Sequence
<220> FEATURE:
<223> OTHER INFORMATION: forward primer 97362

<400> SEQUENCE: 50
atgtctcgaa tactcgtaat tgacgatg                                        28

<210> SEQ ID NO 51
<211> LENGTH: 33
<212> TYPE: DNA
<213> ORGANISM: Artificial Sequence
<220> FEATURE:
<223> OTHER INFORMATION: reverse primer 97362

<400> SEQUENCE: 51
gttatccgta ttcaattcta agcaataacc agc                                  33

<210> SEQ ID NO 52
<211> LENGTH: 18
<212> TYPE: DNA
```

```
<213> ORGANISM: Artificial Sequence
<220> FEATURE:
<223> OTHER INFORMATION: forward primer 122182

<400> SEQUENCE: 52
atgcctgggg ccggttca                                                        18

<210> SEQ ID NO 53
<211> LENGTH: 22
<212> TYPE: DNA
<213> ORGANISM: Artificial Sequence
<220> FEATURE:
<223> OTHER INFORMATION: reverse primer 122182

<400> SEQUENCE: 53
aaacacgctc taagcgccgt at                                                   22

<210> SEQ ID NO 54
<211> LENGTH: 28
<212> TYPE: DNA
<213> ORGANISM: Artificial Sequence
<220> FEATURE:
<223> OTHER INFORMATION: forward primer YC28 - Fragment 1

<400> SEQUENCE: 54
ggtttattcc tccttattta atcgatac                                             28

<210> SEQ ID NO 55
<211> LENGTH: 22
<212> TYPE: DNA
<213> ORGANISM: Artificial Sequence
<220> FEATURE:
<223> OTHER INFORMATION: reverse primer YC28 - Fragment 1

<400> SEQUENCE: 55
gacgagcatc acaaaaatcg ac                                                   22

<210> SEQ ID NO 56
<211> LENGTH: 25
<212> TYPE: DNA
<213> ORGANISM: Artificial Sequence
<220> FEATURE:
<223> OTHER INFORMATION: forward primer YC28 - Fragment 2

<400> SEQUENCE: 56
taatgatagg atccgagctc agatc                                                25

<210> SEQ ID NO 57
<211> LENGTH: 22
<212> TYPE: DNA
<213> ORGANISM: Artificial Sequence
<220> FEATURE:
<223> OTHER INFORMATION: reverse primer YC28 - Fragment 2

<400> SEQUENCE: 57
gtcgattttt gtgatgctcg tc                                                   22

<210> SEQ ID NO 58
<211> LENGTH: 31
<212> TYPE: DNA
<213> ORGANISM: Artificial Sequence
<220> FEATURE:
<223> OTHER INFORMATION: forward primer RS2-5

<400> SEQUENCE: 58
gggccctatt tgcccgtatt ctgccctatc c                                         31
```

```
<210> SEQ ID NO 59
<211> LENGTH: 32
<212> TYPE: DNA
<213> ORGANISM: Artificial Sequence
<220> FEATURE:
<223> OTHER INFORMATION: reverse primer RS2-3

<400> SEQUENCE: 59
gggcccgact gcctttggtg gtattaccga tg                                 32

<210> SEQ ID NO 60
<211> LENGTH: 70
<212> TYPE: DNA
<213> ORGANISM: Artificial Sequence
<220> FEATURE:
<223> OTHER INFORMATION: primer 4YC-trcY-5

<400> SEQUENCE: 60
actagtcctg aggctgaaat gagctgttga caattaatca tccggctcgt ataatgtgtg   60
gaattgtgag                                                          70

<210> SEQ ID NO 61
<211> LENGTH: 70
<212> TYPE: DNA
<213> ORGANISM: Artificial Sequence
<220> FEATURE:
<223> OTHER INFORMATION: primer 4YC-trcY-3

<400> SEQUENCE: 61
ccatggtttt tttcctcctt agtgtgaaat tgttatccgc tcacaattcc acacattata   60
cgagccggat                                                          70

<210> SEQ ID NO 62
<211> LENGTH: 20
<212> TYPE: DNA
<213> ORGANISM: Artificial Sequence
<220> FEATURE:
<223> OTHER INFORMATION: reverse primer

<400> SEQUENCE: 62
gtctagaggc ctgtcgacga                                               20

<210> SEQ ID NO 63
<211> LENGTH: 20
<212> TYPE: DNA
<213> ORGANISM: Artificial Sequence
<220> FEATURE:
<223> OTHER INFORMATION: forward primer for RS1 integration

<400> SEQUENCE: 63
accctggccc tcagtgcgag                                               20

<210> SEQ ID NO 64
<211> LENGTH: 20
<212> TYPE: DNA
<213> ORGANISM: Artificial Sequence
<220> FEATURE:
<223> OTHER INFORMATION: reverse primer for RS1 integration

<400> SEQUENCE: 64
ctaccgtttg ccgttcgttg                                               20

<210> SEQ ID NO 65
```

```
<211> LENGTH: 20
<212> TYPE: DNA
<213> ORGANISM: Artificial Sequence
<220> FEATURE:
<223> OTHER INFORMATION: forward primer for RS2 integration

<400> SEQUENCE: 65
ccaccgattc cgtggtcagc                                                    20

<210> SEQ ID NO 66
<211> LENGTH: 25
<212> TYPE: DNA
<213> ORGANISM: Artificial Sequence
<220> FEATURE:
<223> OTHER INFORMATION: reverse primer for RS2 integration

<400> SEQUENCE: 66
gtacctatct ccatcctgac cgcag                                              25

<210> SEQ ID NO 67
<211> LENGTH: 20
<212> TYPE: DNA
<213> ORGANISM: Artificial Sequence
<220> FEATURE:
<223> OTHER INFORMATION: forward primer for Cc1FatB1 integration

<400> SEQUENCE: 67
atggtatggg tcgtgattgg                                                    20

<210> SEQ ID NO 68
<211> LENGTH: 21
<212> TYPE: DNA
<213> ORGANISM: Artificial Sequence
<220> FEATURE:
<223> OTHER INFORMATION: reverse primer for Cc1FatB1 integration

<400> SEQUENCE: 68
ctcttggctg acttcgtaag g                                                  21

<210> SEQ ID NO 69
<211> LENGTH: 19
<212> TYPE: DNA
<213> ORGANISM: Artificial Sequence
<220> FEATURE:
<223> OTHER INFORMATION: forward primer for YC28 sequencing 1

<400> SEQUENCE: 69
ctgacgggct tgtctgctc                                                     19

<210> SEQ ID NO 70
<211> LENGTH: 19
<212> TYPE: DNA
<213> ORGANISM: Artificial Sequence
<220> FEATURE:
<223> OTHER INFORMATION: reverse primer for YC28 sequencing 1

<400> SEQUENCE: 70
gagcagacaa gcccgtcag                                                     19

<210> SEQ ID NO 71
<211> LENGTH: 21
<212> TYPE: DNA
<213> ORGANISM: Artificial Sequence
<220> FEATURE:
<223> OTHER INFORMATION: forward primer for YC28 sequencing 2

<400> SEQUENCE: 71
```
cagtcgttgc tgattggcgt t                                              21

<210> SEQ ID NO 72
<211> LENGTH: 21
<212> TYPE: DNA
<213> ORGANISM: Artificial Sequence
<220> FEATURE:
<223> OTHER INFORMATION: reverse primer for YC28 sequencing 2

<400> SEQUENCE: 72
aacgccaatc agcaacgact g                                              21

<210> SEQ ID NO 73
<211> LENGTH: 21
<212> TYPE: DNA
<213> ORGANISM: Artificial Sequence
<220> FEATURE:
<223> OTHER INFORMATION: forward primer for YC28 sequencing 3

<400> SEQUENCE: 73
caacaaacca tgcaaatgct g                                              21

<210> SEQ ID NO 74
<211> LENGTH: 21
<212> TYPE: DNA
<213> ORGANISM: Artificial Sequence
<220> FEATURE:
<223> OTHER INFORMATION: reverse primer for YC28 sequencing 3

<400> SEQUENCE: 74
cagcatttgc atggtttgtt g                                              21

<210> SEQ ID NO 75
<211> LENGTH: 19
<212> TYPE: DNA
<213> ORGANISM: Artificial Sequence
<220> FEATURE:
<223> OTHER INFORMATION: forward primer for YC28 sequencing 4

<400> SEQUENCE: 75
tagcgcgaat tgatctggt                                                 19

<210> SEQ ID NO 76
<211> LENGTH: 19
<212> TYPE: DNA
<213> ORGANISM: Artificial Sequence
<220> FEATURE:
<223> OTHER INFORMATION: reverse primer for YC28 sequencing 4

<400> SEQUENCE: 76
accagatcaa ttcgcgcta                                                 19

<210> SEQ ID NO 77
<211> LENGTH: 20
<212> TYPE: DNA
<213> ORGANISM: Artificial Sequence
<220> FEATURE:
<223> OTHER INFORMATION: forward primer for YC28 sequencing 5

<400> SEQUENCE: 77
tcagacaatc tgtgtgggca                                                20

<210> SEQ ID NO 78
<211> LENGTH: 20
<212> TYPE: DNA

<213> ORGANISM: Artificial Sequence
<220> FEATURE:
<223> OTHER INFORMATION: reverse primer for YC28 sequencing 5

<400> SEQUENCE: 78
tgcccacaca gattgtctga                                                   20

<210> SEQ ID NO 79
<211> LENGTH: 20
<212> TYPE: DNA
<213> ORGANISM: Artificial Sequence
<220> FEATURE:
<223> OTHER INFORMATION: forward primer for YC28 sequencing 6

<400> SEQUENCE: 79
tcgtcgacag gcctctagac                                                   20

<210> SEQ ID NO 80
<211> LENGTH: 40
<212> TYPE: DNA
<213> ORGANISM: Artificial Sequence
<220> FEATURE:
<223> OTHER INFORMATION: reverse primer for YC28 sequencing 6

<400> SEQUENCE: 80
gtctagaggc ctgtcgacga gtctagaggc ctgtcgacga                             40

<210> SEQ ID NO 81
<211> LENGTH: 1089
<212> TYPE: DNA
<213> ORGANISM: Cuphea carthagenensis

<400> SEQUENCE: 81
atggcgaacg gtagcgctgt ctctctgaag agcggctcct tgaatacgca agaggacact        60
tcttcttccc caccgccacg cgcgttcatc aaccaattac ccgactggtc catgttattg       120
acggcgatta ccactgtctt tgttgccgca gagaaacagt ggactatgtt agaccgcaag       180
agcaagcgct ccgatatgtt agtggattct tttggcatgg aacgcattgt gcaggatggc       240
ttagtgtttc gtcaatcttt tagcattcgt tcttatgaaa tcggtgcaga tcgtcgtgca       300
tccattgaaa ccttaatgaa ccatctgcag gaaactagct tgaatcattg caaatccatt       360
cgcttgttga atgagggttt tggtcgcacc cccgagatgt gcaaacgtga cttgatctgg       420
gtggttaccc gcatgcacat catggtcaac cgctacccta cctggggtga taccgttgag       480
attaacactt gggtttccca aagcggcaag aatggtatgg tcgtgattg gctgatttcc       540 gactgtaata ccggcgaaat cctgatccgc gcgacgtctg catgggcgat gatgaaccaa       600
aagacccgtc gtctgtctaa actgccttac gaagtcagcc aagagattgc tccgcacttc       660
gtcgacagcc ctcccgtgat cgaggacggc gaccgtaagt tacacaagtt cgatgtgaaa       720
accggcgaca gcatccgtaa aggtttgact ccgcgttgga tgacttaga tgttaatcag       780 cacgttaaca acgttaagta tatcggctgg atcttagaga gcatgccgac cgaggtcttg       840
gaaactcatg aactgtgttt cttaactctg gagtatcgtc gcgagtgcgg tcgcgatagc       900
gtgctggaat ctgtgaccgc gatggatcct tctaatgaag gtggtcgctc ccactaccag       960
catttactgc gcttggagga cggtactgac atcgttaagg gccgcactga gtggcgtcca      1020
aagaatgccc ggaatattgg tgccattagt accggtaaaa ccagtaatgg taatcccgcc      1080
agttaataa                                                             1089

<210> SEQ ID NO 82
<211> LENGTH: 361
<212> TYPE: PRT
<213> ORGANISM: Cuphea carthagenensis

<400> SEQUENCE: 82

```
Met Ala Asn Gly Ser Ala Val Ser Leu Lys Ser Gly Ser Leu Asn Thr
1               5                   10                  15

Gln Glu Asp Thr Ser Ser Pro Pro Arg Ala Phe Ile Asn Gln
            20                  25                  30

Leu Pro Asp Trp Ser Met Leu Leu Thr Ala Ile Thr Thr Val Phe Val
            35                  40                  45

Ala Ala Glu Lys Gln Trp Thr Met Leu Asp Arg Lys Ser Lys Arg Ser
50                  55                  60

Asp Met Leu Val Asp Ser Phe Gly Met Glu Arg Ile Val Gln Asp Gly
65                  70                  75                  80

Leu Val Phe Arg Gln Ser Phe Ser Ile Arg Ser Tyr Glu Ile Gly Ala
                85                  90                  95

Asp Arg Arg Ala Ser Ile Glu Thr Leu Met Asn His Leu Gln Glu Thr
            100                 105                 110

Ser Leu Asn His Cys Lys Ser Ile Arg Leu Leu Asn Glu Gly Phe Gly
            115                 120                 125

Arg Thr Pro Glu Met Cys Lys Arg Asp Leu Ile Trp Val Val Thr Arg
130                 135                 140

Met His Ile Met Val Asn Arg Tyr Pro Thr Trp Gly Asp Thr Val Glu
145                 150                 155                 160

Ile Asn Thr Trp Val Ser Gln Ser Gly Lys Asn Gly Met Gly Arg Asp
                165                 170                 175

Trp Leu Ile Ser Asp Cys Asn Thr Gly Glu Ile Leu Ile Arg Ala Thr
            180                 185                 190

Ser Ala Trp Ala Met Met Asn Gln Lys Thr Arg Arg Leu Ser Lys Leu
            195                 200                 205

Pro Tyr Glu Val Ser Gln Glu Ile Ala Pro His Phe Val Asp Ser Pro
210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Asn Asn Val Lys Tyr Ile Gly Trp Ile Leu
            260                 265                 270

Glu Ser Met Pro Thr Glu Val Leu Glu Thr His Glu Leu Cys Phe Leu
            275                 280                 285

Thr Leu Glu Tyr Arg Arg Glu Cys Gly Arg Asp Ser Val Leu Glu Ser
290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
                325                 330                 335

Glu Trp Arg Pro Lys Asn Ala Arg Asn Ile Gly Ala Ile Ser Thr Gly
            340                 345                 350

Lys Thr Ser Asn Gly Asn Pro Ala Ser
            355                 360
```

<210> SEQ ID NO 83
<211> LENGTH: 90

```
<212> TYPE: DNA
<213> ORGANISM: Artificial Sequence
<220> FEATURE:
<223> OTHER INFORMATION: TrcY promoter

<400> SEQUENCE: 83
ctgaaatgag ctgttgacaa ttaatcatcc ggctcgtata atgtgtggaa ttgtgagcgg     60
ataacaattt cacactaagg aggaaaaaaa                                     90
```